United States Patent
Kim et al.

(10) Patent No.: US 10,949,973 B2
(45) Date of Patent: Mar. 16, 2021

(54) MEDICAL IMAGE ANALYSIS USING MECHANICAL DEFORMATION INFORMATION

(71) Applicant: Wake Forest University Health Sciences, Winston-Salem, NC (US)

(72) Inventors: Jeongchul Kim, Winston-Salem, NC (US); Youngkyoo Jung, Clemmons, NC (US); Christopher T. Whitlow, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 34 days.

(21) Appl. No.: 16/349,374

(22) PCT Filed: Nov. 22, 2017

(86) PCT No.: PCT/US2017/062922
§ 371 (c)(1),
(2) Date: May 13, 2019

(87) PCT Pub. No.: WO2018/098213
PCT Pub. Date: May 31, 2018

(65) Prior Publication Data
US 2019/0370970 A1     Dec. 5, 2019

Related U.S. Application Data

(60) Provisional application No. 62/425,920, filed on Nov. 23, 2016.

(51) Int. Cl.
*G06K 9/00*     (2006.01)
*G06T 7/00*     (2017.01)
(Continued)

(52) U.S. Cl.
CPC ............ *G06T 7/0016* (2013.01); *G06T 7/254* (2017.01); *G16H 30/40* (2018.01); *G06T 7/49* (2017.01);
(Continued)

(58) Field of Classification Search
CPC ......... G06T 7/00; G06T 7/254; G06T 7/0016; G06T 7/30; G06T 2207/10081;
(Continued)

(56) References Cited

U.S. PATENT DOCUMENTS 5,315,512 A * 5/1994 Roth ................. A61B 8/08
600/442
7,194,122 B2 * 3/2007 Faber ................. G06T 15/08
378/21
(Continued)

FOREIGN PATENT DOCUMENTS

| WO | 2016042037 | 3/2016 | | |
| WO | WO-2016042037 A1 * | 3/2016 | ............. | G06T 5/007 |
| WO | WO-2018098213 A1 * | 5/2018 | ............... | G06T 7/30 |

OTHER PUBLICATIONS

Aljabar et al. "Assessment of brain growth in early childhood using deformation-based morphometry" Neuroimage, 39:348-358 (Jan. 2008).
(Continued)

*Primary Examiner* — Mahendra R Patel
(74) *Attorney, Agent, or Firm* — Myers Bigel, P.A.

(57) ABSTRACT

Post-image acquisition methods, circuits and systems for evaluating medical images of a subject register a region of interest in a first medical image taken at a first point in time to the region of interest in a second image taken before or after the first medical image with voxels from the first and second medical images having a voxel-wise correspondence. The methods, circuits and systems can use line and/or
(Continued)

shape changes of defined 3-D finite elements to electronically determine directional, shear and volumetric changes of the voxels in the region of interest between the first and second medical images.

35 Claims, 38 Drawing Sheets
(19 of 38 Drawing Sheet(s) Filed in Color)

(51) Int. Cl.
    *G06T 7/254* (2017.01)
    *G16H 30/40* (2018.01)
    *G06T 7/49* (2017.01)

(52) U.S. Cl.
    CPC ........... *G06T 2207/10081* (2013.01); *G06T 2207/10088* (2013.01); *G06T 2207/10104* (2013.01); *G06T 2207/10121* (2013.01)

(58) Field of Classification Search
    CPC ........... G06T 2207/30016; G06T 7/49; G06T 2207/10104; G06T 2207/10132; G06T 2207/10121; G06T 2207/10088; G06T 2207/10072; G16H 30/40; A61B 5/055; A61B 6/03; G06K 9/34; G06K 9/00; G06K 9/38
    USPC ........................................................ 382/131
    See application file for complete search history.

(56) References Cited

U.S. PATENT DOCUMENTS

| | | | | |
|---|---|---|---|---|
| 8,031,211 B2* | 10/2011 | Shekhar | ............... | G01T 1/1647 345/648 |
| 8,538,102 B2* | 9/2013 | Dam | ................. | G06K 9/623 382/128 |
| 8,965,089 B2* | 2/2015 | Ghosh | ................. | G06K 9/52 382/128 |
| 10,085,703 B2* | 10/2018 | Salcudean | ................. | A61B 6/50 |
| 2005/0043619 A1* | 2/2005 | Sumanaweera | ........ | G06T 15/08 600/437 |
| 2005/0114831 A1* | 5/2005 | Callegari | ................. | G06T 17/05 717/104 |
| 2010/0195883 A1* | 8/2010 | Patriarche | ............ | G06K 9/3233 382/131 |
| 2011/0058720 A1* | 3/2011 | Lu | ............................ | G06T 7/12 382/131 |
| 2011/0206248 A1* | 8/2011 | Ruijters | ..................... | G06T 7/66 382/128 |
| 2011/0235885 A1* | 9/2011 | Rauch | ..................... | A61B 6/481 382/131 |
| 2013/0231554 A1* | 9/2013 | Jung | ..................... | A61B 5/0263 600/419 |
| 2013/0315448 A1* | 11/2013 | Fletcher | ..................... | G06T 7/33 382/107 |
| 2015/0161791 A1* | 6/2015 | Lorenz | ................. | G06T 7/0014 382/131 |
| 2016/0070436 A1* | 3/2016 | Thomas | ................. | A61B 6/032 715/771 |
| 2018/0129782 A1* | 5/2018 | Himsl | ..................... | A61B 8/468 |
| 2019/0155835 A1* | 5/2019 | Daugharthy | ............. | G06T 7/70 |

OTHER PUBLICATIONS

Andersson et al. "How to correct susceptibility distortions in spin-echo echo-planar images: application to diffusion tensor imaging" NeuroImage, 20:870-888 (2003).

Ashburner et al. "Voxel-Based Morphometry—The Methods" NeuroImage, 11:805-821 (2000).

Aung et al. "Diffusion tensor MRI as a biomarker in axonal and myelin damage" Imaging in Medicine, 5(5):427-440 (2013).

Avants et al. "Symmetric diffeomorphic image registration with cross-correlation: evaluating automated labeling of elderly and neurodegenerative brain" Medical Image Analysis, 12:26-41 (2008).

Avants et al. "A reproducible evaluation of ANTs similarity metric performance in brain image registration" NeuroImage, 54:2033-2044 (2011).

Bakkour et al. "The effects of aging and Alzheimer's disease on cerebral cortical anatomy: Specificity and differential recognition" NeuroImage, 76:332-344 (2013).

Bammer, Roland "Basic principles of diffusion-weighted imaging" European Journal of Radiology, 45:169-184 (2003).

Behrens et al. "Probabilistic diffusion tractography with multiple fibre orientations: What can we gain?" NeuroImage, 34:144-155 (2007).

Beirowski et al. "Quantitative and qualitative analysis of Wallerain degeneration using restricted axonal labelling in YFP-H mice" Journal of Neuroscience Methods, 134:23-35 (2004).

Benjamini et al. "Controlling the False Discovery Rate: a Practical and Powerful Approach to Multuple Testing" Journal of the Royal Statistical Society, Series B, 57(1):289-300 (1995).

Bernstein et al. "Axonal atrophy: the retraction reaction" Current Opinion in Neurobiology, 9:364-370 (1999).

Blitstein et al. "MRI of Cerebral Microhemorrhages" American Journal of Roentgenology, 189:720-725 (2007).

Bompard et al. "Multivariate Longitudinal Shape Analysis of Human Lateral Ventricles During the First Twenty-Four Months of Life" PLoS One, 9:e108306 (2014).

Brouwer et al. "White Matter Development in Early Puberty: A Longitudinal Volumetric and Diffusion Tensor Imaging Twin Study" PLoS One, 7(4):e32316 (2012).

Choe et al. "Regional Infant Brain Development: An MRI-Based Morphometric Analysis in 3 to 13 Month Olds" Cerebral Cortex, 23:2100-2117 (2013).

CorTechs Labs, Inc. "NeuroQuant: Atrophy, Quantified" Product brochure (2 pages) (2015).

Courchesne et al. "Evidence of Brain Overgrowth in the First Year of Life in Autism" Journal of the American Medical Association, 290:337-344 (2003).

Davatzikos et al. "Voxel-Based Morphometry Using the RAVENS Maps: Methods and Validation Using Simulated Longitudinal Atrophy" NeuroImage, 14:1361-1369 (2001).

Debette et al. "The clinical importance of white matter hyperintensities on brain magnetic resonance imaging: systematic review and meta-analysis" The BMJ, 341:1-9 (2010).

Deoni et al. "Mapping Infant Brain Myelination with Magnetic Resonance Imaging" The Journal of Neuroscience, 31:784-791 (2011).

Ehricke et al. "Regularization of bending and crossing white matter fibers in MRI Q-ball fields" Magnetic Resonance Imaging, 29:916-926 (2011).

Evans, Alan C. "The NIH MRI study of normal brain development" NeuroImage, 30:184-202 (2006).

Gao et al. "Functional Network Development During the First Year: Relative Sequence and Socioeconomic Correlations" Cerebral Cortex, 25:2919-2928 (2015).

Gaonkar et al. "Pattern Based Morphometry" Medical Image Computing and Computer-Assisted Intervention, 140:459-466 (2011).

Gilmore et al. "Regional Gray Matter Growth, Sexual Dimorphism, and Cerebral Asymmetry in the Neonatal Brain" The Journal of Neuroscience, 27:1255-1260 (2007).

Gilmore et al. "Longitudinal Development of Cortical and Subcortical Gray Matter from Birth to 2 Years" Cerebral Cortex, 22:2478-2485 (2012).

Glasser et al. "The Human Connectome Project's neuroimaging approach" Nature Neuroscience, 19(9):1175-1187 (Aug. 2016).

Gogtay et al. "Dynamic mapping of human cortical development during childhood through early adulthood" The Proceedings of the National Academy of Sciences, USA, 101:8174-8179 (2004).

(56) References Cited

OTHER PUBLICATIONS

Gogtay et al. "Three-dimensional brain growth abnormalities in childhood-onset schizophrenia visualized by using tensor-based morphometry" The Proceedings of the National Academy of Sciences, USA, 105:15979-15984 (2008).
Greve et al. "Accurate and robust brain image alignment using boundary-based registration" NeuroImage, 48:63-72 (2009).
Hazlett et al. "Magnetic Resonance Imaging and Head Circumference Study of Brain Size in Autism: Birth Through Age 2 Years" Archives of General Psychiatry, 62:1366-1376 (2005).
Herbert et al. "Brain asymmetries in autism and developmental language disorder: a nested whole-brain analysis" Brain, 128:213-226 (2005).
Holland et al. "Structural Growth Trajectories and Rates of Change in the First 3 Months of Infant Brain Development" JAMA Neurology, 71:1266-1274 (2014).
Hua et al. "Detecting Brain Growth Patterns in Normal Children using Tensor-Based Morphometry" Human Brain Mapping, 30:209-219 (2009).
Hua et al. "Unbiased tensor-based morphometry: Improved robustness and sample size estimates for Alzheimer's disease clinical trials" NeuroImage, 66:648-661 (2013).
Huttenlocher et al. "Regional Differences in Synaptogenesis in Human Cerebral Cortex" The Journal of Comparative Neurology, 387:167-178 (1997).
International Search Report and the Written Opinion of the International Searching Authority corresponding to International Patent Application No. PCT/US2017/062922 (6 pages) (dated Feb. 21, 2018).
Janmey et al. "Mechanisms of mechanical signaling in development and disease" Journal of Cell Science, 124:9-18 (2011).
Johnson et al. "Axonal pathology in traumatic brain injury" Experimental Neurology, 246:35-43 (2013).
Jones et al. "White matter integrity, fiber count, and other fallacies: The do's and don'ts of diffusion MRI" NeuroImage, 73:239-254 (2013).
Kanwisher et al. "The fusiform face area: a cortical region specialized for the perception of faces" Philosophical Transactions of the Royal Society B, 361:2109-2128 (2006).
Keihaninejad et al. "An unbiased longitudinal analysis framework for tracking white matter changes using diffusion tensor imaging with application to Alzheimer's disease" NeuroImage, 72:153-163 (2013).
Kim et al. "Biomechanical Analysis of Normal Brain Development during the First Year of Life Using Finite Strain Theory" Scientific Reports, 6(37666):1-13 (Dec. 2016).
Kim et al. "Biomechanical Characterization of Brain Atrophy in Cognitively Normal and MCI Groups" Poster/abstract submitted to the 2017 Alzheimer's Association International Conference (6 pages) (Jul. 2017).
Knickmeyer et al. "A Structural MRI Study of Human Brain Development from Birth to 2 Years" The Journal of Neuroscience, 28:12176-12182 (2008).
Kuhl, Ellen "Growing matter: A review of growth in living systems" Journal of the Mechanical Behavior of Biomedical Materials, 29:529-543 (2014).
Laird et al. "Random-Effects Models for Longitudinal Data" Biometrics, 38:963-974 (1982).
Lauria et al. "Axonal swellings predict the degeneration of epidermal nerve fibers in painful neuropathies" Neurology, 61:631-636 (2003).
Lazarus et al. "Torsional Behavior of Axonal Microtubule Bundles" Biophysical Journal, 109:231-239 (2015).
Le Bihan et al. "Molecular diffusion, tissue microdynamics and microstructure" NMR in Biomedicine, 8(7-8):375-386 (1995) (Abstract only).
Le Bihan et al. "Diffusion Tensor Imaging: Concepts and Applications" Journal of Magnetic Resonance Imaging, 13:534-546 (2001).
Lebel et al. "Longitudinal Development of Human Brain Wiring Continues from Childhood into Adulthood" The Journal of Neuroscience, 31(30):10937-10947 (2011).
Lebel et al. "A review of diffusion MRI of typical white matter development from early childhood to young adulthood" NMR in Biomedicine, e3778:1-23 (Sep. 2017).
Lee et al. "3D pattern of brain abnormalities in Fragile X syndrome visualized using tensor-based morphometry" NeuroImage, 34:924-938 (2007).
Lenroot et al. "Brain development in children and adolescents: Insights from anatomical magnetic resonance imaging" Neuroscience and Biobehavioral Reviews, 30:718-729 (2006).
Lepore et al. "Generalized Tensor-Based Morphometry of HIV/AIDS Using Multivariate Statistics on Deformation Tensors" IEEE Transactions on Medical Imaging, 27(1):129-141 (Jan. 2008).
Li et al. "Mapping Longitudinal Development of Local Cortical Gyrification in Infants from Birth to 2 Years of Age" The Journal of Neuroscience, 34:4228-4238 (2014).
Matsuzawa et al. "Age-related Volumetric Changes of Brain Gray and White Matter in Healthy Infants and Children" Cerebral Cortex, 11:335-342 (2001).
Maxwell et al. "Ultrastructural evidence of axonal shearing as a result of lateral acceleration of the head in non-human primates" Acta Neuropathologica, 86(2):136-144 (1993) (Abstract only).
Meltzer et al. "Comparative Evaluation of MR-Based Partial-Volume Correction Schemes for PET" The Journal of Nuclear Medicine, 40:2053-2065 (1999).
Mills et al. "Methods and considerations for longitudinal structural brain imaging analysis across development" Developmental Cognitive Neuroscience, 9:172-190 (2014).
Nakamura et al. "Segmentation of brain magnetic resonance images for measurement of gray matter atrophy in multiple sclerosis patients" NeuroImage, 44:769-776 (2009).
Nakamura et al. "Jacobian integration method increases the statistical power to measure gray matter atrophy in multiple sclerosis" NeuroImage: Clinical, 4:10-17 (2014).
Palacios et al. "Toward Precision and Reproducibility of Diffusion Tensor Imaging: A Multicenter Diffusion Phantom and Traveling Volunteer Study" American Journal of Neuroradiology, 38:537-545 (Mar. 2017).
Pantoni et al. "Cerebral White Matter Is Highly Vulnerable to Ischemia" Stroke, 27:1641-1647 (1996).
Radanovic et al. "White matter abnormalities associated with Alzheimer's disease and mild cognitive impairment: a critical review of MRI studies" Expert Review of Neurotherapeutics, 13(5):483-493 (2013).
Raffelt et al. "Apparent Fibre Density: A novel measure for the analysis of diffusion-weighted magnetic resonance images" NeuroImage, 59:3976-3994 (Feb. 2012).
Raffelt et al. "Investigating white matter fibre density and morphology using fixel-based analysis" NeuroImage, 144:58-73 (Jan. 2017).
Rajagopalan et al. "*Drosophila* Neurons Actively Regulate Axonal Tension In Vivo" Biophysical Journal, 99:3208-3215 (2010).
Rajagopalan et al. "Local Tissue Growth Patterns Underlying Normal Fetal Human Brain Gyrification Quantified in Utero " The Journal of Neuroscience, 31:2878-2887 (2011).
Rajagopalan et al. "Mapping directionality specific volume changes using tensor based morphometry: An application to the study of gyrogenesis and lateralization of the human fetal brain" NeuroImage, 63(2):947-958 (Nov. 2012).
Sabatinelli et al. "Emotional perception: meta-analyses of face and natural scene processing" NeuroImage, 54:2524-2533 (2011).
Shen et al. "Measuring temporal morphological changes robustly in brain MR images via 4-dimensional template warping" NeuroImage, 21:1508-1517 (2004).
Shi et al. "Infant Brain Atlases from Neonates to 1- and 2-Year-Olds" PLoS One, 6:e18746 (2011).
Sotak, Christopher H. "Nuclear magnetic resonance (NMR) measurement of the apparent diffusion coefficient (ADC) of tissue and water and its relationship to cell volume changes in pathological states" Neurochemistry International, 45:569-582 (2004).

(56) References Cited

OTHER PUBLICATIONS

Sperling et al. "Toward defining the preclinical stages of Alzheimer's disease: Recommendations from the National Institute on Aging-Alzheimer's Association workgroups on diagnostic guidelines for Alzheimer's disease" Alzheimer's & Dementia, 7:280-292 (2011).
Stiles et al. "The Basics of Brain Development" Neuropsychology Review, 20(4):327-348 (2010).
Studholme et al. "Population Based Analysis of Directional Information in Serial Deformation Tensor Morphometry" Medical Image Computing and Computer-Assisted Intervention, 10:311-318 (2007).
Suter et al. "The emerging role of forces in axonal elongation" Progress in Neurobiology, 94:91-101 (Apr. 2011).
Teipel et al. "Longitudinal Changes in Fiber Tract Integrity in Healthy Aging and Mild Cognitive Impairment: A DTI Follow-Up Study" Journal of Alzheimer's Disease, 22:507-522 (2010).
Thompson et al. "Growth patterns in the developing brain detected by using continuum mechanical tensor maps" Letters to Nature, 404:190-193 (Mar. 2000).
Toga et al. "Mapping Brain Asymmetry" Nature Reviews Neuroscience, 4:37-48 (2003).
Toro, Roberto "On the Possible Shapes of the Brain" Evolutionary Biology, 39:600-612 (2012).
Urban et al. "Head Impact Exposure in Youth Football: High School Ages 14 to 18 Years and Cumulative Impact Analysis" Annals of Biomedical Engineering, 41(12):2474-2487 (2013).
Wang et al. "4D Multi-Modality Tissue Segmentation of Serial Infant Images" PLoS One, 7:e44596 (2012).
Wang et al. "A comprehensive reliability assessment of quantitative diffusion tensor tractography" NeuroImage, 60:1127-1138 (2012).
Wang et al. "Integration of Sparse Multi-modality Representation and Geometrical Constraint for Isointense Infant Brain Segmentation" Medical Image Computing and Computer-Assisted Intervention, 16:703-710 (2013).
Wang et al. "Integration of Sparse Multi-modality Representation and Anatomical Constraint for Isointense Infant Brain MR Image Segmentation" NeuroImage, 89:152-164 (2014).
Wang et al. "LINKS: Learning-based multi-source IntegratioN frameworK for Segmentation of infant brain images" NeuroImage, 108:160-172 (2015).
Williams et al. "Progression of Alzheimer's disease as measured by Clinical Dementia Rating Sum of Boxes scores" Alzheimer's & Dementia, 9:S39-S44 (2013).
Yoo et al. "Alignment of CT images of skull dysmorphology using anatomy-based perpendicular axes" Physics in Medicine & Biology, 48:2681-2695 (2003).
Yuh et al. "Diffusion Tensor Imaging for Outcome Prediction in Mild Traumatic Brain Injury: A TRACK-TBI Study" Journal of Neurotrauma, 31:1457-1477 (2014).
Zhan et al. "Spatial-temporal atlas of human fetal brain development during the early second trimester" NeuroImage, 82:115-126 (2013).
Zhang et al. "Tensor-Based Morphometry of Fibrous Structures with Application to Human Brain White Matter" Medical Image Computing and Computer-Assisted Intervention, 12:466-473 (2009).
Zhang et al. "A tract-specific framework for white matter morphometry combining macroscopic and microscopic tract features" Medical Image Analysis, 14:666-673 (May 2010).

\* cited by examiner

BEFORE DEFORMATION, V1     AFTER DEFORMATION, V2

| FA | PRE_SEASON | POST_SEASON | CORRECTED_POST_SEASON |
|---|---|---|---|
|  | 0.384 | 0.384 | 0.379 |

COMPLEMENTARY RELATIONS

| | JD | Exx (L-R) | Eyy (P-A) | Ezz (I-S) |
|---|---|---|---|---|
| I | CEREBELLUM-L | CEREBELLUM-L | CEREBELLUM-L | |
| | OFG-R, GCC, ACR-R | | OFG-R, OFG-L, REC-L, REC-R, GCC, ACR-R | |
| | MTG-R, ITG-R, SS-R | | FFG-R, STG-R, MTG-R, PLIC-R, RLIC-R | |
| | MOG-L, PTR-L | | | MOG-L |
| II | SFG-L | | | |
| | INS-L | | | |
| | SFG-R | | | |
| | IFG-L | | | |
| III | | STG-L | | |
| IV | | | | MCG-L/R, SMA-R, PreCG-L, PCG-L, PCL-L |

SHEAR STRAINS ALSO SHOWED GROUP DIFFERENCES

*FIG. 21*

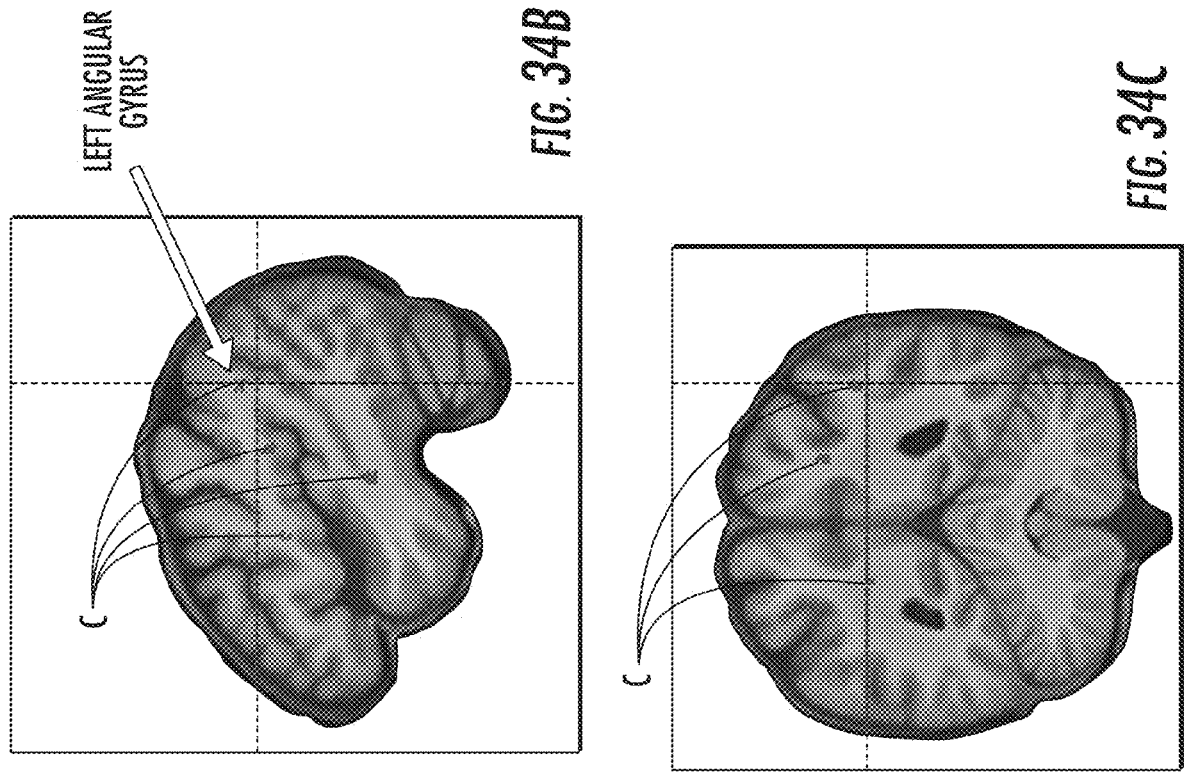
FIG. 34B
FIG. 34C
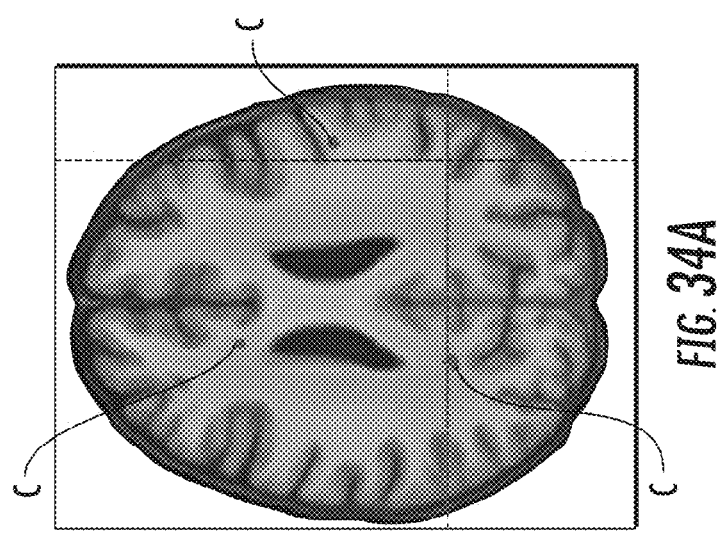
FIG. 34A

MEDICAL IMAGE ANALYSIS USING MECHANICAL DEFORMATION INFORMATION

RELATED APPLICATIONS

This application claims the benefit of and priority to U.S. Provisional Application Ser. No. 62/425,920, filed Nov. 23, 2016, the content of which is hereby incorporated by reference as if recited in full herein.

FIELD OF THE INVENTION

This invention relates to medical image evaluations.

BACKGROUND

Neuro-degenerative diseases such as Alzheimer's disease (AD) can be characterized by a chronic loss of neurons and synapses in the temporal and parietal lobes of the brain. Studies using magnetic resonance imaging (MRI) have suggested that biomarkers related to changes in local tissue volume are the Jacobian determinant (JD) and cortical thickness (CTHK). See, Bakkour et al., The effects of aging and Alzheimer's disease on cerebral cortical anatomy: Specificity and differential recognition; Neuroimage, 2013; 76: pp. 332-344. However, the annual atrophy rate of the temporal lobe can be very small (<2%) in adults with mild cognitive impairment (MCI). See, Hua et al., Unbiased tensor-based morphometry: Improved robustness and sample size estimates for Alzheimer's disease clinical trials, Neuroimage, 2013; 66: pp. 648-661. Thus, other parameters or regions of interest (ROIs) may exist that are not detectable by JD or CTHK alone or with any techniques currently known by the inventors.

SUMMARY OF EMBODIMENTS THE INVENTION

Embodiments of the present application provide medical image analyses that employ finite strain theory of continuum mechanics to estimate strain tensors for evaluating directional changes (stretch, shrink/compression and/or shear strain) of one or more voxels in medical images of a subject taken over time.

Embodiments of the invention can evaluate longitudinal medical images of a subject by registering a region of interest in a first medical image taken at a first point in time to the region of interest in a second image taken before or after the first medical image with voxels from the first and second medical images having a voxel-wise correspondence; and using line and/or shape changes of defined 3-D finite elements that connect a plurality of neighboring voxels to electronically determine directional and shear changes of the voxels in the region of interest between the first and second medical images.

Embodiments of the invention are directed to a post-image acquisition method of evaluating medical images of a subject that includes: (a) registering a region of interest in a first medical image taken at a first point in time to the region of interest (ROI) in a second image taken before or after the first medical image with voxels from the first and second medical images having a voxel-wise correspondence; (b) electronically defining a plurality of three-dimensional (3-D) finite elements in the ROI of the first image, each 3-D finite element defined by connecting lines to points (i.e., vertices) associated with at least four voxels to establish a shape of the 3-D finite element in the ROI of the first image with associated original lengths and lines; (c) electronically deforming the 3-D finite elements in the ROI of the second medical image; then (d) electronically calculating directional, shear and volume changes of the voxels in the ROI between the first and second images based on changes in lengths and angles of the lines in the deformed 3-D finite elements relative to the original lengths and angles.

At least some of the 3-D finite elements can have a three dimensional shape, optionally a tetrahedron shape or a cube shape.

The method can include applying one or more deformation gradient tensors to the deformed 3-D finite elements before the electronically calculating.

The one or more deformation gradient tensors can provide a non-linear deformation and each voxel is evaluated for shape change in three dimensions using the original and deformed 3-D finite elements.

Embodiments of the present application provide medical image analyses using a strain tensor, such as a Lagrangian strain tensor.

Embodiments of the present application can employ a gradient tensor for non-linear deformation of voxels in an ROI that can identify one or more directional components (i.e., diagonal components) associated with stretching and/or shrinking and/or one or more off-diagonal components (i.e., shear strains) between different images taken at different points in time that may be useful for identifying a disease state, disease progression or regression, therapeutic influence associated with morphometric change and the like. The new components may complement volumetric analysis or be used alone.

Embodiments of the invention provide new morphometric parameters that can calculate a shape change in three dimensions for each voxel in a region of interest between first and second images of a subject.

Embodiments of the invention can identify six morphometric parameters associated with directional change in tissue. The six parameters can include left-right (x-), anterior-posterior (y-), and inferior-superior (z-) stretch/shrink, and xy-, yz- and zx-planes of shear deformations.

The morphometric parameters can identify anisotropic and isotropic patterns even where there is no volume change or less than a 5% volume change over a region of interest.

Embodiments of the invention can classify or provide biomarkers that can identify four groups of deformation topology types: Type I: isotropic directional change with a volumetric change; Type II: anisotropic directional change with a volumetric change; Type III: anisotropic directional change without a volumetric change; and Type IV: shear deformation.

Embodiments of the invention can provide color-coded visualizations of a 3-D topology of one or more regions of interest of a subject using a plurality (i.e., two-six) of different directional and shear morphometric parameters that can identify directional/shear changes of voxels of soft tissue.

Embodiments of the invention can generate visualizations that identify left-right stretch ($E_{xx}$), anterior-posterior stretch ($E_{yy}$), inferior-superior stretch ($E_{zz}$) and shear strains $E_{xy}$, $E_{yz}$ and $E_{zx}$ in corresponding shear planes.

Embodiments of the invention can electronically identify voxel-wise three dimensional shape changes using the calculated directional, shear and volume changes of the voxels in the ROI between the first and second images and correct a medical image of the ROI using calculated morphometric parameters provided at least in part by the calculated directional, shear and volume changes of the voxels.

Embodiments of the invention can include methods, circuits and/or systems that convert three-dimensional deformation fields associated with the calculated directional, shear and volume changes of the voxels in the ROI of voxel-wise displacements in a Cartesian coordinate system to a local fiber-specific coordinate system to thereby obtain local deformation fields for each voxel and calculate fiber-orientation-specific deformation measurements based on the converted three-dimensional deformation fields.

Embodiments of the invention can generate a visualization of the ROI that calculates $E_{11}$, $E_{22}$ and $E_{33}$ directional strains as morphometric parameters from the local coordinate system In some embodiments, the first and second images are T1WI brain images.

Embodiments of the invention can include methods, circuits and/or systems that define Eigen vectors from a diffusion tensor imaging (DTI) image of the ROI to provide a local coordinate system; co-register local coordinates of the local coordinate system with the ROI of the first and/or second T1WI brain images; define local deformation fields for each voxel in the ROI; and calculate white matter fiber orientation-specific deformation measures using the local deformation fields.

The local coordinate system $\{e_1, e_2, e_3\}$ can be aligned with Eigen vectors co-registered onto T1WI space associated with the first and second images.

The first and second images can be brain images.

Embodiments of the invention can include methods, circuits and/or systems that: obtain a DTI or DWI brain image; model fiber bundles in the DTI or DWI brain image as cylindrical shapes; generate Eigen vectors aligned with $\{e_1, e_2, e_3\}$ directions of a local coordinate system associated with the cylindrical shapes; co-register the Eigen vectors to deformation fields generated by the calculated directional, shear and volume changes of the voxels; and identify local deformation fields for each voxel in the ROI; and calculating fiber tract-specific morphometric parameters $E_{11}$, $E_{22}$, $E_{33}$, $E_{12}$, $E_{23}$ and $E_{31}$.

The obtained DTI or DWI brain image can be the DTI image.

A single voxel in the ROI may comprise of single fiber or multiple crossing fibers. The methods, circuits and/or systems can, for a respective single voxel having or multiple crossing fiber regions, provide Bayesian estimates for diffusion parameters to generate the Eigen vectors aligned with $\{e_1, e_2, e_3\}$ directions of the local coordinate system associated with the cylindrical shapes for each primary and secondary fiber bundle component.

For each primary and secondary fiber bundle component, the methods, systems and/or circuits can: co-register the Eigen vectors to deformation fields generated by the calculated directional, shear and volume changes of the voxels; then identify the local deformation fields for each voxel in the ROI; and then calculating the fiber tract-specific morphometric parameters $E_{11}$, $E_{22}$, $E_{33}$, $E_{12}$, $E_{23}$ and $E_{31}$.

The obtained DTI or DWI brain image can be the DTI image. The methods, circuits and systems can: generate one or more voxel-wise diffusion parameter maps (one or more of FA, MD, AD, and RD) from the DTI image; identify whether there is brain tissue shrinkage in any of three directions of the local coordinate system; apply correction factors for fiber tract-specific morphometric parameters $E_{11}$, $E_{22}$, $E_{33}$ $E_{12}$, $E_{23}$ and $E_{31}$ for directional strain parameters having negative values; and generate one or more corrected voxel-wise diffusion parameter maps based on the applied correction factors thereby correcting over estimation of diffusion parameters.

The correction factors can include A, B, C, where $A=1+E_{11}$, $B=1+E_{22}$ and $C=1+E_{33}$, and the corrected voxel-wise diffusion parameter map (DP') can be mathematically calculated by: $DP'=DP*A*B*C$.

The correction factors can include $\lambda_1$, $\lambda_2$ and $\lambda_3$, which are directional stretch ratios, and the one or more corrected voxel-wise diffusion parameter maps, DP', can be equal to: $DP*\lambda_1*\lambda_2*\lambda_3$.

The first and second images can be T1WI brain images. The methods, circuits and systems can: identify a gray matter-white matter tissue boundary specific shape change between the first and second images using surface normal vectors for directional strains normal to the tissue boundary ($E_{nn}$); calculate local deformation fields using the surface normal vectors; and correct a voxel-wise Positron Emission Tomography (PET) uptake map using the calculated local deformation fields and the electronically calculated directional, shear and volume changes of the voxels in the ROI between the first and second images.

A local coordinate system $\{e_1, e_2, e_3\}$ associated with the gray matter-white matter tissue boundary specific shape change can be aligned with the surface normal vectors on T1WI space associated with the first and second images for the local deformation fields.

The methods, circuits and systems can: generate one or more voxel-wise uncorrected uptake maps in PET before the correcting step; then identify whether there is brain tissue shrinkage in any of three directions of a local coordinate system associated with the directional strains Enn; then apply correction factors for one or more surface-specific morphometric parameters $E_{11}$, $E_{22}$, $E_{33}$, $E_{12}$, $E_{23}$ and $E_{31}$ based at least in part on the local deformation fields; and generate the corrected voxel-wise PET uptake map based on the applied correction factors thereby correcting directional atrophy in Amyloid/Tau/FDG (fluorodeoxyglucose) PET image of the brain.

Other embodiments are directed to an image analysis system that includes: a circuit in communication with at least one server and/or at least one processor that: registers a region of interest in a first medical image taken at a first point in time to the region of interest (ROI) in a second image taken before or after the first medical image with voxels from the first and second medical images having a voxel-wise correspondence; defines a plurality of three-dimensional (3-D) finite elements in the ROI of the first image, each 3-D finite element defined by connecting lines to points (i.e., vertices) associated with at least four voxels to establish a shape of the 3-D finite element in the ROI of the first image with associated original lengths and lines; deforms the 3-D finite elements in the ROI of the second medical image; then calculates directional, shear and volume changes of the voxels in the ROI between the first and second images based on changes in lengths and angles of the lines in the deformed 3-D finite elements relative to the original lengths and angles.

The at least one server and/or processor can be configured to apply at least one deformation gradient tensor to the deformed 3-D finite elements for the calculations, and wherein the at least one deformation gradient tensor provides a non-linear deformation and each voxel is evaluated for change in three dimensions.

The directional changes can include one more diagonal components for left-right (x-), anterior-posterior (y-), and inferior-superior (z) stretch associated with stretching and/or shrinking, and wherein the shear changes comprise off-diagonal components for shear deformations to xy-, yz- and zx-planes in the deformation gradient tensors.

The directional and shear changes can identify directionally different (anisotropic) brain degeneration or regeneration patterns even when a total volume of the ROI is unchanged.

The system can be incorporated into and/or in communication with a clinician workstation.

The system can be incorporated into and/or in communication with an imaging system.

Still other embodiments are directed to post-image acquisition medical image evaluation circuit. The circuit can include at least one server that communicates with a plurality of workstations. The circuit can: evaluate medical images of a subject register a region of interest in a first medical image taken at a first point in time to the region of interest in a second image taken before or after the first medical image with voxels from the first and second medical images having a voxel-wise correspondence; and use line and/or shape changes of defined 3-D finite elements that connect a plurality of neighboring voxels to electronically determine directional and shear changes of the voxels in the region of interest between the first and second medical images.

It is noted that aspects of the invention described with respect to one embodiment, may be incorporated in a different embodiment although not specifically described relative thereto. That is, all embodiments and/or features of any embodiment can be combined in any way and/or combination. Further, any feature or sub-feature claimed with respect to one claim may be included in another future claim without reservation and such shall be deemed supported in the claims as filed. Thus, for example, any feature claimed with respect to a method claim can be alternatively claimed as part of a system, circuit, computer readable program code or workstation. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 21 is a table showing complementary relationships between the directional changes and the local volume changes according to embodiments of the present invention.

FIGS. 34A-34C are visualizations of the brain associated with exercise intervention for mild cognitive impairment showing clusters of axial strain according to embodiments of the present invention.

FIG. 36A and FIG. 36B are visit 1 and 2 T1WI MRI images, respectively.

FIG. 36C is a visualization using surface normal vectors. FIG. 36D is an uncorrected Amyloid PET image and FIG. 36E is a directional atrophy corrected Amyloid PET image according to embodiments of the present invention.

DETAILED DESCRIPTION

Figure 1:
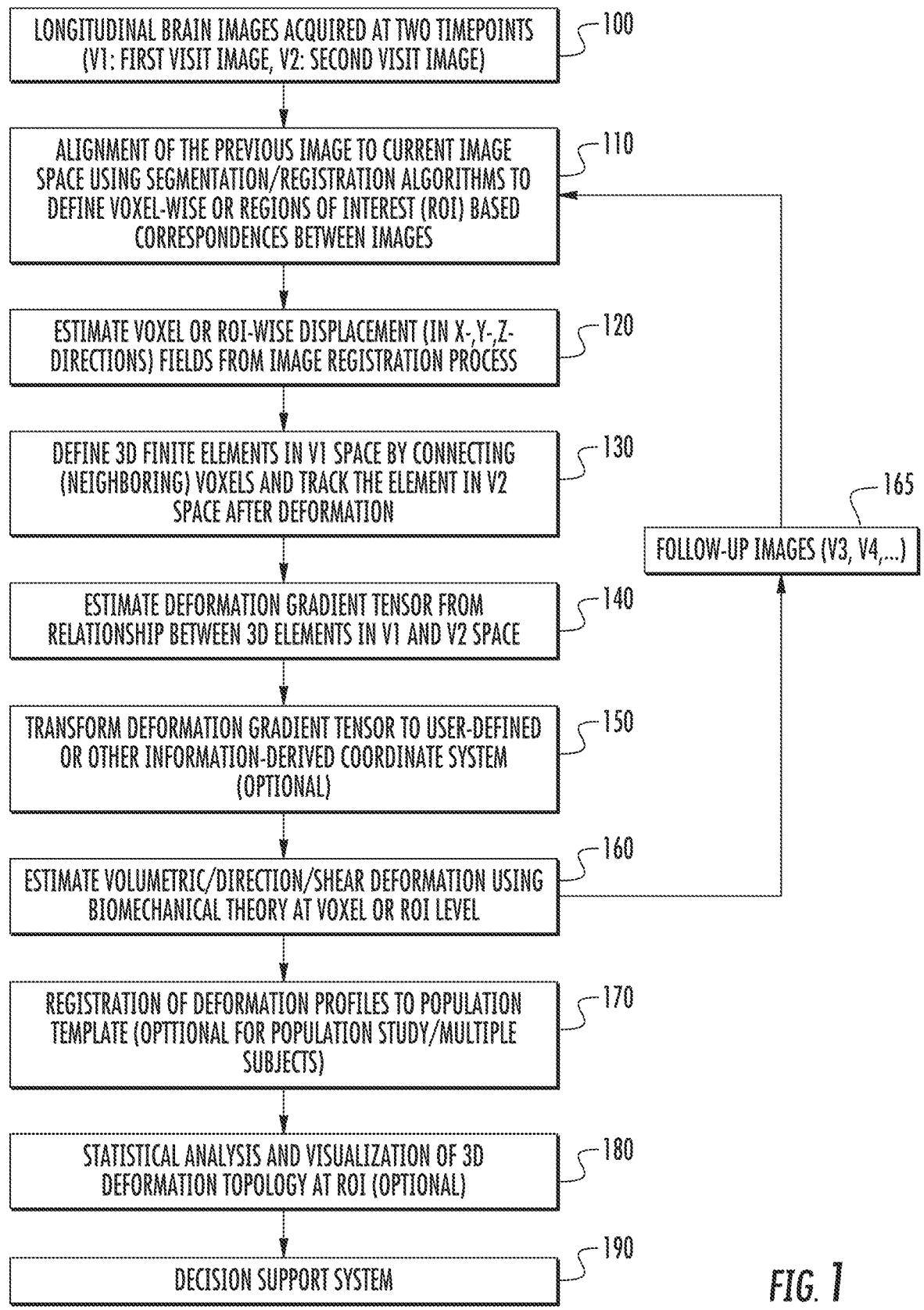
FIG. 1 is an exemplary flow chart of operations that can be carried out to evaluate medical images according to embodiments of the present invention.
Figure 2:
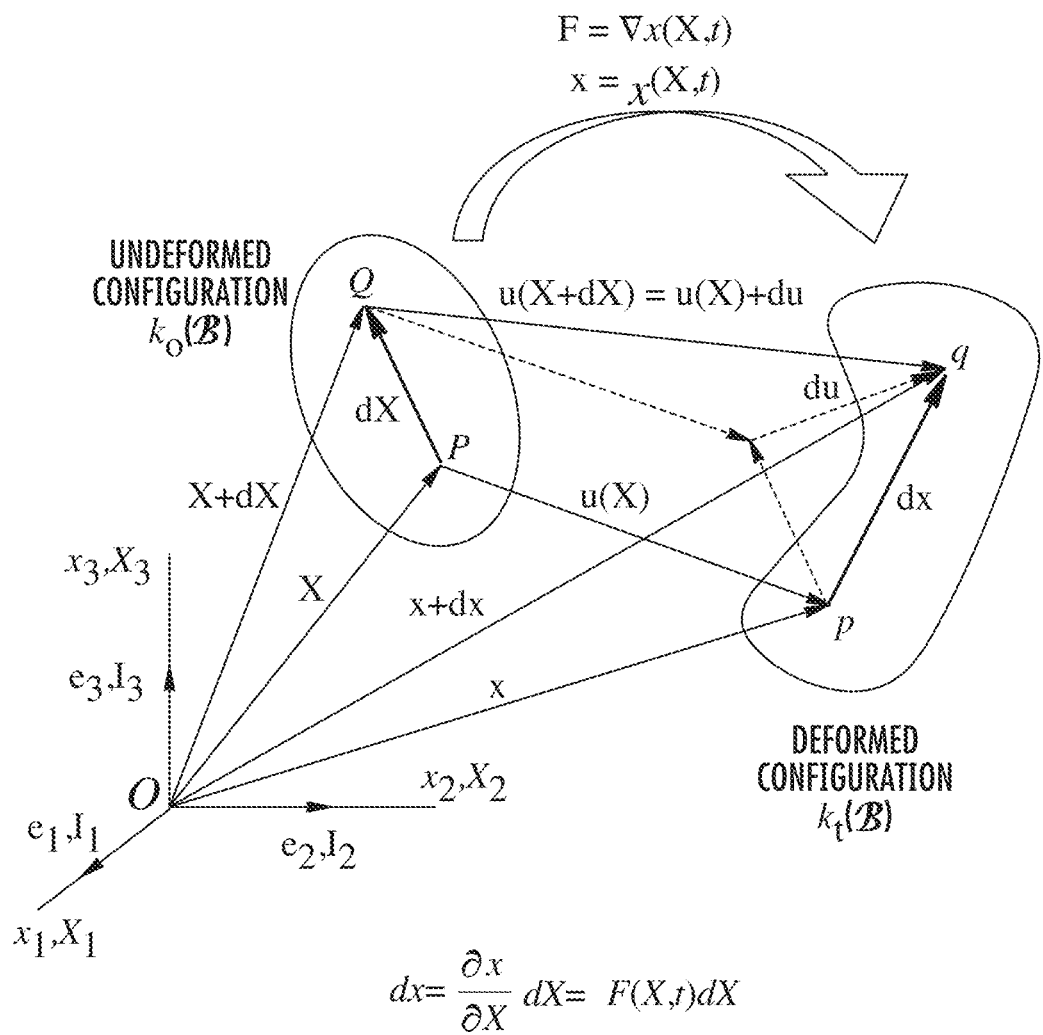
FIG. 2 is a schematic illustration of a finite strain theory that can be used to evaluate medical images according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. The terms "FIG." and "Fig." are used interchangeably as abbreviations of the word "Figure".

In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

The terminology used herein is for the purpose of describing particular embodiments only and is not intended to be limiting of the invention. As used herein, the singular forms "a", "an" and "the" are intended to include the plural forms as well, unless the context clearly indicates otherwise (i.e. at least one) of the grammatical object of the article. By way of example, "an element" means at least one element and can include more than one element.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various actions, steps or components and should not be limited by these terms. These terms are only used to distinguish one action, step or component from another action, step or component. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Embodiments of the present invention may take the form of an entirely software embodiment or an embodiment combining software and hardware aspects, all generally referred to herein as a "circuit" or "module." Thus, the terms "circuit" and "module" refer to an entirely software embodiment or an embodiment combining software and hardware aspects, features and/or components (including, for example, a server and/or at least one processor and software associated therewith embedded therein and/or executable by, for programmatically directing and/or performing certain described actions or method steps).

The term "programmatically" means that the operation or step can be directed and/or carried out by a digital signal processor and/or computer program code. Similarly, the term "electronically" with respect to the method of operation means that the step or operation can be carried out in an automated manner using electronic components rather than manually or using mental steps and includes wireless and wired connections between components.

The image analysis can be suitable for evaluating soft tissue medical images obtained from a number of different imaging modalities including, without limitation, MRI, CT (computed tomography), PET, fluoroscopy, and ultrasound.

The terms "MRI scanner" or MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5T/3.0T; Philips Medical Systems: Achieva 1.5T/3.0T; Integra 1.5T; Siemens: MAGNETOM Avanto; MAGNETOM Espree; MAGNETOM Symphony; MAGNETOM Trio; and MAGNETOM Verio. As is well known, the MR scanner can include a main operating/control system that is housed in one or more cabinets that reside in an MR control room while the MRI magnet resides in the MR scan room. The control room and scan room can be referred to as an MR suite and the two rooms can be separated by an RF shield wall. The term "high-magnetic field" refers to field strengths above about 0.5 T, typically above 1.0T, and more typically between about 1.5T and 10T. Embodiments of the invention may be particularly suitable for 1.5T, 2.0T and 3.0T systems, or higher field systems such as future contemplated systems at 4.0T, 5.0T, 6.0T, 7.0T, 9T and the like. The MR Scanners can be open bore or closed bore systems.

The term "longitudinal" with respect to the images means one image or set of images for a respective subject is obtained before another one image or sets of images.

The methods, circuits and systems can be used for any subject including animals and humans. The animal use can be for veterinarian or research purposes.

The term "automatically" and derivatives thereof means that the operation and/or method can be substantially, and typically entirely, carried out without manual input, and is typically programmatically directed and/or carried out.

The term "clinician" means physician, neurologist, radiologist, physicist, or other medical personnel desiring to review medical data of a patient. The term "workstation" refers to a display and/or computer associated with a clinician.

The term "about" refers to a parameter that can vary from the recite value, typically between +/−20%.

Embodiments of the invention use strain measurements to evaluate tissue change over time. While Lagrange strain measurements (deformation gradient tensors) are described herein as particularly suitable for such evaluations, other strain measures may be used, such as, by way of example and without limitation, Hencky strain, Almansi strain, Engineering strain, Eulerian strain, Murnaghan strain and Biot strain.

Each article, reference and patent cited or discussed herein is hereby incorporated by reference as if recited in full herein.

The medical image evaluations can be carried out post-acquisition (and typically, electronic storage of medical images in a hospital database patient record system and/or PACS (picture archiving and communication hospital/medical system) of at least a source or reference image(s)) and subsequent evaluation of the medical images optionally with renderings of parameter maps and/or visualizations using image data of first and second images of a subject taken, typically images taken at two different points in time.

It is noted, for clarity, that while certain of the figures are visualizations presented in "color" or "color-coded" or "color-encoded", these terms refer to a defined unique color or color scale of voxels correlated to a calculation of direction and/or stretch or shrink of voxel or voxels between two images of the same region of interest (ROI) of a respective subject. The visualizations can be provided as a plurality of different color maps, typically topology maps for different directional components. The term "topology" refers to a physical map of the ROI generated using calculated three-dimensional changes in voxel shapes, color coded to indicate, no change, an increase or a decrease of a size of respective voxels. Also, to comply with filing rules, black and white copies or grey scale versions of these images may be used in support of the application.

Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on an imaging system (such as an MR Scanner) computer/processor(s), partly on the imaging system (such as an MR Scanner) computer/processor(s), as a stand-alone software package, partly on the imaging system (such as an MR Scanner) computer/processor(s) and partly on another computer and/or server, local or remote or entirely on the other local or remote computer and/or server. In the latter scenario, the other local or remote computer and/or server may be connected to the imaging system (such as an MR Scanner) computer through a local area network (LAN) or a wide area network (WAN), or the connection may be made to an external computer (for example, through the Internet using an Internet Service Provider). Firewalls may be used for security and to comply with medical record privacy laws such as the Health Insurance Portability and Accountability Act of 1996 (HIPAA).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

In the past, Lepore et al. proposed deriving deformation tensor (a "Jacobian" matrix) from image registration algorithm. See, Lepore et al., Generalized Tensor-Based Morphometry of HIV/AIDS Using Multi-Variate Statistics on Deformation Tensors, IEEE Transactions on Medical Imaging, Vol. 27, No. 1, January 2008. However, this methodology divides deformation tensor into a stretching part and a rotation part (called a decomposition approach). This approach describes the deformation as a combination of directional change and rotation that occur consequently and may be descriptively termed a "1-D" evaluation. However, this approach is not believed to be physically realistic because biological growth/degeneration processes are not simply a combination these two processes.

Generally stated, embodiments of the present invention provide image analyses that generate three dimensional (3-D) finite elements in a first image view and/or space, with each 3-D finite element represented by linear connections of a plurality of neighboring voxel positions. Then, a respective 3D element's deformation in a second image view and/or space of a second image taken at a different time can be evaluated to estimate the directional/shear changes of the finite element(s). The new approach employs shear strain instead of rotation and is believed to better model how a 3-D element defined in an original configuration changes with time, which is more physically/biologically reasonable. Additionally, the new approach can detect and visualize 3D deformation with/without volumetric changes in a respective ROI and quantitatively relate directional/shear deformation to volumetric changes. Also, the 3-D finite element approach connects neighboring voxels for line segments that can change in angle and length. Thus, the analysis can identify orientation specific changes as well as provide directional and shear measurements of change.

A volumetric ROI can be modeled as a combination of several line elements. Three-dimensional deformation processes can be tracked through each line element and a new volumetric ROI can be reconstructed in a deformed configuration by applying finite strain theory.

Referring now to FIG. 1, an example analysis method is shown. Longitudinal brain images are acquired at two different time points (V1: first visit image, V2: second visit image) (block 100).

The previous ROI image is aligned to a current ROI image space using image segmentation/registration algorithms to define voxel-wise or regions of interest (ROI) based correspondences between images (block 110). An exemplary registration method is Advanced Normalization Tools, ANTs; Avants, B. B., Epstein, C. L., Grossman, M. & Gee, J. C. Symmetric diffeomorphic image registration with cross-correlation: evaluating automated labeling of elderly and neurodegenerative brain. Med Image Anal. 12, 26-41 (2008), the contents of which are hereby incorporated by reference as if recited in full herein.

Voxel or ROI-wise displacement (in x-,y-,z-directions) fields are estimated from image registration process (block 120). Image registration is an image processing technique to transform different sets of data to a common coordinate system. Open source-based non-linear image registration algorithms (Advanced Normalization Tools, ANTs and FMRIB Software Library) define voxel-wise displacement to align source image (V1) to reference coordinate system (V2). The movement of each voxel can be represented by a vector in 3D space, which comprises a deformation field or displacement fields for a certain ROI.

3-D finite elements in V1 space are defined by connecting adjacent or closely spaced apart neighboring voxels and tracking the respective elements in V2 space after deformation (block 130). The word "tracking" means electronically identifying the positions of the connected voxels of the 3-D finite elements based on deformation fields derived from image registration. The voxels are not required to be directly neighboring voxels and can be provided in other patterns but one voxel is usually within between 2-4 adjacent voxel positions.

A deformation gradient tensor (a gradient tensor applied post deformation) is estimated from the relationship between corresponding 3D elements in V1 and V2 space (block 140). However, other strain measurements using the 3D elements may be used as discussed above, with or without a gradient tensor.

The deformation gradient tensor can be transformed to a user-selected, defined or default (information-derived) coordinate system (optional)(block 150). This may comprise a DTI-derived coordinate system using Eigen vectors and/or other fiber direction specific coordinate system.

One or more of a volumetric, directional and/or shear deformation can be mathematically estimated/calculated using a biomechanical theory at a voxel or ROI level (block 160). See, for example, FIGS. 2, 3A, 5 and 6.

The deformation profiles can be registered and compared to a population norm template (optional for population study/multiple subjects) (block 170).

A statistical analysis can be performed by aligning single subject's deformation information to the averaged anatomical image or subject's representative image (V1 or V2) and visualizations of 3-D deformation topology of the ROI can be generated using the averaged deformation information across multiple subjects (optional) (block 180).

The information can be provided to a decision support system (block 190).

Additional images can be evaluated for monitoring or further follow-up evaluation using additional longitudinal images (V3, V4, . . . ) (block 165).

Figure 3A:
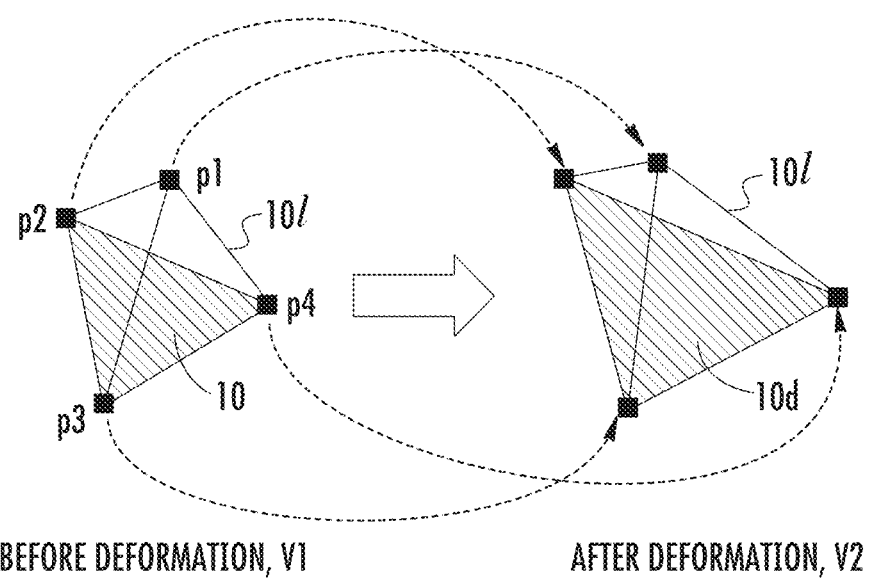
FIG. 3A is a schematic illustration of an exemplary three dimensional finite element defined by lines connecting positions of a plurality of voxels in a medical image according to embodiments of the present invention.
Figure 3B:
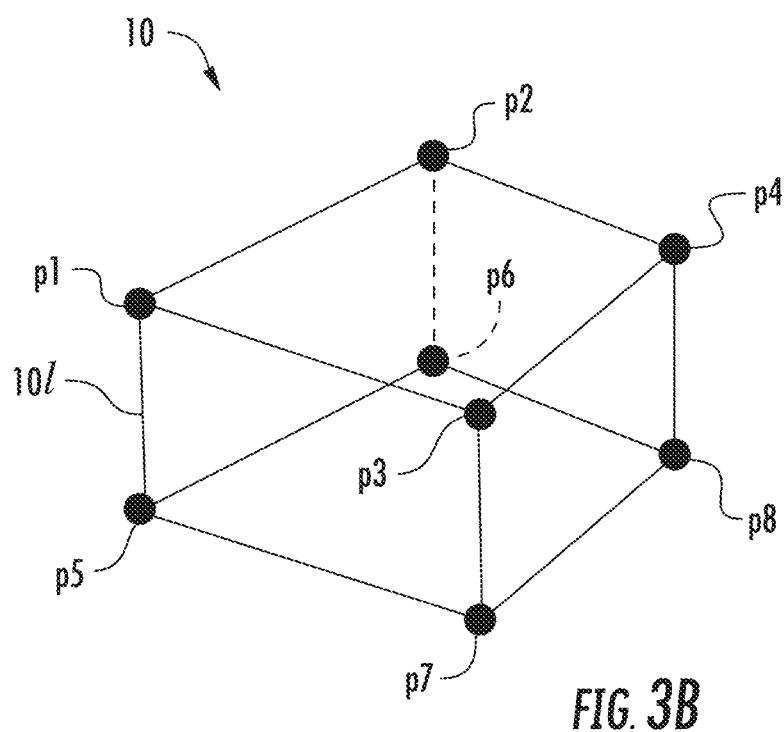
FIG. 3B is a schematic illustration of another exemplary shape of a 3-D finite element connecting voxels according to embodiments of the present invention.

With respect to the 3-D elements (block 130), as schematically illustrated in FIG. 3A, to define a three dimensional (3-D) element in a first image space ("V1" space), at least four different voxels with respective voxel positions are identified, p1, p2, p3, and p4. By connecting p1, p2, p3, p4, a 3-D finite element 10 is defined (shown as a tetrahedron), but other 3-D shapes can be also used with other numbers of voxel position points (i.e., vertices), such as a cube-shaped element by connecting 8 voxel positions, p1-p8 (FIG. 3B). This finite element 10 can be tracked and its deformation 10d can be used to evaluate shape change in three dimensions in a second image view V2. Each line 101 of the finite element 10 can independently and/or simultaneously change in length and orientation (i.e., angle) in the deformed configuration from the first view to the second view V1, V2.

Figure 4A:
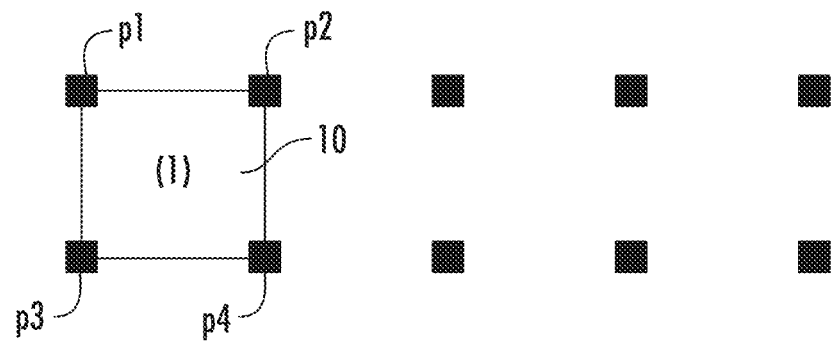
FIG. 4A is a schematic illustration of a 3-D finite element with lines connecting neighboring voxels according to embodiments of the present invention.
Figure 4B:
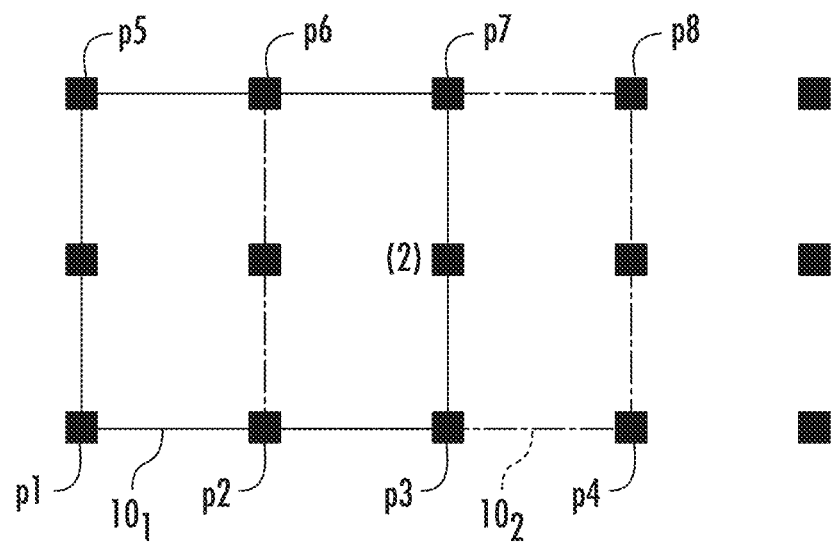
FIG. 4B is a schematic illustration of 3-D finite elements with overlapping regions according to embodiments of the present invention.

FIG. 4A illustrates that the voxels for the voxel positions (i.e., p1-p4) for a respective finite element 10 can be non-overlapping neighboring voxels. FIG. 4B illustrates that the 3-D finite elements 10 can use adjacent finite elements $10_1$, $10_2$ that have some overlapping regions (i.e., a "staggered pattern" of finite elements). Shown by way of example, a first finite element $10_1$ has voxels at voxel positions p1, p3, p5 and p7, while the second finite element $10_2$ has voxels at voxel positions p2, p4, p6 and p8. Using directly neighboring voxels for finite elements 10 may take advantage of high resolution images. However, the neighboring voxels can be indirect neighbors, typically within 2-4 adjacent voxels of each other, which may be useful to compare with relatively low resolution images (co-registration) or for other purposes. Also, the use of some overlapping patterns of finite elements 10 may provide analysis stability or reliability.

In some embodiments, evaluation of clustering patterns may be used, which may be a type of data-driven ROI. Statistically significant regions can be across two or more anatomically defined ROIs and if so, a cluster-based approach may be useful.

Figure 5:
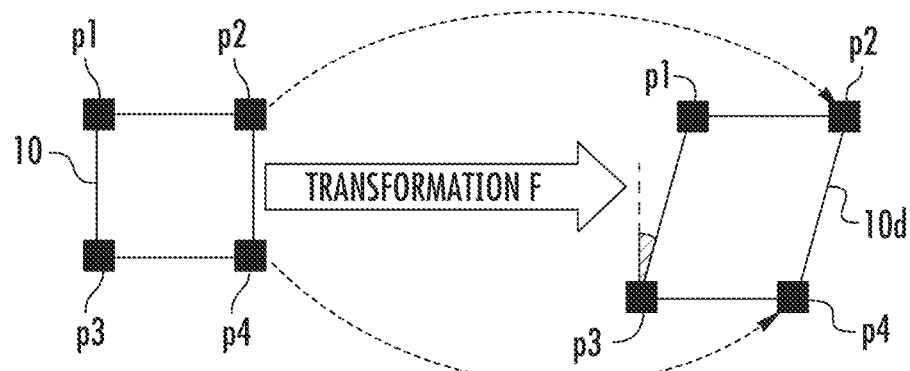
FIG. 5 is a schematic illustration of a finite strain theory for identifying directional, shear and volumetric changes according to embodiments of the present invention.
Figure 6:
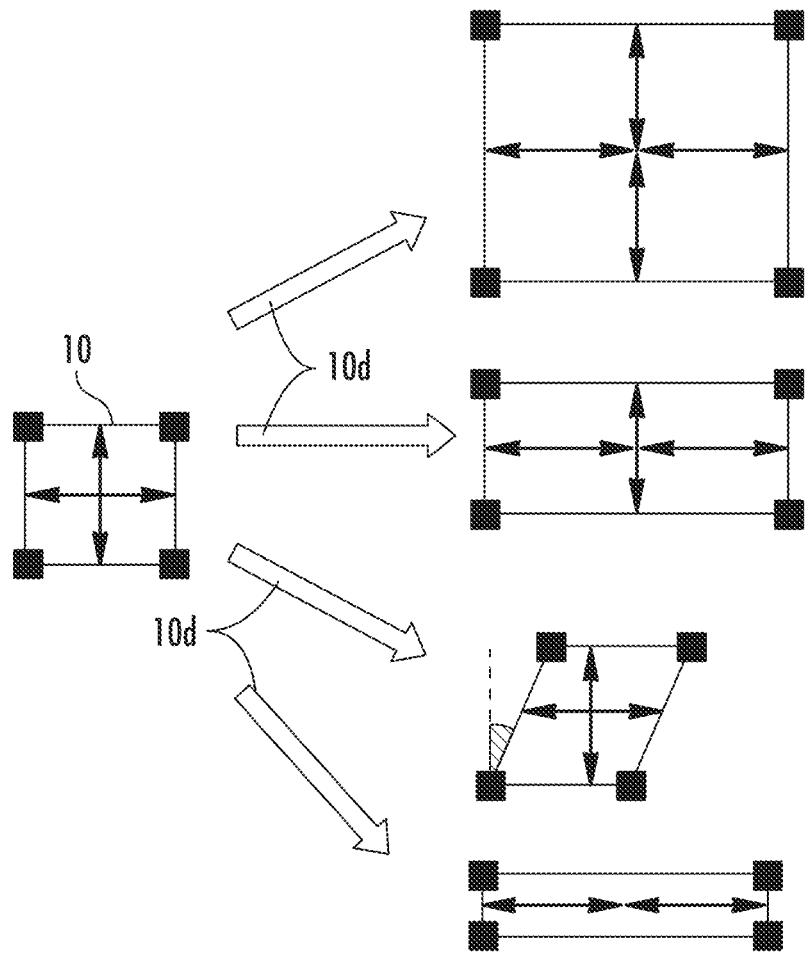
FIG. 6 is a schematic illustration of a detection of morphological changes over time or across the subjects in different medical images according to embodiments of the present invention.

Referring to FIGS. 5 and 6, the deformation gradient F is a fundamental measure of deformation in continuum mechanics. It can be the second order tensor which maps line elements in the reference configuration 10 to the one in the current configuration 10d. In image registration, 3D deformation fields describe the voxel-wise displacements of each direction in a (i.e., Cartesian) coordinate system and through which deformation gradient tensor is defined by relating undeformed configuration (X coordinate) to a deformed configuration (X coordinate):

$$F = \frac{\partial x_i}{\partial X_j} = \begin{bmatrix} \frac{\partial x_1}{\partial X_1} & \frac{\partial x_1}{\partial X_2} & \frac{\partial x_1}{\partial X_3} \\ \frac{\partial x_2}{\partial X_1} & \frac{\partial x_2}{\partial X_2} & \frac{\partial x_2}{\partial X_3} \\ \frac{\partial x_3}{\partial X_1} & \frac{\partial x_3}{\partial X_2} & \frac{\partial x_3}{\partial X_3} \end{bmatrix}, i, j = 1, 2, 3 \quad \text{Equation (1)}$$

JD describes the volume change ratio between undeformed and deformed configurations: JD=det(F).

JD>1.0 represents volumetric expansion, whereas JD<1.0 indicates volumetric contraction.

In continuum mechanics, one common choice for representing large strains between two different configurations is the Lagrange strain because it contains derivatives of the displacements with respect to the original configuration and can be conjugated with second Piola-Kirchhoff stress when the mechanical properties of material are known. Lagrange strain tensor is symmetric and describes directionally normal (diagonal components) and shear (off-diagonal components) strains:

$$E = \frac{1}{2}(F^T \cdot F - I) = \begin{bmatrix} E_{xx} & E_{xy} & E_{xz} \\ E_{yx} & E_{yy} & E_{yz} \\ E_{zx} & E_{zy} & E_{zz} \end{bmatrix} \quad \text{Equation (2)}$$

Where I is a 3×3 identity matrix. When Lagrange strain E operates on a line element dX, it gives the changes in the squares of the undeformed (dX) and deformed length (dx):

$$\frac{|dx|^2 - |dX|^2}{2} \equiv dXEdX \quad \text{Equation (3)}$$

The eigenvalues of E are related to directional stretch (λ). When unit extension is defined as $(|dx_i|-|dX_i|)/|dX_i|=\lambda_i-1$, denoting the unit extension of $dX_i$ by the normal strain, $e_i$ in the direction $I_i$, diagonal components of Lagrange strain are related to the normal strain; $E_{ii}=e_i+\frac{1}{2}e_i^2$. Positive values of Lagrange strain indicate stretch of a line element after deformation and vice versa. From the relationship between $E_{ii}$ and $\lambda_i$, anisotropy of directional growth rates (ADG) can be described using the concept of fractional anisotropy.

$$\lambda_i = \sqrt{2E_{ii}+1}, i=1, 2, 3 \quad \text{Equation (4)}$$

$$ADG = \sqrt{\frac{1}{2} \frac{\sqrt{(\lambda_1-\lambda_2)^2+(\lambda_2-\lambda_3)^2+(\lambda_3-\lambda_1)^2}}{\sqrt{\lambda_1^2+\lambda_2^2+\lambda_3^2}}} \quad \text{Equation (5)}$$

Off-diagonal components (shear strains) are symmetric and related to directional stretches and deformation angle, $\phi_{12}$:

$$E_{12} = \frac{1}{2}\sqrt{2E_{11}+1}\sqrt{2E_{22}+1}\sin\phi_{12} = E_{21}, \phi_{12} = \frac{\pi}{2}-\theta \quad \text{Equation (6A)}$$

where, θ is the angle between two line elements that are organically perpendicular. It is noted that Lagrange strain describes deformation based on the coordinate system of material particles before deformation. Also, as noted above other strain measurements may be used according to embodiments of the present invention. Equation 6A can be generalized as Equation 6B to represent the use of local coordinate systems.

$$E_{ij} = \frac{1}{2}\sqrt{2E_{ii}+1}\sqrt{2E_{ii}+1}\sin\phi_{ij} = E_{ji} \; \phi_{ij} = \frac{\pi}{2}-\theta \quad \text{Equation (6B)}$$

Figure 7:
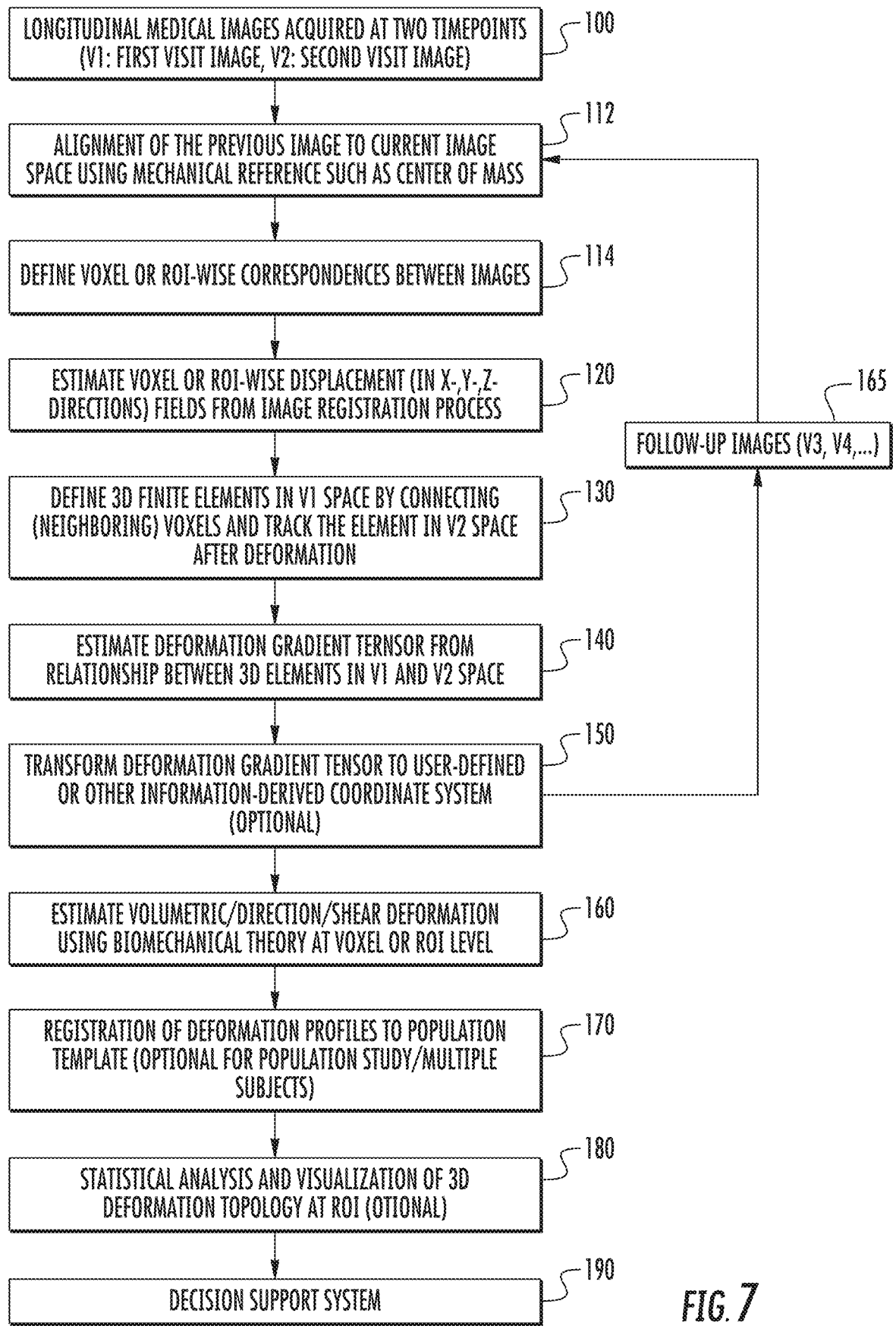
FIGS. 7, 8A and 8B are additional exemplary flow charts of operations that can be carried out to evaluate medical images according to embodiments of the present invention.
Figure 8A:
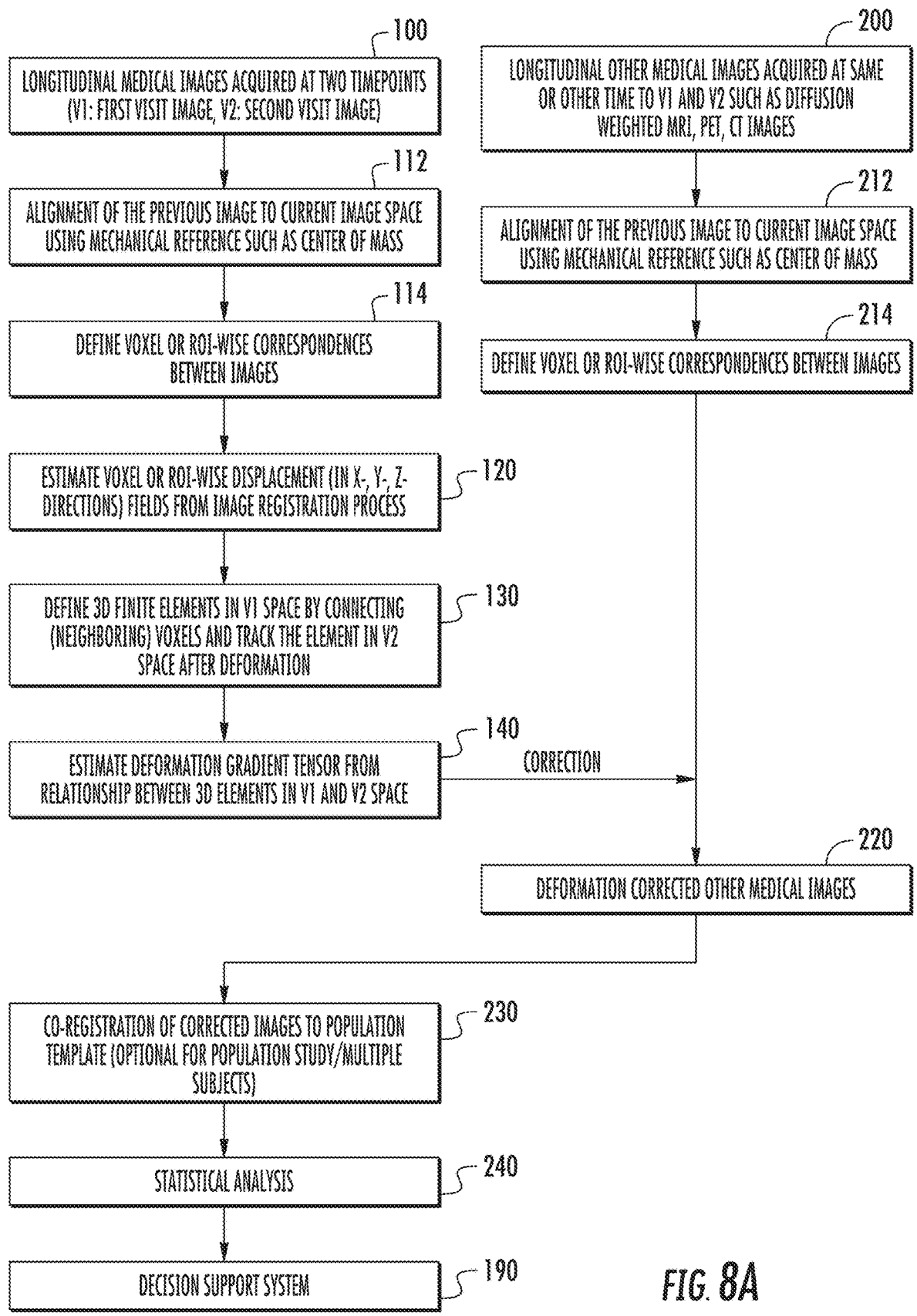
Figure 8B:
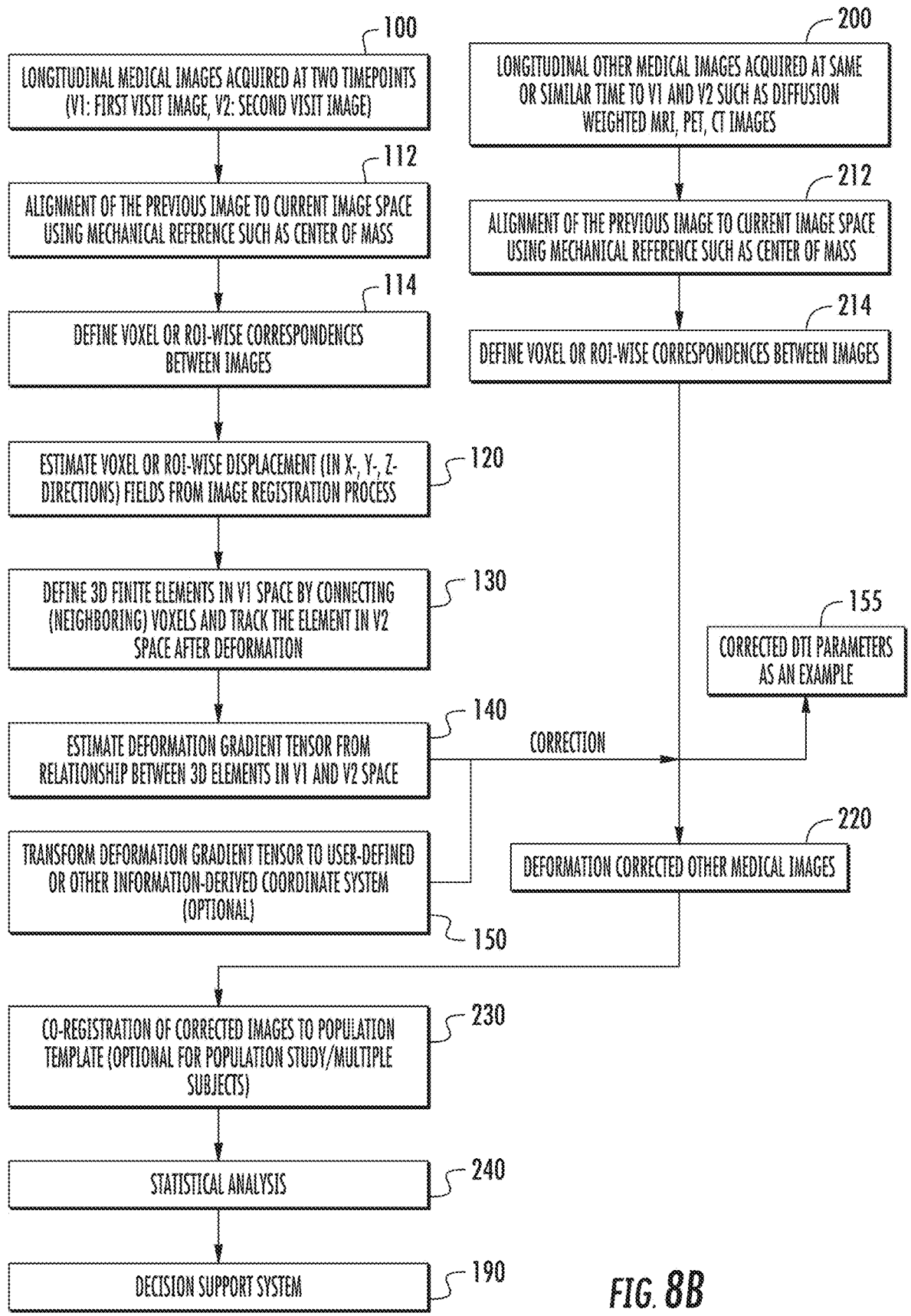

FIGS. 7 and 8A and 8B illustrate additional exemplary analysis methods, similar to that shown in FIG. 1, according to embodiments of the present invention. FIG. 7 illustrates that in lieu of segmentation/registration based alignments, a mechanical or physical alignment reference can be used such as, for example, a center of mass (block 112) and a voxel or ROI-wise correspondence can e defined (block 114) (Yoo, S. K. et al. Alignment of CT images of skull dysmorphology using anatomy-based perpendicular axes. *Phys Med Biol.* 48, 2681-2695 (2003), the contents of which are hereby incorporated by reference as if recited in full herein.

FIGS. 8A and 8B illustrate that the analysis methods can evaluate other types of medical images of the subject taken at the same time or different times (similar to V1 and V2 or at different time points) and the method can evaluate multiple images from multiple image modalities (block 200). Thus, other longitudinal medical images acquired at the same, similar or different time to V1 and V2. Examples of longitudinal images include T1-weighted (T1w) MRI, diffusion tensor (DTI) MRI, PET, and CT images. As an example, diffusion tensor images present diffusion characteristics in a certain direction. If the diffusion tensor images are collected similar or at the same time when the structural images used to derive the mechanical deformation information, the mechanical deformation can be used to correct the changes of directional diffusion characteristics over time. Another example is using the mechanical deformation information between V1 and V2 can be used to overcome low spatial resolution. Specifically diffusion weighted MRI and PET images typically have lower resolution than structural images and these images lose their original signal in small regions or around boundaries of tissues with different diffusion property or activity. If there is inhomogeneous deformation between two images at different time points, the shape of small ROI tissue boundaries change accordingly. For more accurate comparison, deformation corrected images using mechanical deformation from higher resolution images can be used. One of similar applications is partial volume correction in PET imaging (Meltzer, C. C. et al. Comparative evaluation of MR-based partial-volume correction schemes for PET. *J Nucl Med.* 40, 2053-2065 (1999)), the contents of which are hereby incorporated by reference herein. The previous image is aligned to a current image (or image space) using a mechanical reference such as center of mass (block 212). Voxel and/or ROI-wise correspondences between images are defined (block 214). The estimated deformation gradient tensor from the first two images, which may be from a common image modality, can be used to generate deformation corrected other medical images (block 220). The corrected images can be co-registered to a corresponding population template (optional for population study/multiple subjects) (block 230).

The deformation corrected images and the deformation images can be automatically electronically statistically analyzed for directional and shear change, for associated change patterns associated with biomarkers and the like (block 240).

FIG. 8B illustrates the deformation correction can be carried out using corrected DTI parameters (block 155) as will be discussed further below with respect to FIG. 15.

Figure 9:
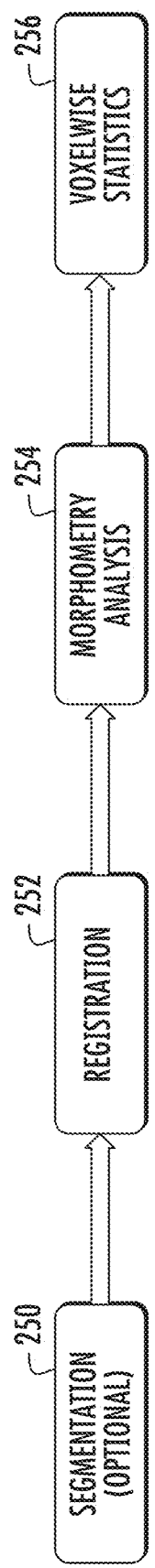
FIG. 9 is an example flow chart of an MRI analysis according to embodiments of the present invention.

FIG. 9 is an example MRI analysis method which illustrates T1w images are acquired at two different time points (which may be weeks, months or years apart) with optional segmentation and ANTS: tissue probability maps (block 250). Longitudinal registration is carried out within subject deformation fields (block 252). A morphometry analysis is electronically carried out (block 254) which can include deformation parameters, volumetric change as well as directional length change and may be aligned to a template. Voxel wise statistical review can be carried out (block 256) such as within group and group comparisons. Within group comparisons can include paired t-test, one sample t-test, log (JD) or log (1+E) and/or FDR correction. Group comparison can include linear regression, p-threshold=0.005), cluster size (such as 608 voxels) and α=0.05.

Figure 10:
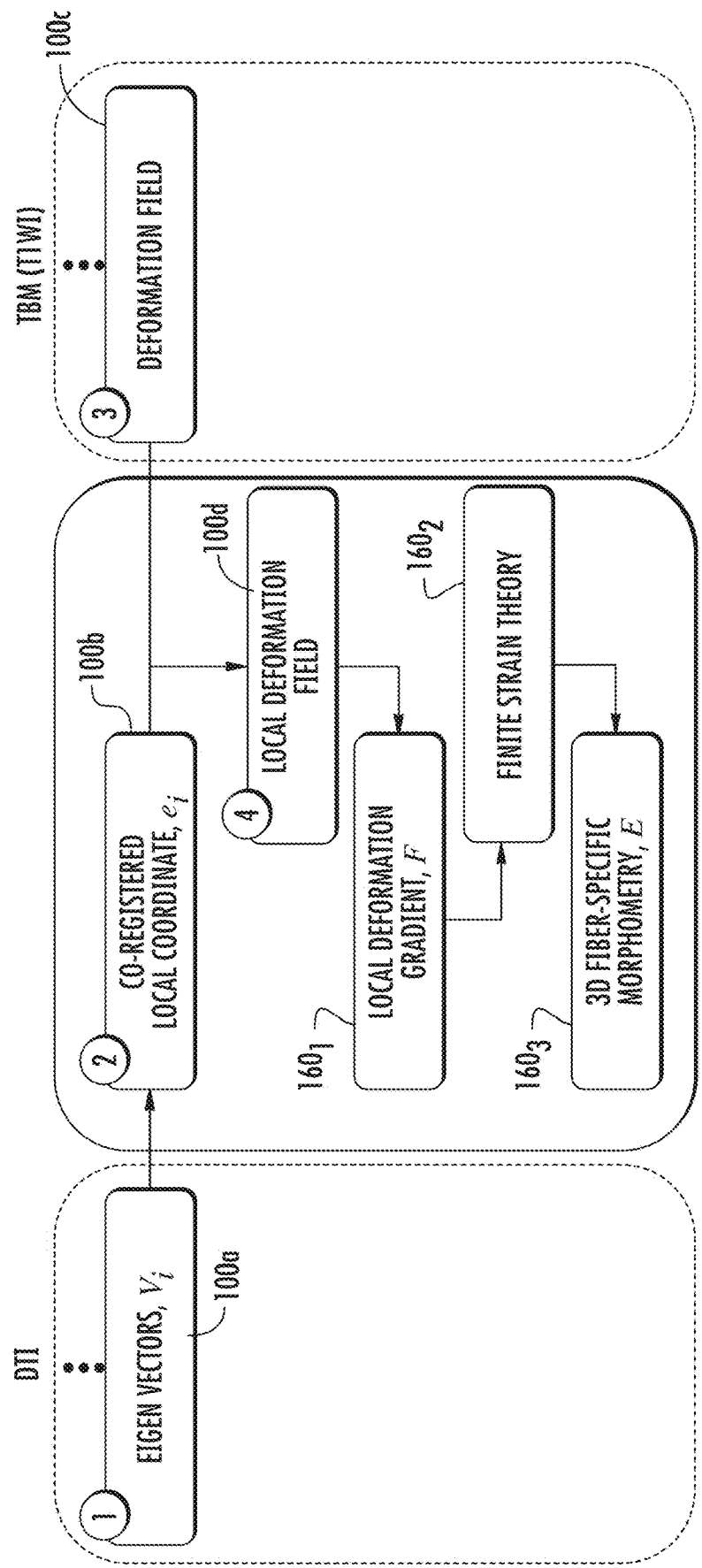
FIG. 10 is a block diagram of an example image analysis method that incorporates a local coordinate system according to embodiments of the present invention.

FIG. 10 is an example of a multi-image modality image analysis method using a local coordinate system derived from Eigen vectors $V_i$ acquired from diffusion tensor images (DTI) which can be described as a "user-defined" coordinate system (block 100a). Co-registered Eigen vectors can provide a voxel wise local coordinate system of co-registered/local coordinates $e_i$ to deformation fields defined in high resolution T1-weighted images (block 100b). A pair of longitudinal/cross-sectional images can be used to identify voxel wise three dimensional shape changes (block 100c). By combining 100b and 100c, local deformation fields for each voxel can be obtained (block 100d). Therefore, in white matter fiber tract, fiber orientation specific deformation measures (strain) E, i.e., 3D fiber-specific morphometry, can be derived (block $160_3$) using the local Deformation Gradient, F and finite strain theory (blocks $160_1$, $160_2$) as discussed above.

Figure 11A:
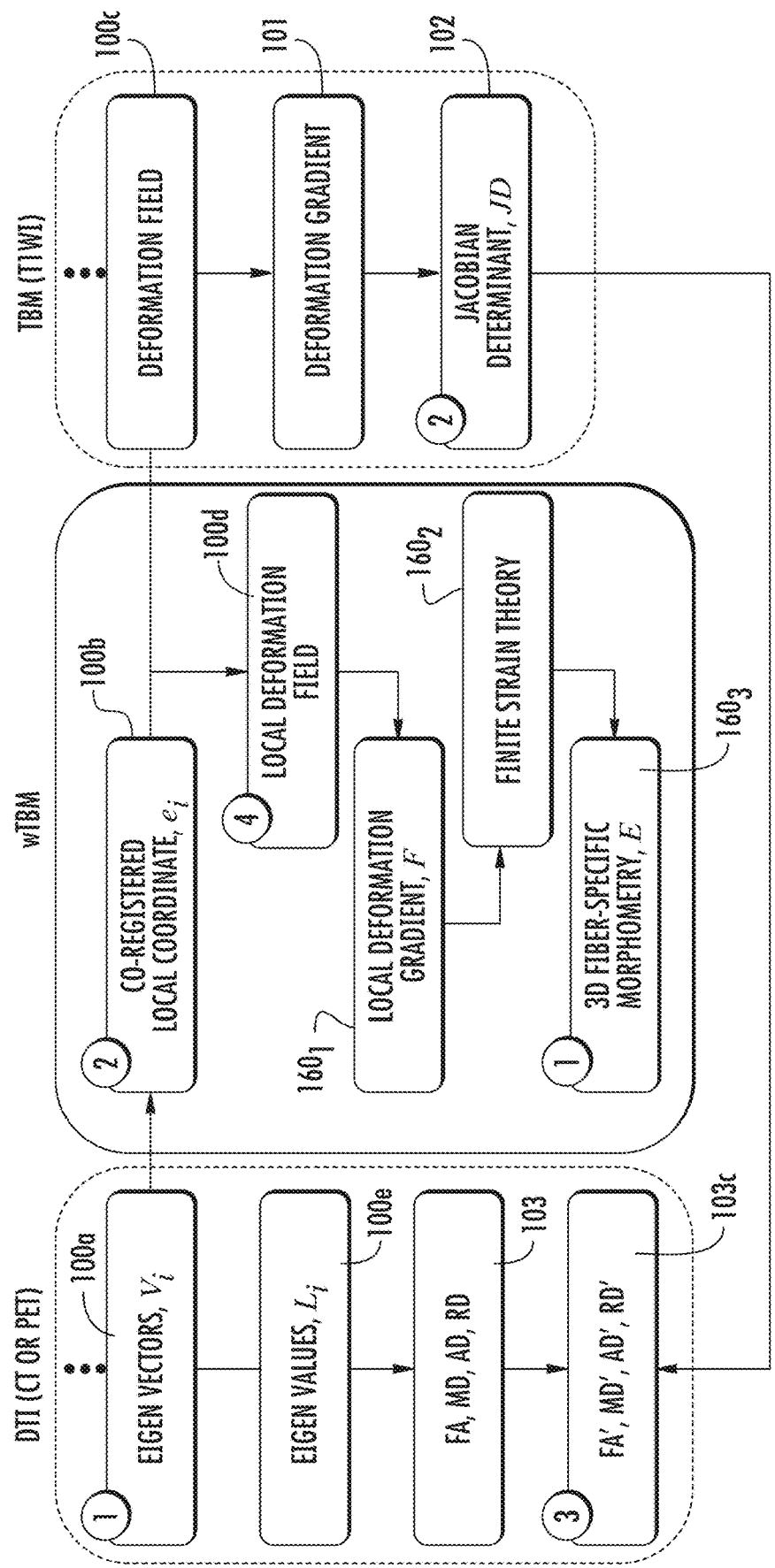
FIG. 11A is a block diagram of another example image analysis method that incorporates multiple image types and a local coordinate system (shown from DTI) using Eigen vectors according to embodiments of the present invention.

FIG. 11A is another example of a multi-image modality image analysis method similar to that shown in FIG. 10. This method illustrates an example of a medical image correction that can be carried out using morphometric information. By bridging local coordinate information from DTI and local deformation from TBM, 3D fiber tract-specific morphometry can be extracted by applying finite strain theory. Each voxel in an ROI can have different local coordinate system defined by co-registered Eigen vectors to T1WI.

Eigen values $L_i$ can be obtained (block 100e) from the Eigen vectors $V_i$ from the DTI (or other image type) and fractional anisotropy (FA), mean diffusivity (MD), axial diffusivity (AD), and radial diffusivity (RD) images can be generated (block 103). A deformation gradient can be applied to the T1WI using tensor based morphometry (TBM) images (block 101) and a Jacobian Determinant, JD can be obtained as a convectional volumetric biomarker (block 102). Corrected medical images FA', MD', AD', and RD' can be generated using the morphometric parameters (block 103c).

Figure 11B:
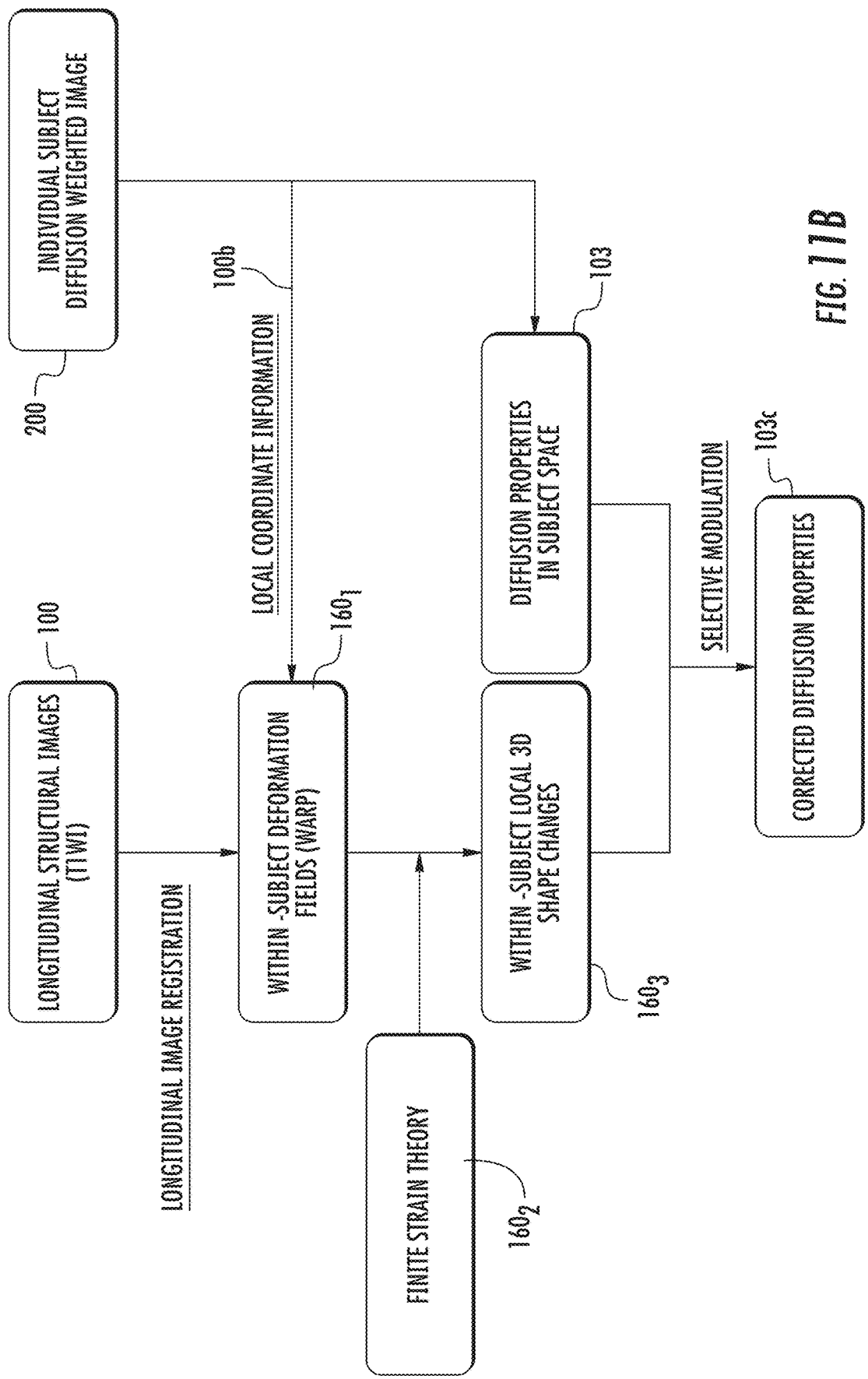
FIG. 11B is a block diagram of another example image analysis method that incorporates multiple image modality types and a local coordinate system that does not require/use a template according to embodiments of the present invention.
Figures 12, 13A, 13B:
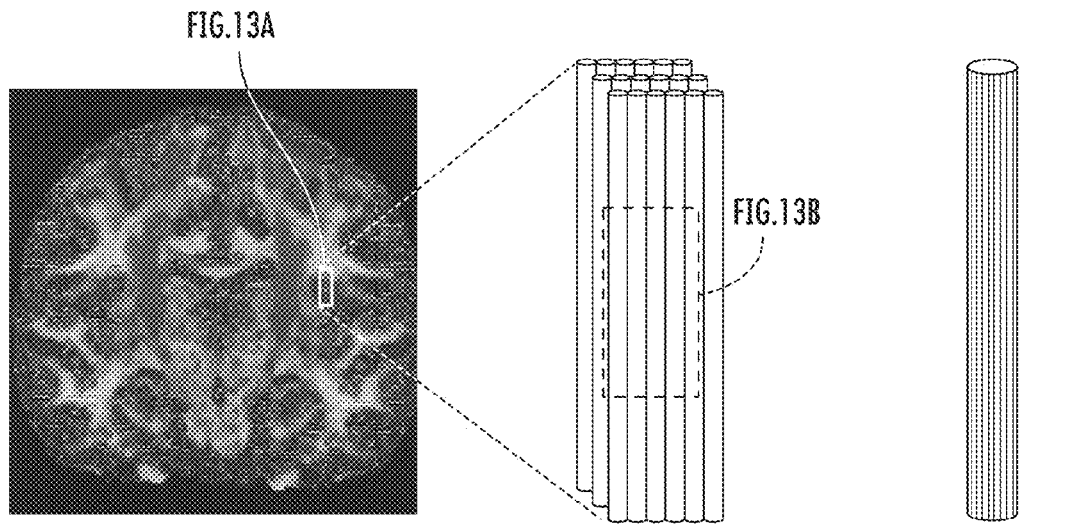
FIG. 12 is a visualization of a coronal brain image overlaid with (directionally color encoded) Eigen vectors in a principal direction according to embodiments of the present invention.
FIG. 13A is an example of a local (axonal) fiber bundle in white matter of the brain image of FIG. 12 according to embodiments of the present invention.
FIG. 13B is a schematic simplified representation of the fiber bundle of FIG. 13A according to embodiments of the present invention.

FIG. 11B illustrates another example of an image analysis method that does not require templates and uses multiple image types according to embodiments of the present invention. Fixel-based analysis ("FBA") (Raffelt et al., Investigating white matter fibre density and morphology using fixel-based analysis) is limited to a single modality of imaging, and diffusion-weighted imaging (DWI) and deformation fields (Warp) are estimated between the subject and template. In contrast, embodiments of the invention uses multi-modal images (e.g. T1-weighted image (T1WI) (block 100)+DWI (block 200) or T1WI (block 100)+surface normal vector image from surface-based morphometry (Vs, FIG. 15C) to integrate multi-modality information within a single subject space based on longitudinal images without requiring or using a template. Embodiments of the invention have interacting structure between different modality images: one provides (DWI) local coordinate information (100b) to the other modality image (T1WI), and then the estimated local shape change parameters (block 160$_3$) by finite strain theory (block 160$_2$) are used to correct the properties measured by the former image (DWI).

FBA estimates only fiber cross-section using deformation field and fiber direction derived from DWI, by simply dividing Jacobian Determinant (volume change ratio) by unit vector defining local fiber direction. In further contrast, embodiments of the invention can estimate six components of strain tensor by applying finite strain theory at user-defined coordinate system (e.g. local fiber coordinate or local surface normal coordinate), which can provide full 3-dimensional description of shape change such as each directional elongation, twisting and shearing of local 3D finite element. In this process, 3D finite element or ROI is re-defined at each local coordinate system by connecting a plurality of neighboring voxels to estimate local deformation fields and shape changes, which could demonstrate better anatomical correspondence.

FBA corrects diffusion properties (e.g. FD) by simply multiplying morphometric parameter (FC). Embodiments of the invention can correct diffusion property (DWI) or activity of radioisotopes (PET) by selectively combining 3D morphometric parameters considering pathology and different modality of imaging (e.g. only considering negative changes, tissue atrophy region).

The white matter (WM) of the brain is primarily composed of myelinated axons acting as a relay that coordinate communication between different functional regions. WM abnormalities are seen in a wide range of mental disorders, such as WM connectivity disruption in schizophrenia, as well as decreased fiber integrity as observed in cases of traumatic brain injury (TBI) and Alzheimer's disease (AD). Despite the importance of WM-related neuroimaging biomarkers in a wide range of brain diseases, conventional structural morphometry approaches have not thoroughly addressed WM tract-specific shape changes because of their focus on volumetric change of gray matter or fiber tractography. In reality, morphologic changes of WM are involved with more complex physical deformation patterns such as fiber elongation, pruning, fiber twisting, swelling, and volumetric expansion/contraction, which could affect microstructural tissue properties measured by diffusion tensor imaging (DTI). Diffusion tensor imaging (DTI) is a promising method for characterizing structural connectivity and three-dimensional water diffusion properties along/orthogonal to WM fiber direction, based on magnitude of the diffusion tensor. See, e.g., Le Bihan D, Mangin J F, Poupon C, Clark C A, Pappata S, Molko N, et al. Diffusion tensor imaging: concepts and applications. J Magn Reson Imaging. 2001; 13(4):534-46. PubMed PMID: 11276097, the contents of which are hereby incorporated by reference as if recited in full herein.

T1-weighted imaging (T1WI) is the one of the basic imaging sequences in MRI and demonstrates different contrasts among brain tissues as shown by T1 relaxation time. In medical image processing, T1WI is typically used to find anatomical correspondences between two longitudinal images. Their structural differences can then be identified in high-resolution space using tensor-based morphometry (TBM) methods. See, e.g., Ashburner J, Friston K J. Voxel-based morphometry—the methods. Neuroimage. 2000; 11(6 Pt 1):805-21. doi: 10.1006/nimg.2000.0582. PubMed PMID: 10860804; and Ashburner J, Friston K J. Morphometry. In: R. S. J. Frackowiak K J F, C. Frith, R. Dolan, K. J. Friston, C. J. Price, S. Zeki, J. Ashburner, and W. D. Penny, editor. Human Brain Function. 2nd edition ed: Academic Press; 2003, the contents of which are hereby incorporated by reference as if recited in full herein.

A previous study proposed a generalized TBM approach that extends the standard approach by applying multivariate statistics on the full deformation tensors and capturing shape changes of the corpus callosum in a Cartesian coordinate system. See, e.g., Lepore N, Brun C, Chou Y Y, Chiang M C, Dutton R A, Hayashi K M, et al. Generalized tensor-based morphometry of HIV/AIDS using multivariate statistics on deformation tensors. IEEE Trans Med Imaging. 2008; 27(1):129-41. doi: 10.1109/TMI.2007.906091. PubMed PMID: 18270068; PubMed Central PMCID: PMCPMC2832297, the content of which is hereby incorporated by reference as if recited in full herein. However, the multivariate approach in a Cartesian coordinate system that is not relevant to fiber structure can make it difficult to interpret the detected abnormalities in anatomically intuitive terms.

Other studies analyzed WM morphometry using diffusion weighted images (DWI) and proposed morphologic changes of fiber structure in terms of volume, fiber cross-sectional area, and tract thickness. However, these studies only addressed fiber morphometry as a single numerical summary in a low-resolution image space of DWI, and DWI-based image registration may lose real geometric information in some areas of the brain due to artifacts in the vicinity of air cavities (e.g. nasal sinuses). See, e.g., Bammer R. Basic principles of diffusion-weighted imaging. Eur J Radiol. 2003; 45(3):169-84. PubMed PMID: 12595101, the content of which is hereby incorporated by reference herein.

It is believed to be important and perhaps even critical to describe full fiber structure deformation in 3D in a high-resolution T1WI space to detect subtle changes of brain tissue. Therefore, to provide this more complete description of WM fiber structural changes, the fiber orientation information can be combined with three-dimensional deformation in high resolution space by using finite strain theory according to embodiments of the present invention, to explain different physics along and orthogonal to fiber orientation and fiber twisting. Diffusion weighted spin-echo MR imaging techniques can allow for accurate co-registration between T1WI and DTI, with simultaneous correction of geometric distortion and eddy current. See e.g., Andersson J L, Skare S, Ashburner J. How to correct susceptibility distortions in spin-echo echo-planar images: application to diffusion tensor imaging. Neuroimage. 2003; 20(2):870-88. doi: 10.1016/S1053-8119(03)00336-7. PubMed PMID: 14568458; and Greve D N, Fischl B. Accurate and robust brain image alignment using boundary-based registration. Neuroimage. 2009; 48(1):63-72. doi: 10.1016/j.neuroimage.2009.06.060. PubMed PMID: 19573611; PubMed Central PMCID: PMCPMC2733527, the contents of which are hereby incorporated by reference herein.

Although TBM and DTI approaches provide valuable insights into WM properties, some drawbacks in structural morphometry analysis of WM remain. In TBM, volumetric change maps represented by Jacobean Determinant (JD) are fuzzy at the individual level and may not reflect anisotropic shape changes of WM that possibly occur with the specific orientation of fibers. On the other hand, DTI metrics explain the microstructural properties of WM, but during the tract/tensor-based normalization process, they eliminate morphologic information related to differences in brain size and shape. This lack of integration between morphometry and diffusion-based measures of microstructural integrity may lead to the loss of anatomy/pathology-specific information in WM, thus limiting the robustness of these imaging biomarkers.

In reality, morphologic changes of WM are involved with complex physical deformation processes such as directional elongation, shearing, fragmentation, fiber twisting, crossing, swelling, fiber bending and volumetric expansion and contraction, all of which could affect microstructural tissue properties measured by DTI alone. Thus, embodiments of the present invention are directed at morphometry analyses that combine different MRI sequences to analyze a biomechanical framework.

Figures 13C, 13D, 13E, 13F:
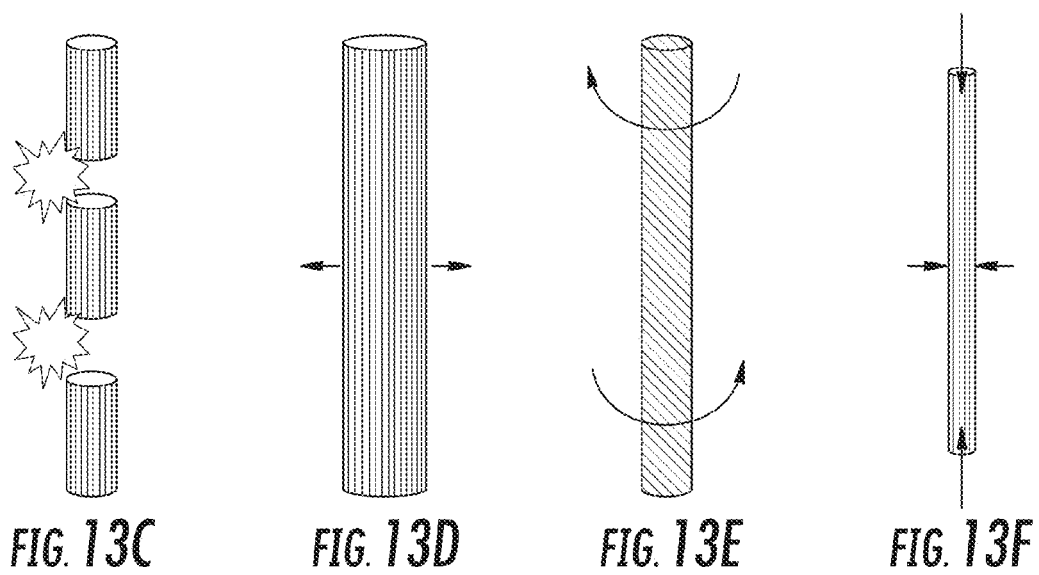
FIGS. 13C-13F are schematic illustrations of example deformations that the fiber bundle may have in white matter according to embodiments of the present invention.

FIGS. 13A-13F schematically illustrate possible deformation scenarios of axonal fiber bundle structures in the brain white matter. FIG. 12 is a coronal image of the brain overlaid with color-coded Eigen vectors Vi in the principal direction (V1). The color-coding of Eigen vectors in FIG. 12 can use three different colors, in some embodiments red represents fibers direction in Left-to-Right direction, green represents fiber in Anterior-to-Posterior direction and blue represents fiber in Inferior-to-Superior direction). Assuming each voxel in the MR image reflects physical properties of local fiber bundles (FIG. 13A), a respective fiber bundle can be represented as a cylinder-shaped element (FIG. 13B), which can be deformed to different shapes involved with fiber pruning/fragmentation (FIG. 13C), swelling/thinning (FIG. 13D), twisting (FIG. 13E), or volumetric expansion/contraction (FIG. 13F).

Figure 14:
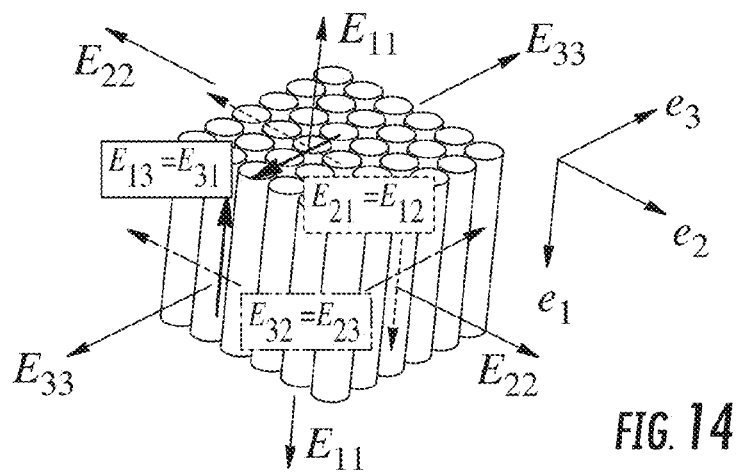
FIG. 14 is a schematic illustration of a local fiber-specific coordinate system defined by Eigen vectors for estimating shear stain related to fiber twisting and bending, for example, according to embodiments of the present invention.

FIG. 14 is a schematic illustration of Lagrangian strain tensor components in a local fiber-specific coordinate system defined by Eigen vectors. Shear strains in the three different colored rectangles and associated pairs of perpendicular arrows are symmetric and related to fiber twisting and bending.

As discussed above, methods of the present invention integrate multi-modal MR (or PET or CT) information using finite strain theory. To create a functional representation of the deformation field, a local coordinate system $\{e_1, e_2, e_3\}$ can be aligned with Eigen vectors co-registered onto the T1WI space.

$$F = \frac{\partial x_i}{\partial X_j} = \begin{bmatrix} \frac{\partial x_1}{\partial X_1} & \frac{\partial x_1}{\partial X_2} & \frac{\partial x_1}{\partial X_3} \\ \frac{\partial x_2}{\partial X_1} & \frac{\partial x_2}{\partial X_2} & \frac{\partial x_2}{\partial X_3} \\ \frac{\partial x_3}{\partial X_1} & \frac{\partial x_3}{\partial X_2} & \frac{\partial x_3}{\partial X_3} \end{bmatrix} \quad \text{Equation (7)}$$

As discussed above with respect to Equation (1), the deformation gradient F, is the fundamental measure of deformation in continuum mechanics. In image registration, 3D deformation fields describe the voxel-wise displacements for each direction in a Cartesian coordinate system, with which a deformation gradient tensor is defined to relate source images (X coordinate) to reference images (X coordinate). Again, the Jacobian determinant, JD=det(F) describes volume change ratios between undeformed configuration and deformed configurations and JD>1.0 represents volumetric expansion, whereas JD<1.0 means volumetric contraction.

Deformation fields defined in a Cartesian coordinate system can be converted to a local fiber-specific coordinate system. As discussed above with respect to Equation (2), Lagrange strain can be used as a deformation measure because it contains derivatives of the displacements with respect to the original configuration, and can be conjugated with second Piola-Kirchhoff stress when the mechanical properties of material is known.

$$E = \frac{1}{2}(F^T \cdot F - I) = \begin{bmatrix} E_{11} & E_{12} & E_{13} \\ E_{21} & E_{22} & E_{23} \\ E_{31} & E_{32} & E_{33} \end{bmatrix} \quad \text{Equation (8)}$$

The Lagrangian strain tensor E is symmetric and describes directionally normal and shear strains to the local fiber structure as shown in FIG. 14. Where, I is a 3×3 identity matrix. The diagonal elements of E are related to directional stretch ($\lambda$). When unit extension is defined as $(|dx|-|dX|)/|dX|=\lambda-1$, denoting the unit extension of $dX_{(1)}$ by $E_{(1)}$, one has $E_{11}=E_{(1)}+\frac{1}{2}E_{(1)}^2$ and similarly for the other diagonal elements. Positive values of Lagrange strain indicate stretch of line element after deformation and vice versa. Off-diagonal elements of the strain tensor also have important physical meanings. The twisting and bending of fiber structure are related to shear strains, for example, $E_{23}=\frac{1}{2}\sqrt{2E_{22}+1}\sqrt{2E_{33}+1}\sin\phi_{23}$, where $\phi$ is deformation angle of fiber structure. This protocol can be applied to fiber crossing regions using Bayesian estimation of diffusion parameters obtained using sampling techniques, which will provide principal diffusion directions for crossing fibers. See, e.g., Behrens T E, Berg H J, Jbabdi S, Rushworth M F, Woolrich M W. Probabilistic diffusion tractography with multiple fibre orientations: What can we gain? Neuroimage. 2007; 34(1): 144-55. doi: 10.1016/j.neuroimage.2006.09.018. PubMed PMID: 17070705, the contents of which are hereby incorporated by reference as if recited in full herein.

It is contemplated that visualizations of diffusion patterns and classification of such patterns of complex morphologic changes of local WM fibers can be carried out by embodiments of the present invention. wTBM parameters may provide more reliable description of morphologic changes compared to either TBM or DTI applied independently. $E_{22}$ and $E_{33}$ can explain fiber swelling which may be associated with acute ischemia or cytotoxic edema. $E_{11}$ can be a strong descriptor of fiber length change during nerve degeneration or pruning during the development. Fiber twisting in diffuse axonal injury or increase in tortuosity associated with WM property change might be explained with off-diagonal elements of the strain tensor ($E_{12}$, $E_{23}$, and $E_{31}$).

Morphometry derived from T1WI that has mm-scale spatial resolution can reflect phenomena of axonal fibers in μm-scale. However, if T1WI imaging is not suitable for this purpose, as an alternative, DWI with high b-value (about 3000 s/mm$^2$ or more), which has relatively low resolution but is more sensitive to fiber orientation distribution may be used. Also or alternatively, other registration algorithms incorporating a full tensor component can be used as an alternative to address this issue. See, Keihaninejad S, Zhang H, Ryan N S, Malone I B, Modat M, Cardoso M J, et al. An unbiased longitudinal analysis framework for tracking white matter changes using diffusion tensor imaging with application to Alzheimer's disease. Neuroimage. 2013; 72:153-63. doi: 10.1016/j.neuroimage.2013.01.044. PubMed PMID: 23370057, the contents of which are hereby incorporated by reference as if recited in full herein.

Embodiments of the invention provide new fiber tract-specific morphometric parameters ($E_{11}$, $E_{22}$, $E_{33}$, $E_{12}$, $E_{23}$, and $E_{31}$) may improve the performance of longitudinal measures compared to conventional morphometry (JD) or DTI parameters such as fractional anisotropy (FA) and mean diffusivity (MD).

To test the clinical relevance of new morphometric parameters, a linear regression model (HIE or Cog~wTBM+ ΔDTI+ΔDTI*wTBM) at the voxel level across subjects including both TBI and HC groups can be used. Here, the interaction term (ΔDTI*wTBM) can be added to see if DTI metrics adjusted by morphometry better explain realistic brain damage in TBI. DTI metrics (ΔFA, ΔMD, ΔAD (axial diffusivity), ΔRD (radial diffusivity)) can be defined as a first and a second subsequent image [Post-Season-Pre-Season, for football or other sports-participant subjects] and local shape changes (E and JD) can be defined on the second (Post-Season) image space.

Based on the correlation between clinically measured data (HIE/Cog) and imaging biomarkers, this approach will provide a new way of defining abnormal voxels in TBI. Also, if the interaction term (ΔDTI*wTBM) is statistically significant, the DTI adjustment process by morphometry can improve the statistical power of DTI metrics.

However, in aging studies, the effects of shear or torsion-related deformations ($E_{12}$, $E_{23}$ and $E_{31}$) might be difficult to determine, while tissue atrophy-related deformations ($E_{11}$, $E_{22}$, $E_{33}$ and JD) are more obvious. Additionally, WM hyperintensity lesions in the brain might have confounding effects with these morphometric parameters because the size of the lesion tends to increase with age, which could require additional incorporation with T2FLAIR images in multi-modality MRI analysis.

The WM morphometry analysis methods that combine multi-modality MRI in a biomechanical framework may play an important role as a bridge between TBM and DTI in longitudinal MRI studies. With these methods, WM tract-specific information associated with a wide range of brain disease as well as normal patterns of development and degeneration can be addressed. Ultimately, this framework could be a paradigm shift in structural morphometry in MRI.

Incorporating multi-modal MRI information may better describe WM formation in a three-dimensional (3D) space. Assuming the WM voxel in MR images is a cube-shaped element containing multiple axonal fibers, WM fiber orientation-specific deformation (axial, cross-sectional and shear deformations in local fibers) can be characterized by applying the finite strain theory in continuum mechanics. Embodiments of the present inventive concept can align voxel-wise 3D deformation tensors estimated from longitudinal T1-weighted images (T1WI) to the local fiber-specific coordinate system defined by "Eigen vectors" from DTI (FIGS. 10, 11, 13A, 14).

Figure 15A:
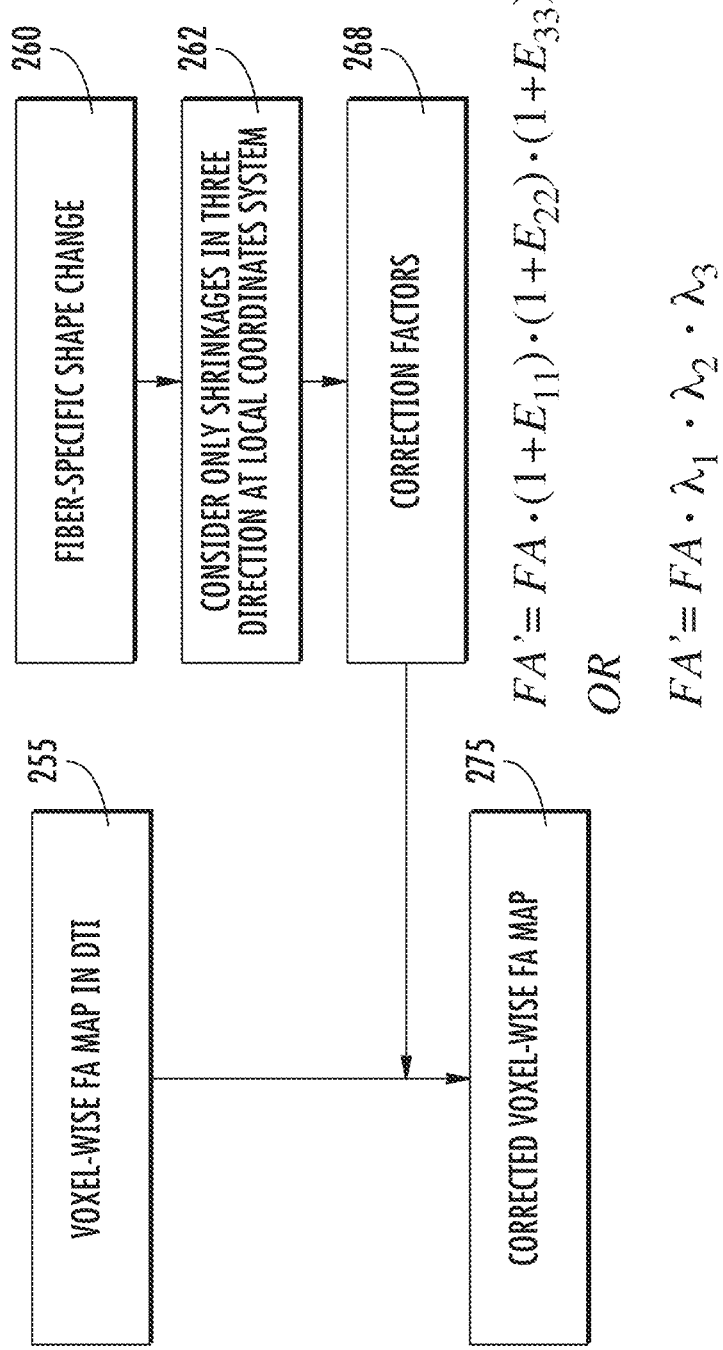
FIG. 15A is a flow chart of an image correction method according to embodiments of the present invention.
Figure 15B:
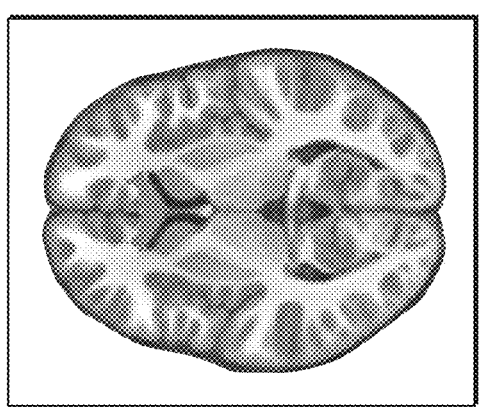
FIG. 15B is a visualization of a corrected FA map of a brain and an appended Table with calculated FA values according to embodiments of the present invention.
Figure 15C:
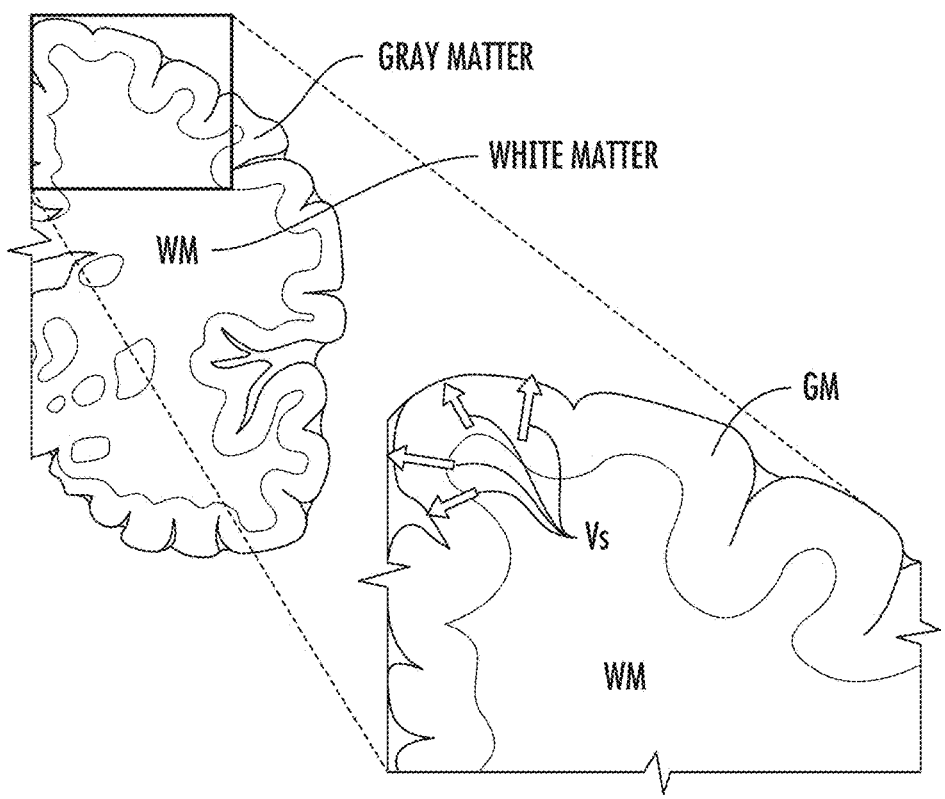
FIG. 15C is a schematic illustration of a portion of a brain image, which can be a Positron Emission Tomography (PET) uptake map, with a segment enlarged to show the use of surface vectors according to embodiments of the present invention.
Figure 15D:
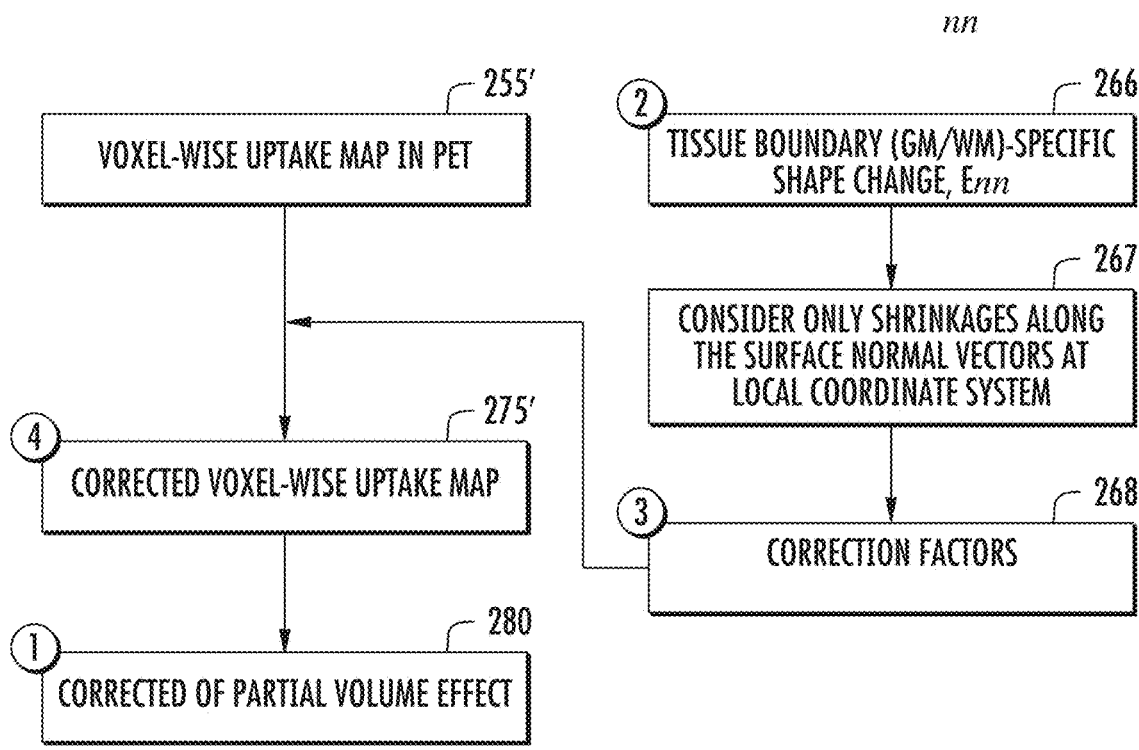
FIG. 15D is a flow chart that can correct the partial volume effect and provide a corrected voxel-wise uptake map according to embodiments of the present invention.

FIGS. 15A and 15D are flow charts of methods of image analysis using correction factors associated with directional strains and/or morphometric information/data. Referring to FIG. 15A, an FA map as an example diffusion parameter map from DTI can be acquired (i.e., a voxel-wise FA map in/from DTI)(block 255). Fiber specific shape changes are identified (block 260), typically by estimating directional strains $E_{11}$, $E_{22}$, $E_{33}$ at a local coordinate system. Identify whether there are shrinkages or other changes in direction at the local coordinate system (block 262). Providing correction factors, typically directional correction factors (block 268). The corrected FA map: FA'=FA*A*B*C→3-directional correction. The correction factors are applied to a voxel-wise FA map (block 255) to generate a corrected voxel-wise FA map (block 275). Similar equations for corrected diffusion parameter maps can be used to apply correction factors to other diffusion parameter maps MD, AD and RD. Thus, the term "diffusion parameter" ("DP") map refers to any of FA, MD, AD and RD maps, which can be corrected to form a corrected diffusion parameter map (DP') (i.e., one or FA', MD', AD', RD' map): DP'=DP*A*B*C.

The directional correction factors can include or be only for negative values of $E_{11}$, $E_{22}$ or $E_{33}$→A=1+$E_{11}$, B=1+$E_{22}$ and C=1+$E_{33}$, where A, B and C are correction factors for three different directions.

The corrected FA map FA' can be calculated using, for example:

$$FA'=FA \cdot (1+E_{11}) \cdot (1+E_{22}) \cdot (1+E_{33}) \qquad \text{Equation (9)}$$

OR $$FA'=F_A \cdot \lambda_1 \cdot \lambda_2 \cdot \lambda_3 \qquad \text{Equation (10)}$$

Where $E_{11}$, $E_{22}$ and $E_{33}$ are directional strains at a local coordinate system $e_1$, $e_2$, $e_3$, estimated as discussed herein and a is the directional stretch ratio (with the subscripts identifying three different directions at local coordinate system). Stretch ratios were discussed above. Again, similar equations for other types of corrected diffusion parameter maps can be used to apply correction factors to other diffusion parameter maps DP, i.e., MD, AD and RD.

In Diffusion Tensor Imaging (DTI), brain tissue shrinkages are related to overestimation of FA. So, negative values of directional strains ($E_{11}$, $E_{22}$ and $E_{33}$) or directional stretches may be the only parameters required for inclusion in the correction or over estimation. However, for other modalities of imaging, both positive and negative values of directional deformation may be considered, depending on the physical properties.

FIG. 15B is a mean FA of a Genu of Corpus Callosum (red/dark colored arc region) of a 12 year old boy (youth football) that was exposed to a head impact of 1.23 (unit of risk cumulative exposure). Corrected F A values were determined using fiber-specific morphometric changes. The appended table reflects a Pre Season F A value, a pre-correction Post Season F A value and a corrected Post Season F A value calculated using the method described in FIG. 15B. The corrected value (0.379) is smaller than the pre-correction value (0.384). The pre-correction, Post-Season value is the same as the Pre Season value.

Referring to FIG. 15D, an example of a method for correcting Positron Emission Tomography (PET) voxel-wise uptake maps (block 255') is shown. FIG. 15C illustrates grey matter (GM) and white matter (WM) and the use of surface normal vectors Vs for generating correction factors (block 268). Generally stated, partial volume effect (PVE) can be defined as the loss of apparent activity in small objects or regions because of the limited resolution of the imaging system. It occurs in medical imaging and more generally in biological imaging such as positron emission tomography (PET). See, e.g., https://en.wikipedia.org/wiki/Partial_volume_(imaging)).

However, in longitudinal studies, it may be informative to consider shape change together for more reliable PVE.

Enn: directional strains normal to the surface of gray matter (GM)/white matter (WM) boundary can be derived at local coordinate system to identify tissue boundary (GM/WM) specific shape change (block 266). Surface normal vectors (Vs black arrows in FIG. 15C) can be defined by brain tissue segmentation and publically available surface morphometry algorithms such as FreeSurfer or SPM.

Then correction factors can be determined (block 268). A three-dimensional deformation derived as discussed above but with the surface normal vectors Vs can be used to estimate the directional correction factors (block 268).

A corrected uptake or activity map can then be calculated (block 275'): uptake value corrected=[uptake value] *A→1-directional correction. This yields an activity map with a correction of partial volume effect (block 280).

Embodiments of the present invention can provide new WM morphometry analysis methods that combines multi-modality MRI (or other image modalities) and mechanical deformation theory as a bridge between TBM and DTI in longitudinal image studies. With this method, WM tract-specific biomechanical information that describes abnormal brain development/degeneration patterns may be derived. This framework may provide a new paradigm to merge different imaging modalities, so that high-dimensional information in structural morphometry can be extracted.

Figure 16:
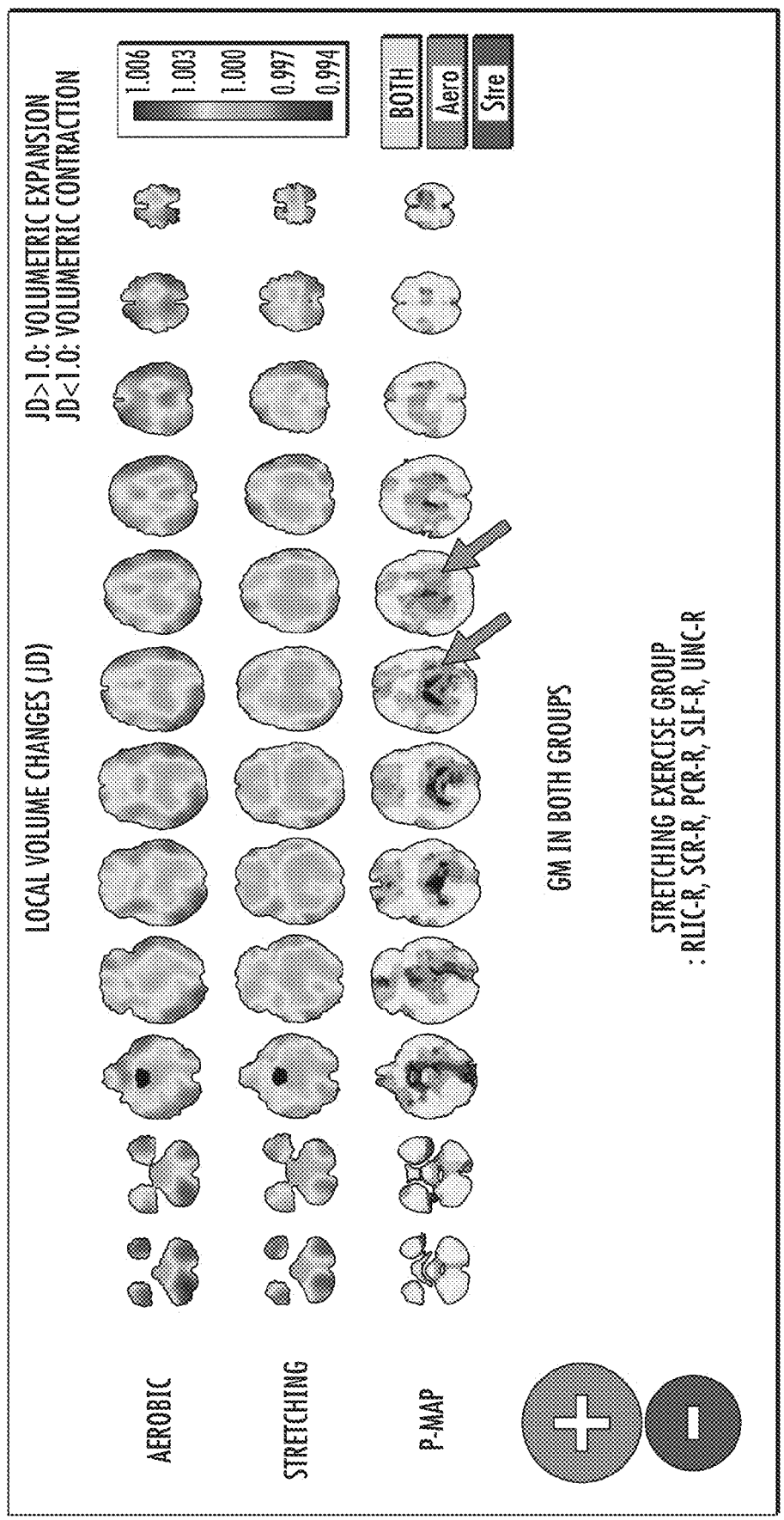
FIG. 16 is a series of images showing local volume changes (JD) based on aerobic and stretching and an appended series of p-maps of same according to embodiments of the present invention.

FIG. 16 illustrates images of local volume changes (JD) for aerobic and stretching exercises performed by the subject with green showing increase and red showing decrease in tissue. A p-map of the corresponding images illustrates volume changes associated with both or different ones of the exercises.

Figure 17:
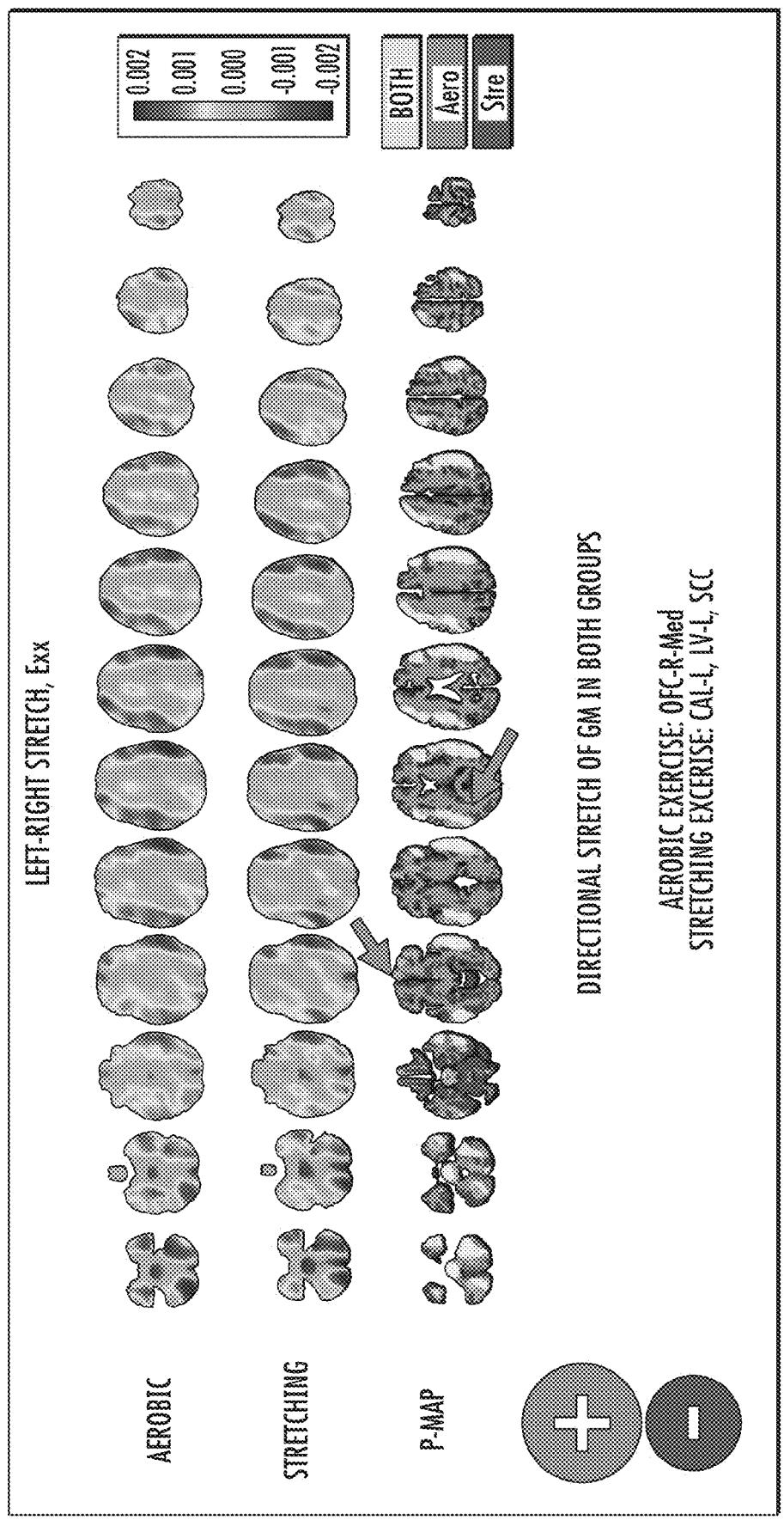
FIGS. 17-19 are a series of images showing directional stretch change based on aerobic and stretching and an appended series of p-maps of same according to embodiments of the present invention.
Figure 18:
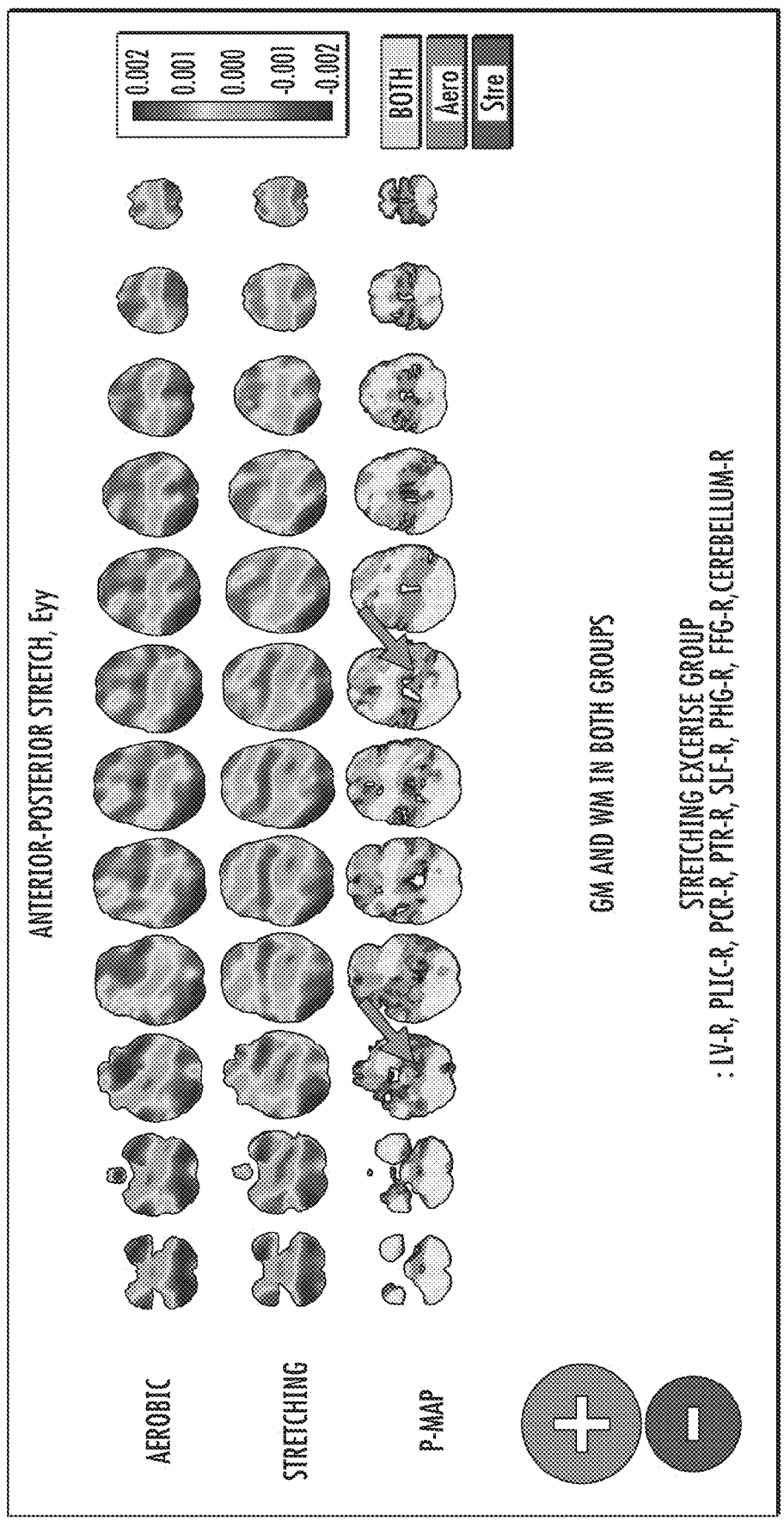
Figure 19:
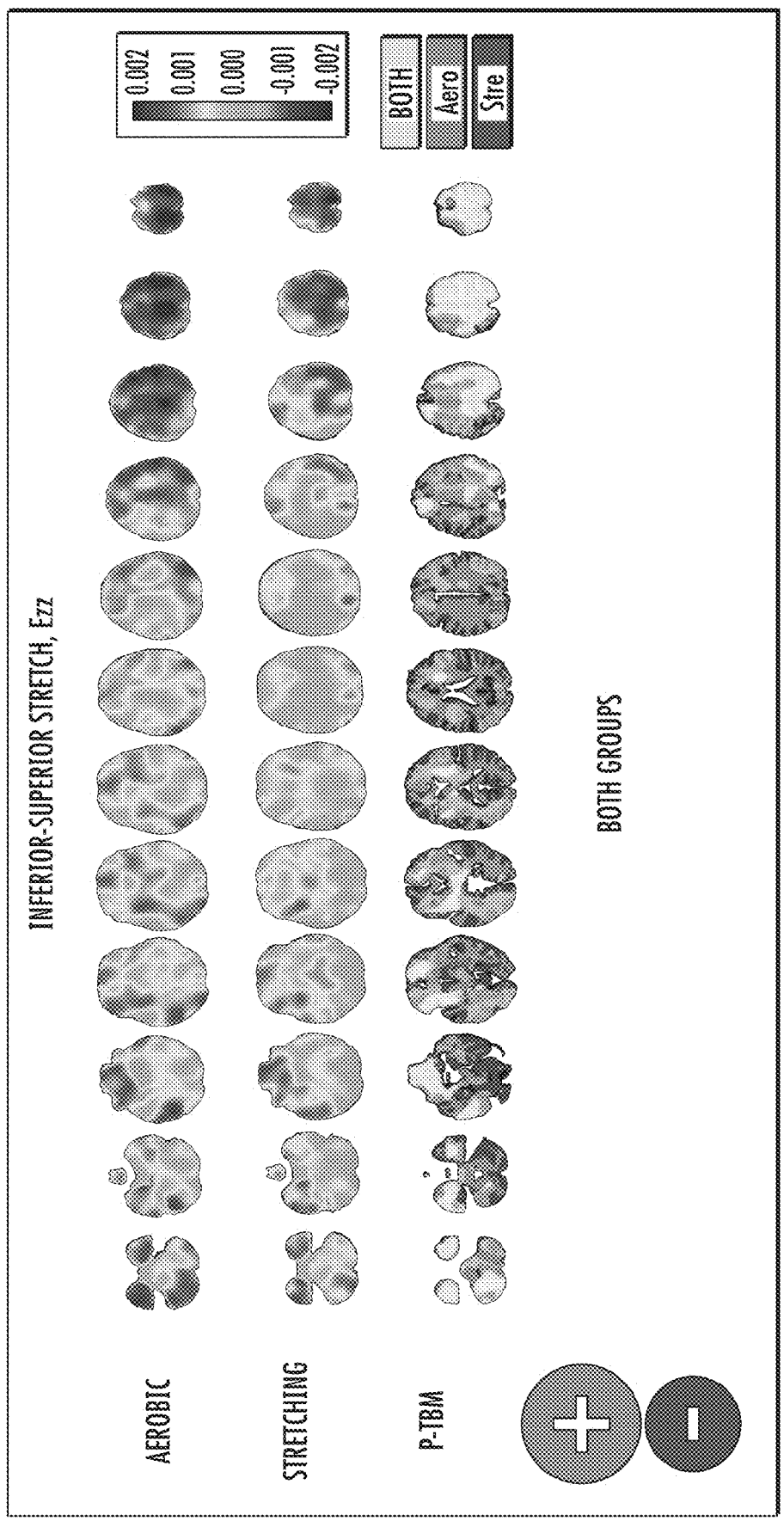

FIGS. 17-19 show directional stretch (Exx, Eyy, Ezz) for these same exercises (from positive stretch 0.002 to negative or "shrink" (−0.002), in color scale. A corresponding p-map is also shown in color representing change due to both exercises or one of the different exercises. In both groups, there is a local volume increase (GM prominent) with a larger area of volumetric/directional expansion or stretch in aerobic exercise group. For the stretching exercise group, there is a volumetric contraction in some ROIs (A-P shrink).

Figure 20:
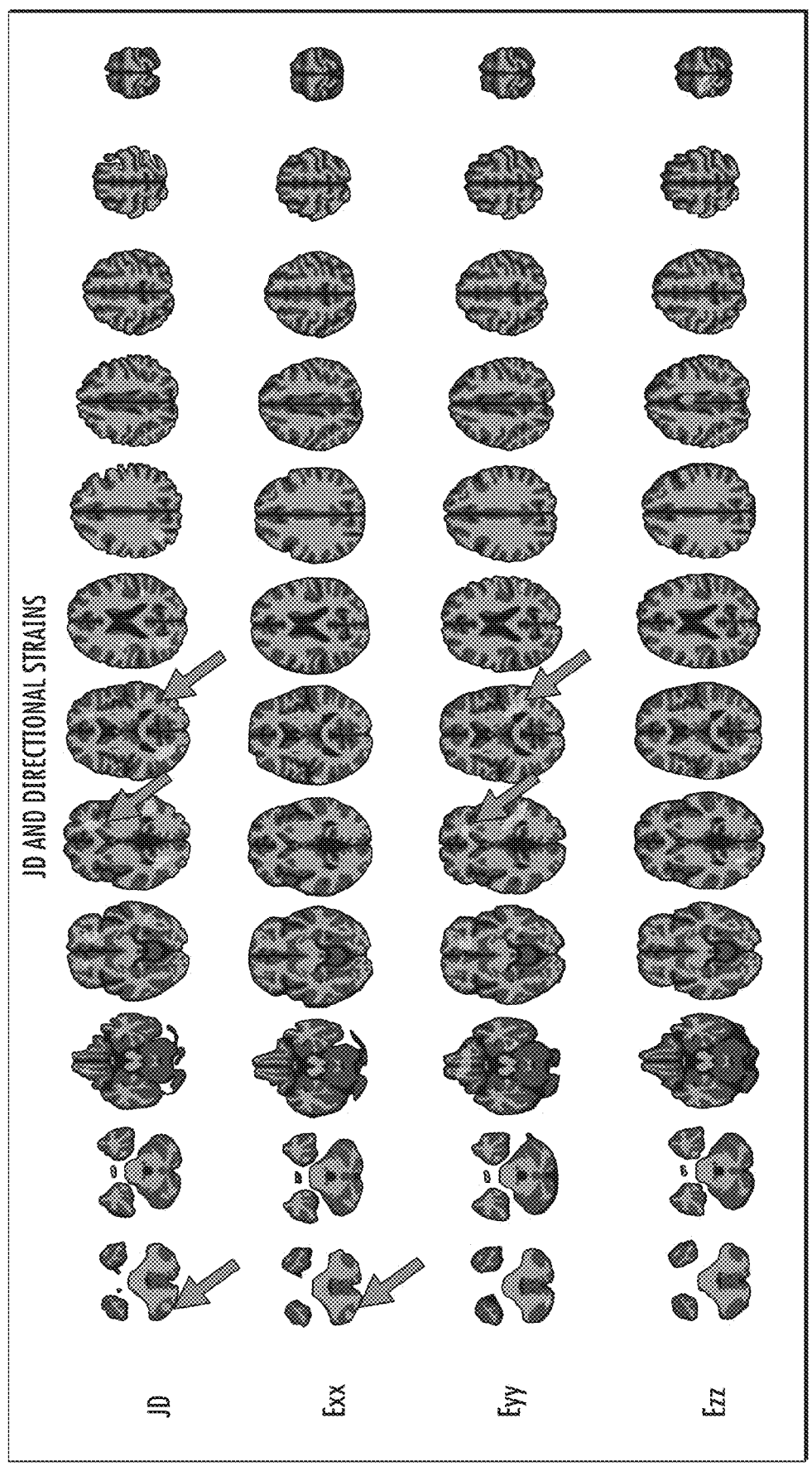
FIG. 20 are a series of images showing directional strain change compared to local volume (JD) changes according to embodiments of the present invention.

FIG. 20 shows the JD and directional change ROI images together. It is believed that the complementary role of directional/shear strains to volumetric changes may allow for early detection of morphological changes. Also, aerobic exercise may enhance local brain volume preservation by local volumetric expansion and/or directional stretching.

FIG. 21 is a chart of complementary relationships of the local volume (JD) to directional changes in four categories, further comprising electronically classifying the determined directional and shear changes as one of four groups of deformation topology types: Type I: isotropic directional change with a volumetric change; Type II: anisotropic directional change with a volumetric change; Type III: anisotropic directional change without a volumetric change; and Type IV: shear deformation/strains.

Figure 22A:
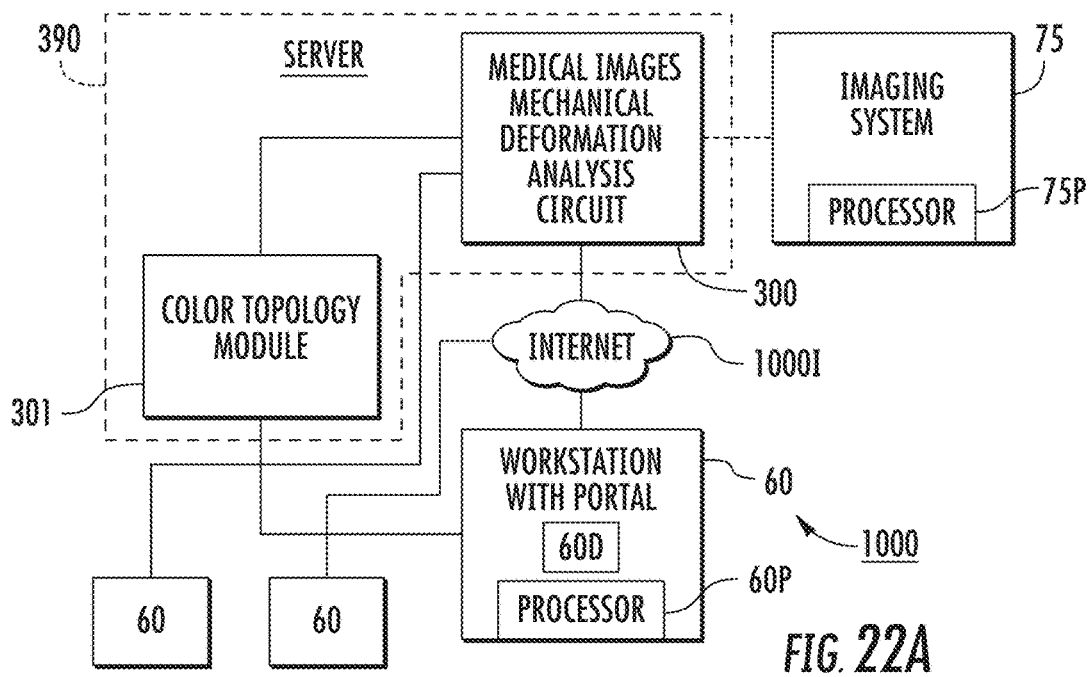
FIG. 22A is a schematic illustration of a finite element based medical image evaluation circuit in communication with an imaging system according to embodiments of the present invention.
Figure 22B:
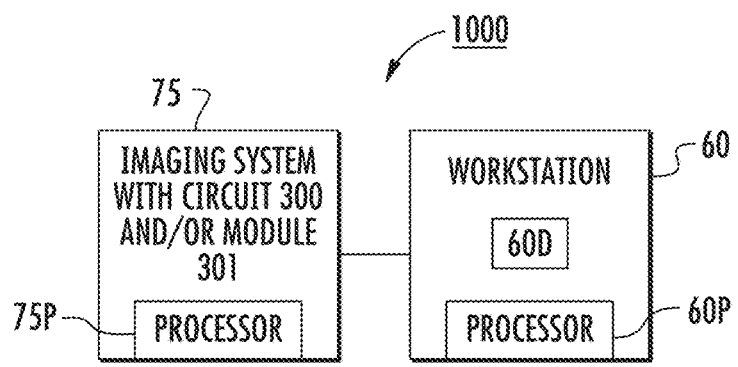
FIG. 22B is a schematic illustration of a circuit/module onboard the MR Scanner (console) according to embodiments of the present invention.
Figure 22C:
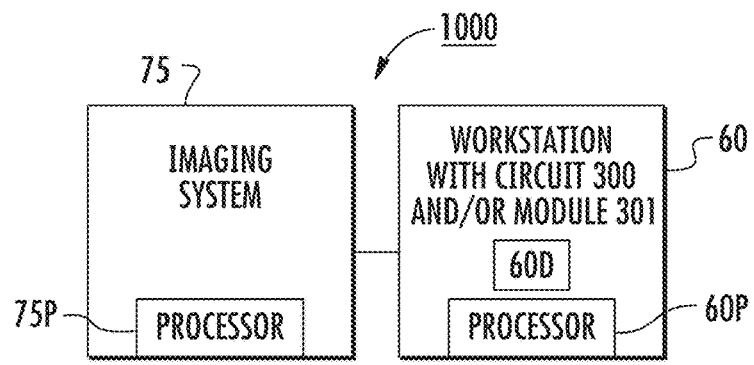
FIG. 22C is a schematic illustration of a circuit/module held at least partially on a server according to embodiments of the present invention.

FIGS. 22A-22C illustrate exemplary image analysis systems 1000 with a finite element based mechanical deformation analysis circuit 300 and/or topology directional change map module 301. The system 1000 can be configured to electronically generate visualizations of color topology directional change maps. The system 1000 can include or be in communication with a workstation 60 and/or imaging system 75 (i.e., MR and/or CT Scanner) can each include or be in communication with (a remote or local) at least one processor 60P, 75P, respectively, that can be configured to carry out all or part of the image analysis and image acquisition.

The image analysis can be performed post-imaging session so that it is a post image data acquisition analysis that can be carried out by a system 1000 that is separate from the imaging system 75 used to acquire the image data, such as a PACS system.

FIG. 22A illustrates that the system 1000 can include at least one workstation 60 that has an optional computer portal for accessing the module 301 and/or circuit 300. The module 301 can be held on at least one server 390 accessible via a LAN, WAN, SAN or Internet 1000I. The workstation 60 can communicate with patient image data which may be held in a remote or local server, in the imaging system 75, such as an MRI Scanner or other electronically accessible database or repository. The workstation 60 can include a display with a GUI (graphic user input) and the access portal. The workstation can access the data sets via a relatively broadband high speed connection using, for example, a LAN or may be remote and/or may have lesser bandwidth and/or speed, and for example, may access the data sets via a WAN and/or the Internet. Firewalls may be provided as appropriate for security.

The at least one server 390 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

A plurality of different clinical sites can be in communication with the at least one server 390. The at least one server 390 can receive and analyze multiple images of respective patients from the different sites at any one time.

The image analysis system 1000 may also operate to render images using data sets from more than one of these modalities. That is, the system 1000 may be configured to provide the mechanical deformation analysis and/or render visualizations irrespective of the imaging modality data type (i.e., a common system may evaluate images for both CT and MRI volume image data).

The analysis system 1000 can include at least one display or screen 60D, typically onboard or in communication with a clinical site workstation 60. It is noted that the terms "display" and "screen" are used interchangeably. The display 60D may be held on any type display and, indeed, more than one display, including, for example, an electronic notebook, smart phone, laptop computer, desktop computer or a workstation 60.

FIG. 22B illustrates that the circuit 300 and module 301 can be included in the imaging system 75 which can communicate with a workstation 60. The module 301 and/or circuit 300 can be integrated into the control cabinet of the MR Scanner with image processing or scan sequence control circuitry. FIG. 22C illustrates that the circuit 300 and/or module 301 can be integrated into one or more local or remote workstations 60 that communicates with the imaging system 75. Although not shown, parts of the circuit or module can be held on both the imaging system 75 and one or more workstations 60, which can be remote or local. The module and circuit, where a module is also used, can be combined or separated into further components.

Figure 23:
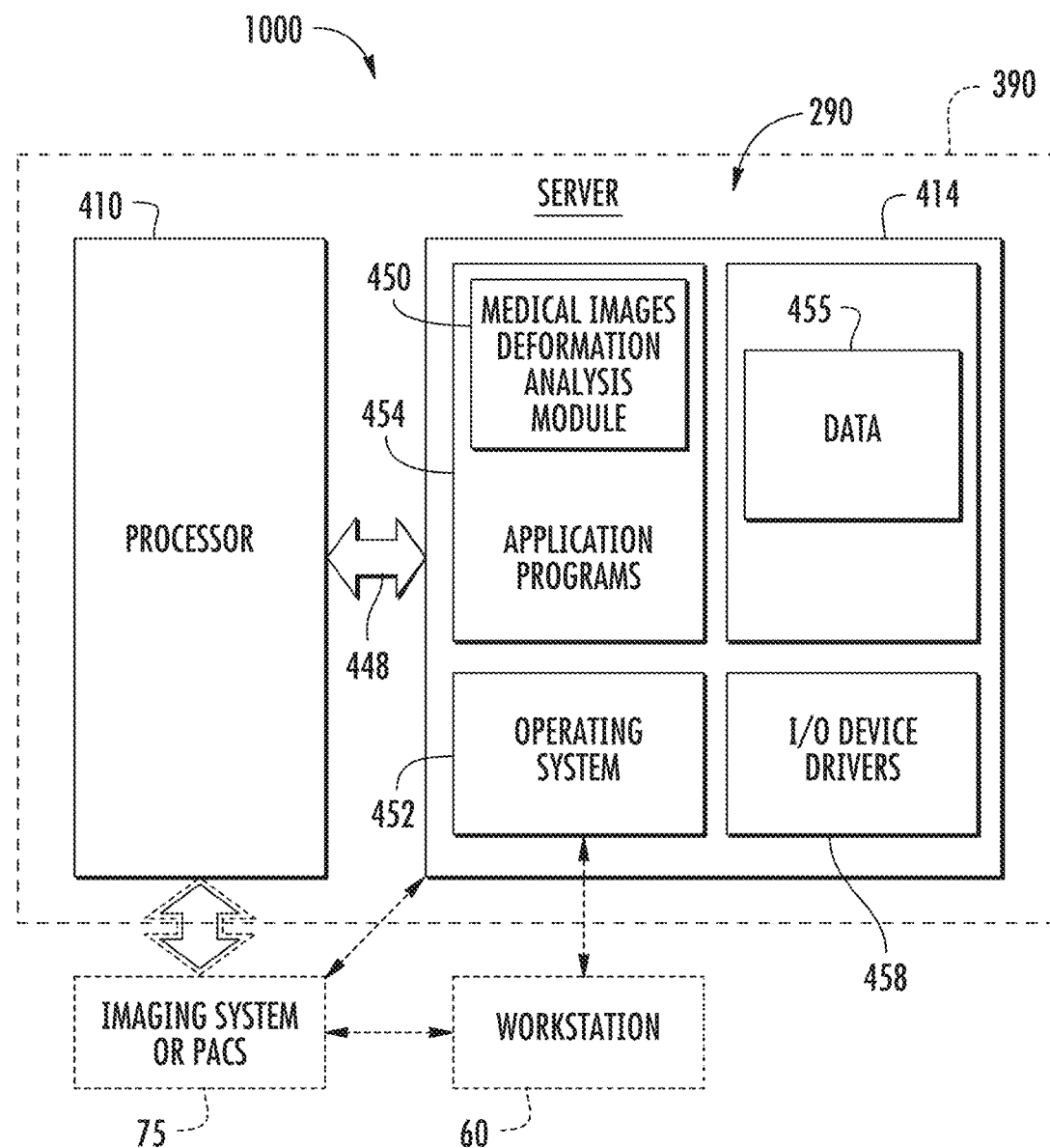
FIG. 23 is a block diagram of a data processing system according to embodiments of the present invention.

FIG. 23 is a schematic illustration of a circuit or data processing system 290 which can optionally be provided by at least one server 390. The data processing system 290 can be used with any imaging system 75, such as a CT Scanner system or a MR Scanner system and provide all or part of the circuit 300. The data processing systems 290 may be incorporated in a digital signal processor in any suitable device or devices. As shown in FIG. 17, the processor 410 can communicate with (or be partially or totally onboard) an imaging system (such as, but not limited to an MRI scanner) 75 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 23 illustrates that the memory 414 may include several categories of software and data used in the data processing system: the operating system 452; the application programs 454; the input/output (I/O) device drivers 458; and data 455. The data 455 can include patient identification information, different images taken at different points in time and the like. As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, windowsxp or other Windows versions from Microsoft Corporation, Redmond, Wash., Unix or Linux or freebsd, Palm OS from Palm, Inc., Mac OS from Apple Computer, labview, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Medical Image Deformation Analysis Module 450 being an application program in FIG. 23, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 23 which is intended to encompass any configuration capable of carrying out the operations described herein. Further, Module 450 can communicate with, such as via an intranet or the Internet, or be incorporated totally or partially in other components, such as a control system of an imaging system (i.e., a control cabinet of an MRI scanner) 75, an interface/gateway or workstation.

The I/O data port can be used to transfer information between the data processing system, a workstation, the imaging system, a clinician, an interface/gateway and another computer system or a network (e.g., the Internet) or to other devices or circuits controlled by or in communication with the processor, Module, circuit and/or at least one server 390. These components may be conventional components such as those used in many conventional data processing systems, which may be configured in accordance with the present invention to operate as described herein.

Embodiments of the invention can be used for evaluating images from various imaging modality images, of different soft tissues, or organs of the body and/or for different medical conditions and may identify new biomarkers using the morphometric parameters based on mechanical deformation in 3-D of each voxel in an ROI.

Examples of different uses of the analysis methods using 3-D finite element analysis are provided below.

A. Brain Evaluation/Biomarkers

Alzheimer's Disease

Mild Cognitive Disorder

Concussions or other Brain Injuries

Addiction

Anxiety

Stroke, such as, but not limited to, infraction in Diffusing Weighted Imaging

Progressive Neurological Diseases, such as, but not limited to Multiple Sclerosis and Parkinson's Disease Mental Disease States Hydrocephalus

ADHD

ADD

B. Cancer Evaluations

Brain Cancer

Lung Cancer

Breast Cancer

Renal Cancer

Prostate Cancer

C. Clinical Trials

D. Drug Discovery

E. Evaluating Physical, Dietary and/or Drug Induced Changes

F. Monitoring for Positive and Negative Therapeutic-Induced Changes

The invention will now be described further with respect to the following non-limiting Examples.

EXAMPLES

Example 1

The human brain exhibits highly dynamic structural and functional changes during early infancy[1,2] as a consequence of interaction between genetic programming, epigenetic and environmental factors. The intracranial brain volume (ICV) increases by 101% in the first year and 15% in the second year, which is about 83% of the adult volume[3]. In the cortex, there is rapid elaboration of new synapses in the first two years of life. Myelination of white matter also proceeds rapidly in the first two years after birth, with the overall pattern of adult myelination completed by the end of the second year of life. However, it is poorly understood how dynamic structural change is related with achievement of psycho-motor and cognitive skills during brain development. In addition, abnormal brain volumetric growths have been widely reported during early infancy and childhood; autism subjects showed brain overgrowth for the first year of life[4], fragile X syndrome patients exhibited increased caudate and lateral ventricle volumes[5], and schizophrenic patients showed slower growth rates of white matter[6]. Therefore, this dynamic nature of brain growth requires the sensitive strategies to detect, track and quantify structural change in the brain in spatiotemporal domain[7].

Using advanced image analysis tools, various parameters related to infant brain development have been evaluated including ICV[3,8], tissue specific volumes, regional brain volumes[9,10], cortical thicknesses, surface areas and gyrification indices[11]. Longitudinal MR studies incorporating automated image segmentation techniques have delineated a rapid and dynamic brain volume growth profile from birth to 2 years of age[3,12,13]; differential/asymmetric volume growth of different tissue types (gray matter, white matter and cerebrospinal fluid) and functional regions[1,8,9] have been reported. In addition tensor-based morphometry (TBM) has also been exploited to identify regional structural differences using the gradients of the nonlinear deformation fields derived from aligning individual images to a common anatomical template[14,15]. Using TBM, Jacobian determinant (JD) can be used to discern local volume expansion or contraction relative to the corresponding anatomical structures in a given template[16]. While all of these existing approaches have provided valuable insights into early brain development, none of these approaches provides directionally specific growth information: let us consider an image voxel for which the eigenvalues of the Jacobian matrix are $\lambda_{1,2,3}=\{1, 2, 0.5\}$. In such a case the value of JD would be 1 (assuming all off-diagonal components of Jacobian matrix are zeros). Thus, though the directional stretch and shrink exist, this directional change is not able to be detected by only JD[17,18]. To this end, the finite strain theory of continuum mechanics was employed as an extension of TBM to offer additional insights into early brain development in this study.

Finite strain theory of continuum mechanics offers an ideal framework to model large deformation phenomena. In particular, its ability to model not only volumetric deformation but also changes of line element's length and orientation has lent itself to numerous applications on the analysis of elastomers, plastically-deforming materials and biological soft tissues[19]. Leveraging these advantages, Rajagopalan et al. utilized finite strain theory to analyze MR images acquired from 38 fetuses. They reported that the most significant changes in the directionality of growth were in the cortical plate located at the major sulci[19]. Furthermore, Studholme and Cardenas showed the orientation of volume changes between abstainers from, and those who relapse to, alcohol use[17]. While these studies have demonstrated the potential advantages of finite strain theory in characterizing brain morphological changes, there are two major limitations. First, deformation of a region of interest (ROI) was decomposed into stretch (scaling) and rotation of infinitesimal elements (polar decomposition). As a result, it is only physically reasonable for one-dimensional case. That is, if a cube object experiences directional stretches and rotations, the deformed cube becomes rectangular cuboid. In reality, biological growth/deformation involves three-dimensional shearing, making the shape of deformed element more complex[20]. Second, a cross-sectional design was employed in the previous studies, making it difficult to exclude potential confounds arisen from inter-subject variability.

To mitigate the above outlined limitations associated with the previous studies and enable characterization of complex three-dimensional brain growth, a Lagrange strain of finite strain theory was employed together with images obtained from a longitudinal imaging study. Lagrange strain tensor models how a volumetric ROI deforms in the coordinate system of reference configuration; diagonal components describe directional stretches and shrinks of line elements whereas off-diagonal components represent rotation of line elements and shearing of a volumetric ROI. Specifically, a volumetric ROI can be modeled as a combination of several line elements. Three-dimensional deformation processes thus can be tracked through each line element and reconstruct a new volumetric ROI in a deformed configuration by applying finite strain theory. In this study, directionally specific growth behaviors are characterized using a cohort of subjects who were longitudinally imaged five times during the first year of life which can uncover nonlinear, anisotropic and inhomogeneous brain growth and determine age-specific directional and volumetric growth rates during a critical time period of early brain development.

Results

Volumetric Growth of the Brain for the First Year of Life

Figure 24:
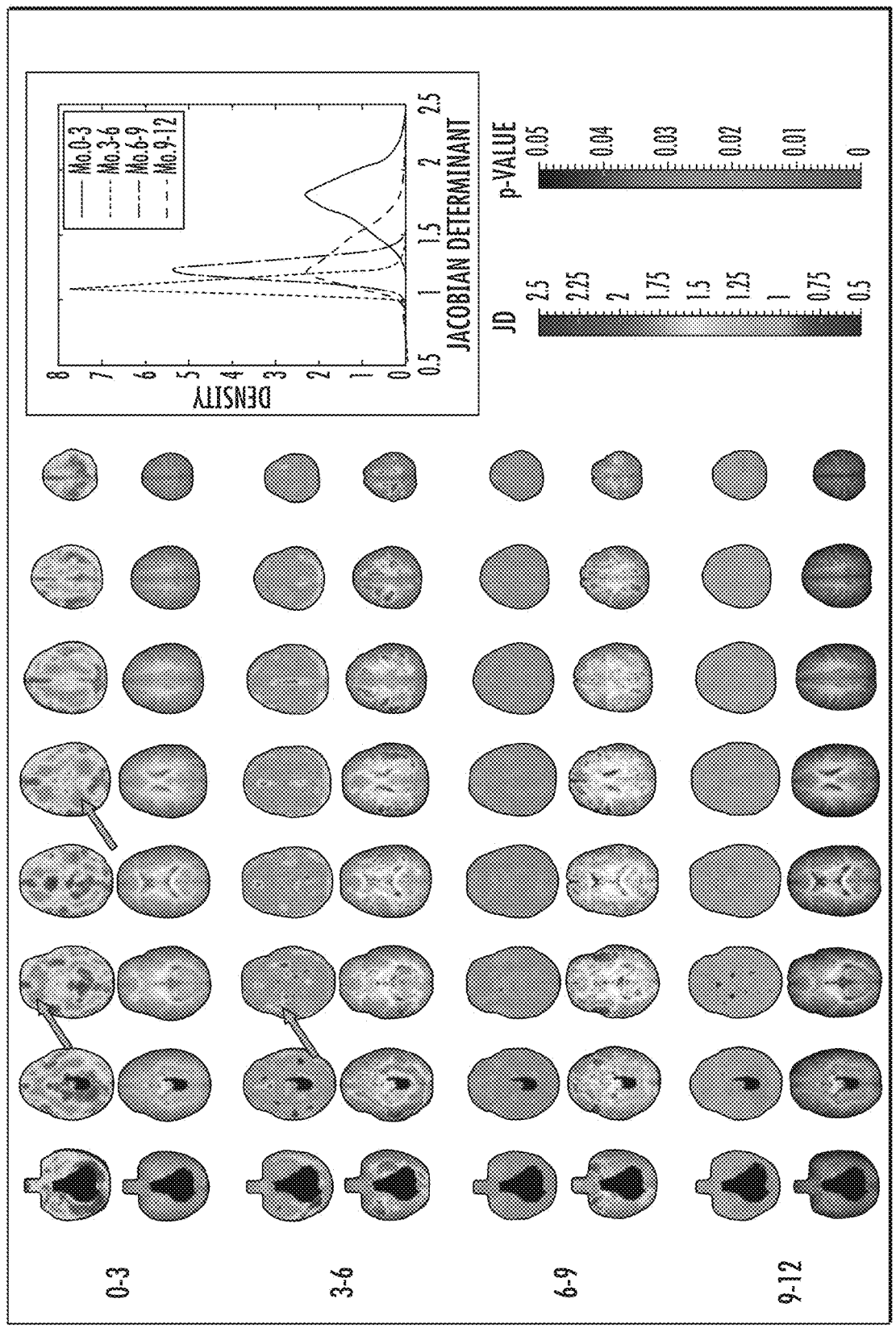
FIG. 24 are parametric images of mean volume growth rates (JD) of four time periods during the first year of life according to embodiments of the present invention.

The subjects were scanned at 26±8, 102±25, 189±9, 279±15 and 372±14 postnatal days, respectively. Adjusted mean volumetric growth rates (JD) during the 4 time periods, 0-3, 3-6, 6-9 and 9-12 months, are shown on the Year-1 infant atlas space (FIG. 24). A clear demarcation was observed regarding the characteristics of JD between 0-6 and 6-12 months of age; a substantial volume expansion (JD>1.0) at the cortical regions is observed during the first 6 months of life, followed by more spatially uniform JD during the second half of the first year. On the other hand, most of the major white matter tracts exhibit a lower JD, suggesting relatively slow growth during the first year of life. The distributions of JD during the four time periods are shown in the upper right column of FIG. 24. Although the distributions of JD are broad during the first 6 months of life, the peak is left-shifted during 3-6 months, suggesting a reduced pace of volume expansion in this time period when compared to that during 0-3 months. Interestingly, although the mean JD is similar for the time periods of 3-6 months and 6-9 months, the distribution is much narrower during 6-9 months. Finally, the mean is further left-shifted and the distribution is much narrower at the time period of 9-12 months when compared to that between 6-9 months.

Figure 25:
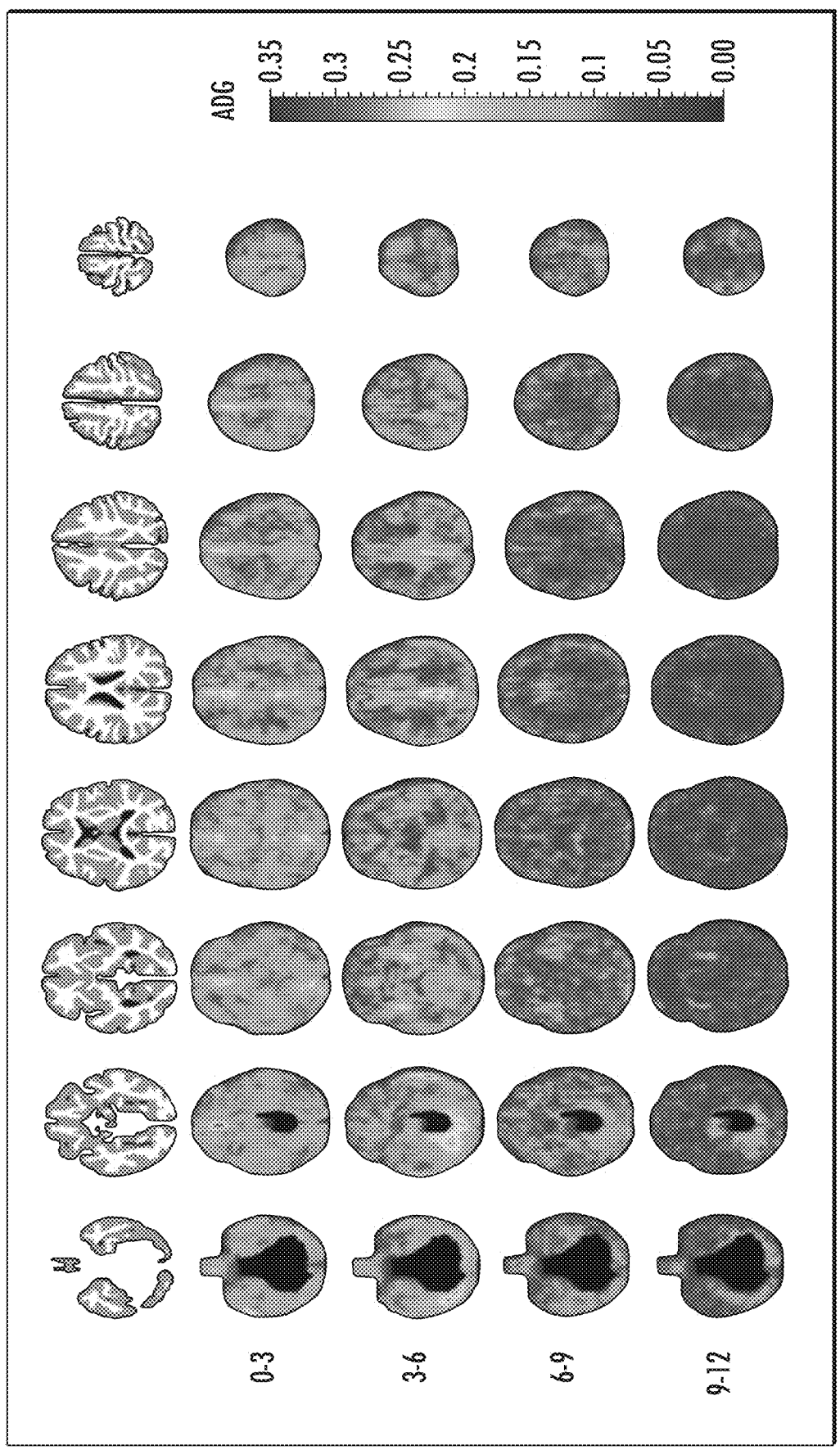
FIG. 25 are anisotropy of directional growth (ADG) maps based on directional stretches along the main axes according to embodiments of the present invention.
Figure 26:
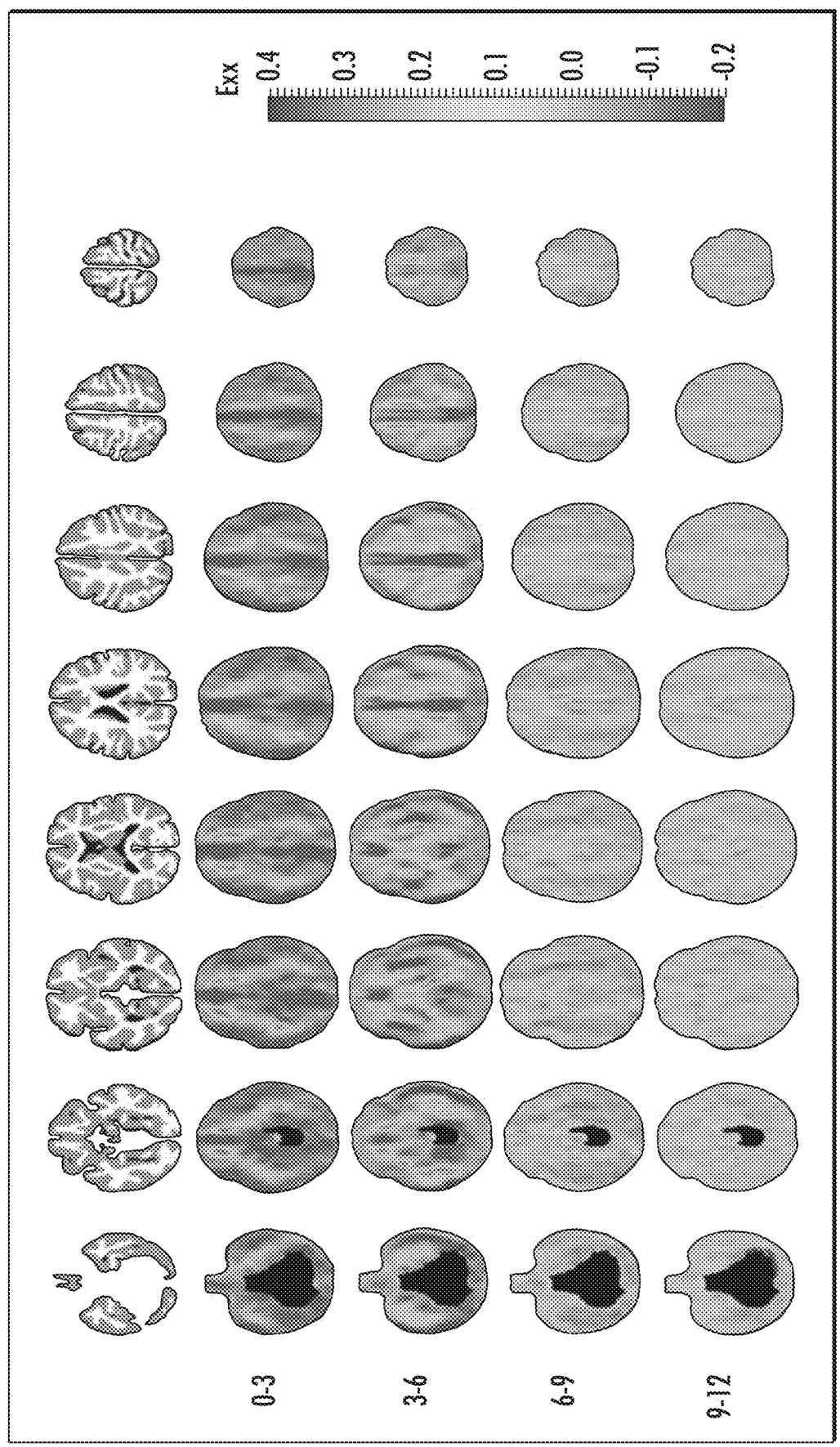
FIG. 26 are left to right directional normal strains during the first year of life according to embodiments of the present invention.
Figure 27:
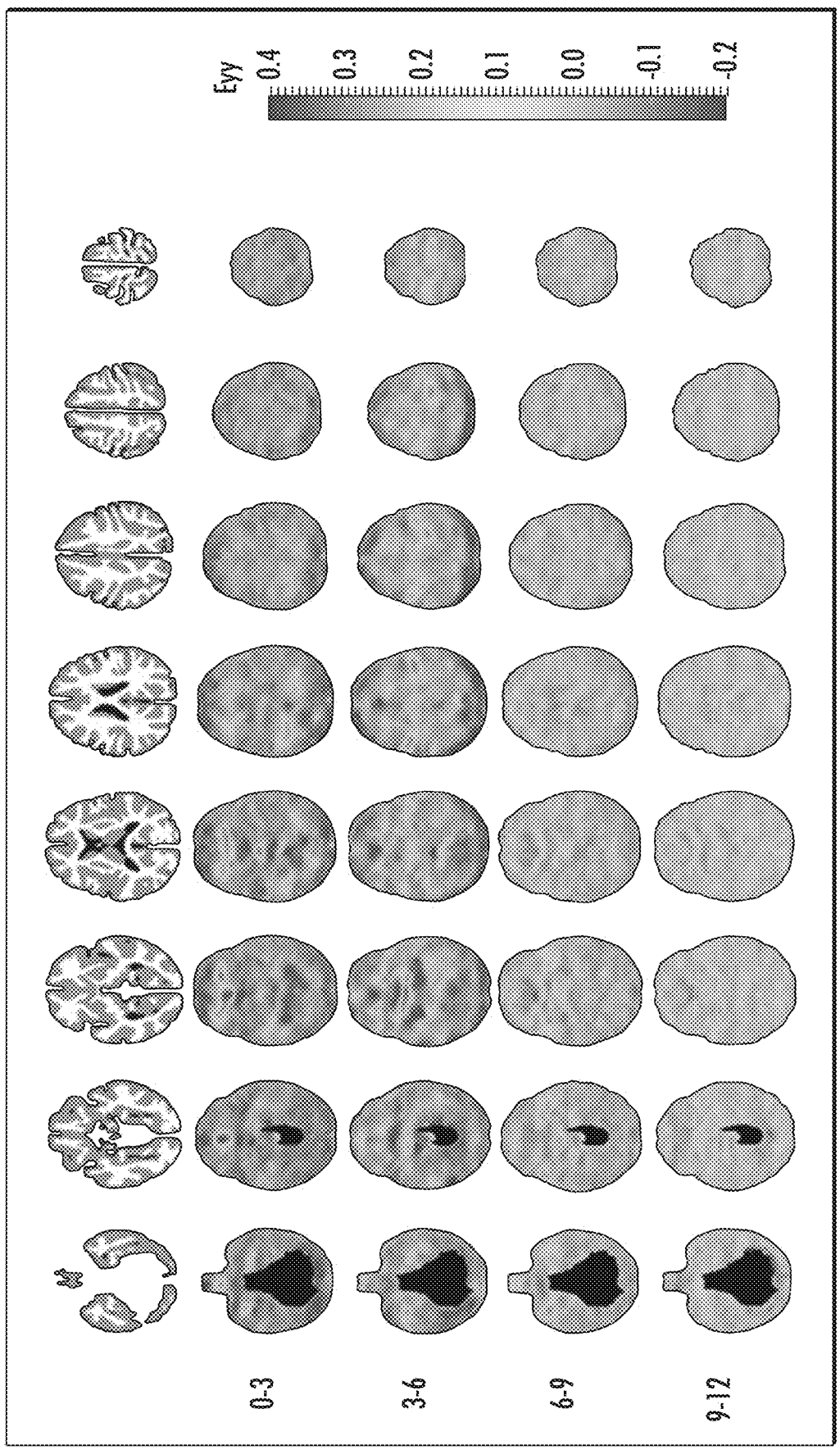
FIG. 27 are posterior-anterior directional normal strains during the first year of life according to embodiments of the present invention.

Mean values of JD and strains of each ROI were computed. Brain regions exhibiting a mean JD greater than 75$^{th}$ percentile ($JD^{0-3}>1.91$ and $JD^{3-6}>1.45$) or less than $25^{th}$ percentile ($JD^{0-3}<1.68$ and $JD^{3-6}<1.20$) of all voxels in the brain, including white matter and cerebrospinal fluid, were defined as prominent and slow growing regions, respectively (Tables 1 and 2). Regions with prominent increase of JD are mainly in the right hemisphere adjacent to the interhemispheric fissure (cingulum, lingual, Fusiform, calcarine, cuneus, precuneus, rectus and olfactory gyri). Additionally, some areas of the visual cortex showed higher growth patterns (months 0-12). More importantly, regions related higher cognitive functions showed a higher volumetric growth from month 6 (temporal, parietal, angular and supramarginal gyri). Despite the prominent brain tissue expansion observed in many brain regions, not all brain regions exhibited volume expansion during the first year of life. In particular, some areas of the white matter including anterior corona radiata (months 0-3) and inferior longitudinal fasciculus (months 3-6) showed non-significant volume changes ($p>0.05$ after FDR correction). Regions in the left hemisphere showed relatively slow volumetric growth during the first 6 months, including cingulum, amygdala, hippocampus, and pallidum. After month 6, temporal pole and frontal pole areas showed lower volumetric growth. Finally, no brain region showed statistically significant volume expansion or contraction in the time period of 9-12 months ($p>0.05$ after FDR correction) (FIG. 25).

Direction-Specific Changes of the Brain

While JD provides insights into early brain development, it does not, however, offer information on directional growth. FIG. 25 shows the anisotropy of the directional growth (ADG) during the four time periods whereas the corresponding directional elongations along x ($E_{xx}$, left-right), y ($E_{yy}$, anterior-posterior), and z ($E_{zz}$, superior-inferior) directions are shown in FIGS. 20-22, respectively. Qualitatively, the directional normal strains are spatially non-homogeneous and are age-dependent as shown in ADG maps. These regions showing higher ADG correspond to directionally-specific growth patterns. For the x-direction, remarkably higher rates of changes of normal strains are observed in the interhemispheric fissure and cortical areas for the first 6 months (Table 1). Specifically, right cingulum, right lingual, right olfactory, right recturs, right medial orbitofrontal, right precuneus gyri showed active x-directional stretches ($>75^{th}$ percentile ($E_{xx}^{0-3}>0.25$ and $E_{xx}^{3-6}>0.17$) of the whole brain $E_{xx}$). Even though not statistically significant, slight local contractions in x-direction are observed in the middle cingulums, anterior/posterior corona radiata for the first 6 months. Small x-directional stretches ($<25^{th}$ percentile of the whole brain, ($E_{xx}^{0-3}<0.12$ and $E_{xx}^{3-6}<0.056$)) were mainly at the subcortical areas of the left hemisphere, including amygdala, putatmen, pallidum and caudate (Table 2). For y-directional normal strains, the lateral ventricles, bilateral occipital, bilateral olfactory, bilateral lingual, bilateral cuneus, right superior temporal pole and right angular gyri showed growth rates greater than $75^{th}$ percentile ($E_{yy}^{0-3}>0.19$ and $E_{yy}^{3-6}>0.17$) for the first 6 months. Significant local contractions are also observed in y-direction, including the anterior cingulum and anterior regions of corona radiata during the first 3 months ($p<0.05$ after FDR correction). Left amygdala also showed a low y-directional stretch ($<25^{th}$ percentile of the whole brain during the first three months ($E_{yy}^{0-3}<0.11$ and $E_{yy}^{3-6}<0.076$)). In z-direction, bilateral fusiform, right inferior occipital, right inferior parietal, left heschl, right inferior temporal gyri and lateral ventricles showed growth rates greater than $75^{th}$ percentile ($E_{xx}^{0-3}>0.21$ and $E_{xx}^{3-6}>0.18$) for the first 6 months. After first 6 months, as observed in JD, more uniform directional stretch patterns were developed, but significant z-directional stretch patterns were observed at bilateral lingual gyri, right fusiform gyrus and right inferior temporal gyrus.

Shear Deformations of the Brain

Figure 29:
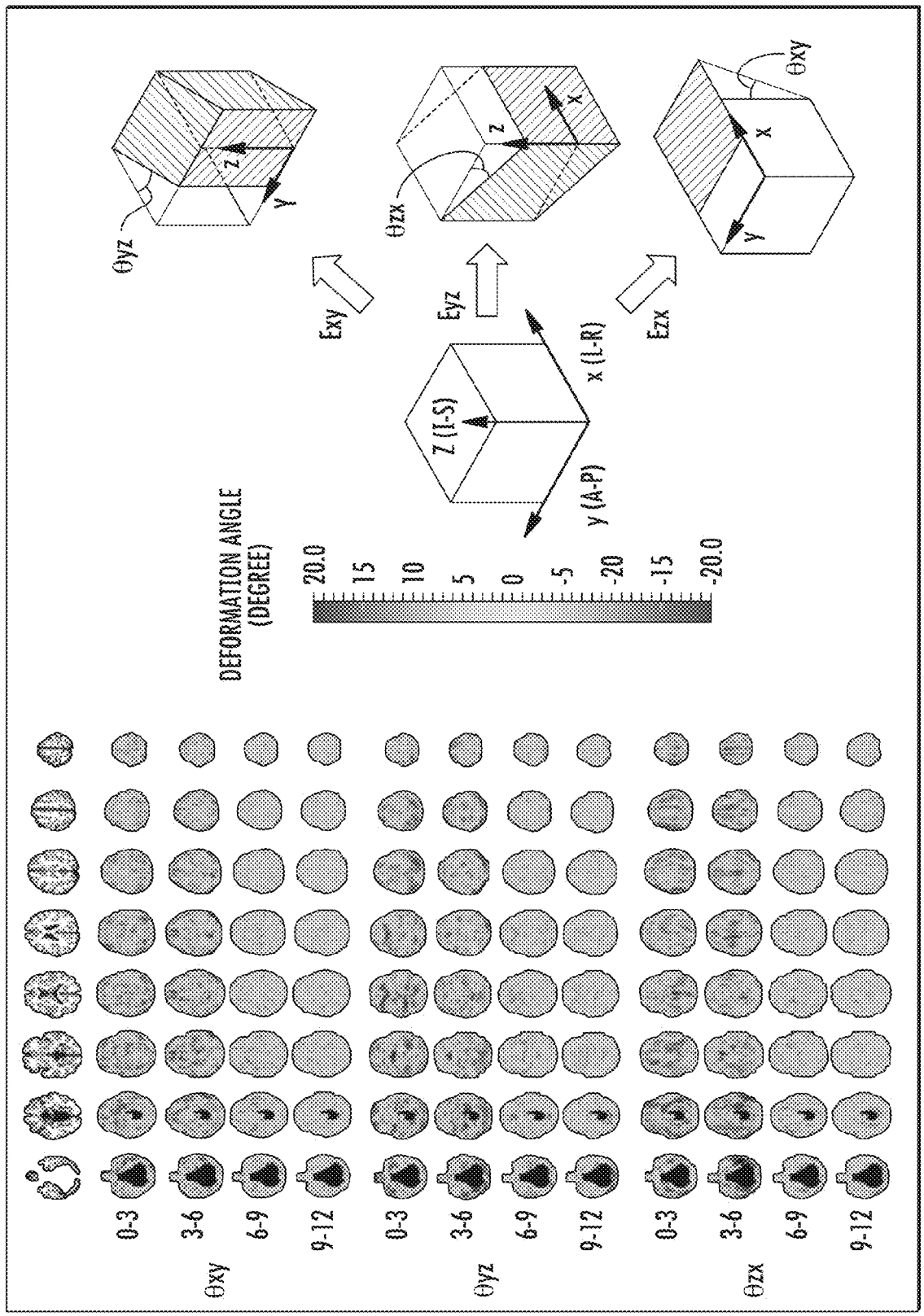
FIG. 29 illustrates mean deformation angles exerted by shear strains derived from off-diagonal components of Lagrange strain are showed for every 3 months of the first year of life according to embodiments of the present invention. Pictorial descriptions of the anticipated deformation profiles with respect to each shear stress are provided in the right column according to embodiments of the present invention. Gray cubes represent tissue elements before deformation, and green deformed cubes with red planes represent tissue element when positive shear strains are applied. Yellow (lighter) lines represent deformation angles according to embodiments of the present invention.

Even though shear strain does not contribute to volumetric change due to the symmetric property of strain tensor, it provides additional information on three-dimensional growth during brain development. Similar to the results of JD, high and spatially non-homogeneous shear strains (FIG. 29) are observed during the first 6 months of life. Here, the deformation angles exerted by shear strains between two originally perpendicular line elements (See Methods) better visualize the effects of shear strains. For y-directional deformation exerting on yz-plane ($\theta_{xy}$), left and right hemispheres show opposite directions, gray matter tends to deform toward the anterior direction in the frontal lobe and toward the posterior direction in the occipital lobe (upper row). However, z-directional deformation exerting on xz-plane showed opposite directions in the anterior-posterior and inferior-superior directions; that is, gray matter at the inferior regions tends to grow downward while superior regions tend to grow upward (middle row). X-directional deformation exerting on xy-plane ($\theta_{zx}$) showed opposite signs in left-right directions, suggesting that gray matter tends to deform to the left direction in the left hemisphere and to the right direction in the right hemisphere (lower row). During month 6-12, all shear strains showed more subtle changes as observed in other parameters.

Age Effects on Brain Development Profiles

Figure 30:
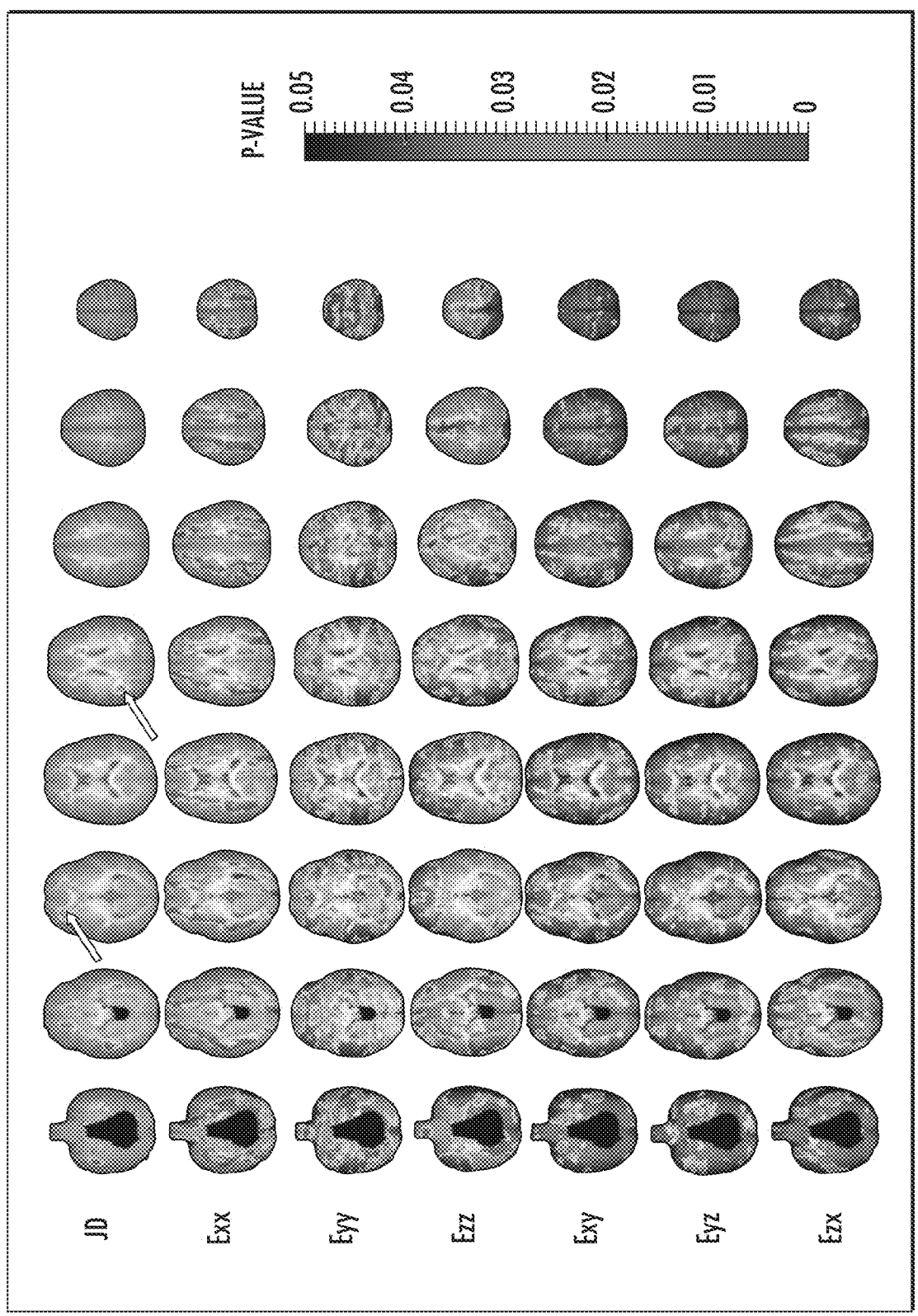
FIG. 30 are parametric images of age effects on volumetric and directional growth rates of the brain according to embodiments of the present invention. Most gray matter regions show statistically significant age effects. These regions correspond to higher growth regions during the first 6 months. In most cortical regions, volumetric growth rate decreases with age. However, anterior and posterior regions of corona radiata don't show significant age effect in volumetric growth rates (arrows). While directional elongations show significant age effect for most of the cortical regions, only limited regions show age effect in shear strains.

Effects of age on volumetric and directional growth rates estimated from a linear mixed effects model are shown in FIG. 30. Regions exhibiting statistically significant age effect are marked in red and green. With the exception of some areas at the anterior and posterior corona radiata, most of the gray matter regions showed age effect for JD. For directional elongations, direction-dependent age effects were observed in the gray matter, which is related with high Lagrange strains for the first 6 months (FIGS. 25-28). The lateral ventricles, cuneus, and temporal poles showed statistically significant age effect for all directions. On the other hand, age effect on shear strains was observed only in limited regions of the brain. Finally, the slopes of the regression lines were always negative for brain regions exhibiting statistically significant age effects, indicating linearly decreasing growth rates with age.

Discussion

The capability to reveal normal brain growth trajectories is of importance not only to understand the nature of brain development but also to potentially improve the diagnosis of neurodevelopmental disorders. Although a wealth of imaging studies on early brain development has been conducted, most of the results to date have been derived from either a cross-sectional design or with a relatively long time interval between two scans, i.e., one year[3,16], making it difficult to provide detailed characterization of brain growth trajectories. This study provides valuable normative insights into directional growth rates and their anisotropy using longitudinally acquired images with a relatively short time interval (3 months) between scans, capturing both non-linear and period-specific growth characteristics.

As shown in the JD maps (FIG. 24), the brain volume growth patterns are time-varying and inhomogeneous during the first year of life. Compared with a previous longitudinal study[9], similar volumetric growth patterns were observed: the slowest growing regions were sensory/motor regions and the fastest growing regions were insula and inferior temporal lobe. Slow and early postnatal growth of sensory/motor regions for the first year of life is possibly due to rapid maturation, which can be more precisely explainable from every 3 months JD maps. For the first 3 months, these regions show very high volumetric growth. However, after 3 months, growth phases markedly decreased. Fastest growth rates at lingual gyri and inferior temporal lobes (higher-order visual processing)[21] and fusiform gyri (involved with face recognition and color processing)[22] can be explained by continuing local volumetric growth for all four periods of time. Corresponding to this inhomogeneous regional volume growth, directional elongations (FIGS. 25-28) exhibit region-dependent anisotropic growth patterns in most of the cortical areas, which could play an important role in adult brain shape formation. The matured human brain is longer along the anterior-to-posterior direction and wider at the posterior part of the brain. This brain shape can be explained by anisotropic directional growth patterns in cortical regions during early infancy. During the first 6 months of life, active directional growths were observed (FIGS. 26-28) and characterized by x-directional (left-to-right) stretch of the temporal lobes and interhemispheric fissure making posterior regions wider, y-directional stretch of frontal and occipital lobes making the brain longer in anterior-to-posterior direction, and z-directional (superior-to-inferior) stretch of superior temporal and occipital lobes enhancing the growth along the rostro-caudal axis as observed in mammalian neuroanatomical development[23]. Starting at 9 months old, markedly uniform directional growth patterns are observed (FIG. 25), which imply that the formation of adult brain shape is largely completed by 9 months of age. However, an alternative conclusion could be if one considers the C-shaped development of primate cerebral cortex and incorporates limbic structures into the temporal lobe. DTI may be used to investigate the relationship between growth direction and fiber orientation of the white matter.

Asymmetric growth patterns were also observed during early brain development (FIG. 24). This finding is interesting since it has been documented that cerebral asymmetry is present at birth (leftward asymmetry)[24] while older children[25,26] and adults show the opposite pattern (rightward asymmetry)[27]. Even though it is difficult to directly compare our findings with previous studies reporting volumetric asymmetry of the cerebrum[10,24] due to differences in study design and scanning intervals, our results offer additional insights into the process from leftward asymmetry in infants to rightward asymmetry in older children and adults. Specifically, from month 0 to month 6, interhemispheric fissure regions of the right hemisphere showed active growth (Table 1). However, after month 6, asymmetric growth patterns became symmetrical with slow volumetric growth rates during this period. More studies encompassing an age range from early infancy to early adulthood may provide more solid evidences on this issue.

The time course of synaptic overproduction and retraction using human brain autopsy specimens revealed that the peak of synaptic overproduction in the visual cortex occurs at about fourth postnatal month, followed by the auditory cortex, angular gyrus and Broca's area, and, finally, the peak overproduction of medial prefrontal cortex was observed around one year of age[28]. This synaptogenesis time course, to a large extent, is similar to the JD results observed in our study, demonstrating volume expansion during the first year of life. More importantly, results on normal strains offered additional insights into the underlying directionally dependent volume expansion. Visual cortex and auditory show active volumetric growth mainly driven by y- and x/z-directional elongations for the first 6 months, respectively. The vision processing and higher cognitive areas (lingual, fusiform, inferior temporal, superior parietal gyri) show higher volumetric growth driven by relatively higher z-directional growth profiles during months 6 to 12 (FIGS. 24 and 25). In contrast, superior frontal and middle frontal gyri that represent the dorso-lateral prefrontal cortex (DLPFC) showed a high volumetric growth during the first 6 months of life ($JD^{0-3}>1.78$, $JD^{3-6}>1.39$), which were related with higher y- and z-directional stretches. Since it is well documented that DLPFC undergoes a prolonged period of maturation[18], the findings may suggest that the initial increase in JD in DLPFC during the first 6 months of life may be more related to the overall brain volumetric increase but not necessarily functionally related. More studies covering a wider age range than that included in the study may further characterize the temporal behaviors of JD in DLPFC. After month 9, as shown in one-sample T-test results on JD maps (FIG. 24), the whole brain growth rate becomes uniform showing non-significant volumetric growth before synaptic pruning starts in early childhood. Additionally, the anterior and posterior horns of the lateral ventricles showed rapid and isotropic growth rates for the first 3 months (FIG. 25). This finding is consistent with a previous study reporting the temporal characteristics of ventricular shape changes during early infancy[16]. Here, we need to note that this study focuses on structural changes and can only infer to the synaptogenesis and pruning as reported by other studies. Here, it is noted that this study focuses on structural changes and can only infer to the synaptogenesis and pruning as reported by other studies.

Figure 28:
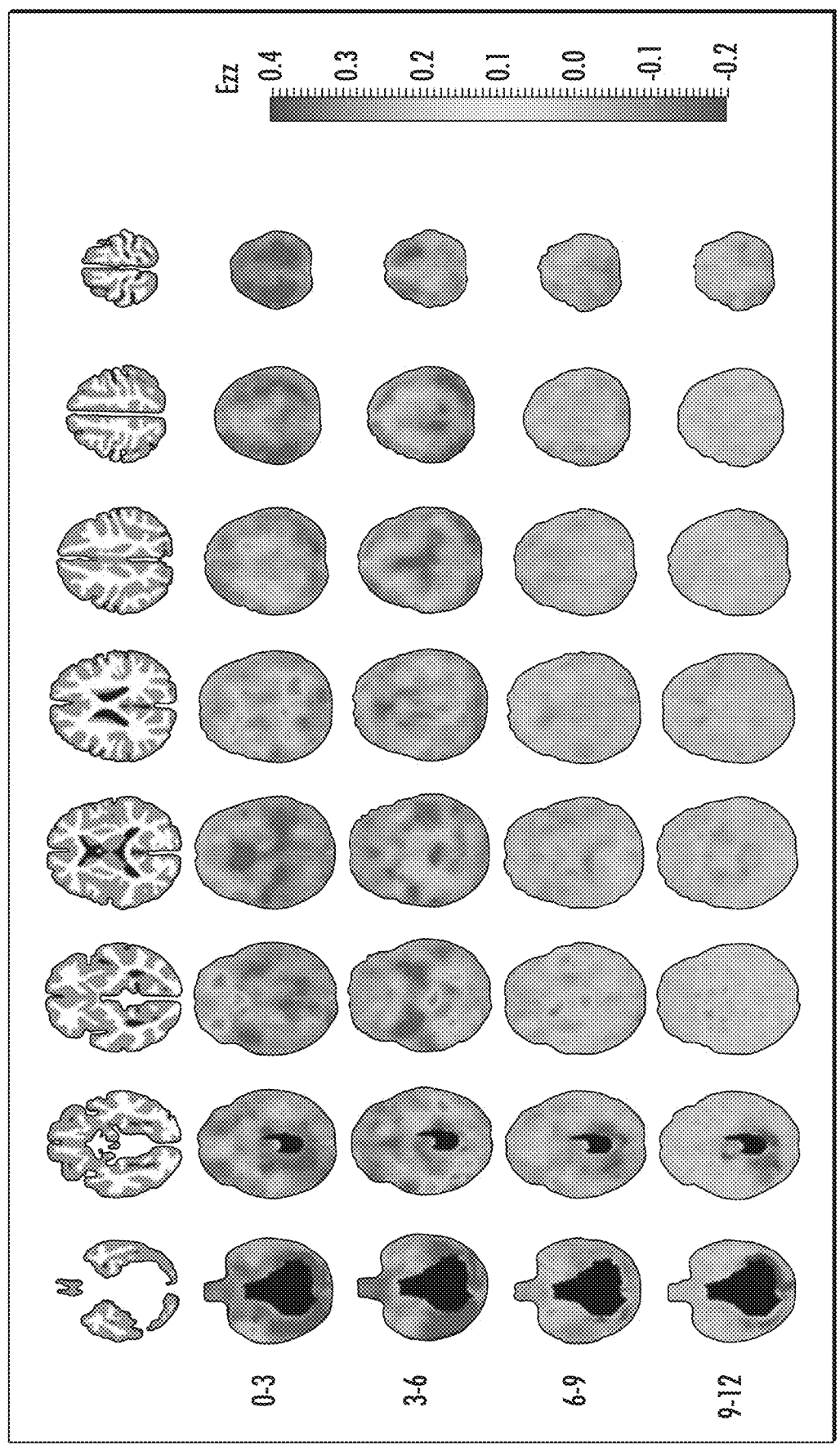
FIG. 28 are inferior to superior directional normal strains during the first year of life according to embodiments of the present invention.

Shear strains also provide important insights into brain growth. While normal strains (diagonal components) provide relative growth magnitudes along the main axes, we do not know, for example, whether a high z-directional growth of the lateral ventricles for the first three months is toward the superior direction or toward the inferior direction (FIG. 28). Referring to deformation angle $\theta_{yz}$ in that period (FIG. 29), it is apparent that downward growth (negative shear strain) is dominant in that period. Additionally, because shear stress is determined by shear strain and mechanical stiffness of the tissue, shear strains are potentially related to motility, proliferation, differentiation and survival of cells during brain development. Cells respond to mechanical signals in the form of externally applied forces and forces generated by cell-matrix and cell-cell contacts[31]. Here, we observed that shear strain is related to differential directional growth rates between gray matter and white matter. The white matter can be regarded as a fixed structure due to its lower growth rate in the first year of life while the gray matter exhibits an active growth rate during the same time period, leading to the observed shear deformations. Therefore, shear strain could play an important role in controlling the growth directions and local shape formation, interacting with directional elongations.

An increase of ICV up to two times of that at birth in the first year of life has been previously reported[3]. Regional brain volumetric increases have also been discerned using automated anatomical labeling-based volume analysis[9] and showed marked volume increases (66.3-147.5%) in all brain regions. Consistent with previous reports, our study also reveals active volumetric and directional growth patterns during the first three months of life (FIGS. 24 and 25). However, one unexpected growth pattern was observed at the anterior regions of corona radiata showing non-significant volume change for the first year of life (FIG. 24), which is in marked contrast to the growth pattern of the majority of gray matter. This phenomenon can potentially be explained from both physical and biological points of view. Specifically, rapid growth of the lateral ventricles (280% increase) and gray matter (149% increase) have been reported; both markedly outpace the growth of white matter (11% increase)[3] within the same time period. Structurally, white matter is located between the fast-growing lateral ventricles and gray matter. As a result, when the lateral ventricles push white matter outward, slow growing white matter will have to be stretched in response to the growth of the lateral ventricles. In addition, Bompard et al. reported a significant bilateral lengthening of the lateral ventricles and a significant increase of volume at the posterior portion of the ventricle during the first three months of life[1]. Together, these factors may attribute to growth patterns of the anterior corona radiata during the first three months of life showing significant local contraction in anterior-posterior direction (lower row of FIG. 25).

It is also of interest to compare infant brain growth patterns with those of a fetus. Fetal brains showed a higher volumetric growth in frontal and temporal lobes with a major anterior-to-posterior directional stretch during 15-22 gestational weeks[32]. Greater volume increases in parietal and occipital regions compared to the frontal lobes[33] were observed during 20-28 gestational weeks. Postnatally, infant brains also exhibited similar growth patterns to those of fetal brains during the first 3 months. Subsequently, regionally specific growth directions are observed between 3-9 months, followed by more isotropic directional growth patterns around months 9-12 (FIG. 24). Interestingly, while the fetal brain showed volumetric contraction in the lateral ventricle in the second trimester, possibly due to increase in the thickness of the cortical mantle relative to the ventricles[32], the infant brain shows the most active ventricular growth during the first year of life[1,3].

In conclusion, biomechanical analysis using longitudinal (MR) imaging provides additional insights beyond commonly employed volumetric approaches. Furthermore, with in vivo mechanical tissue properties available, driving forces for brain development can be identified using the finite element model and deformation parameters investigated in this study.

Methods

MR Image Acquisition

A total of 33 normal subjects (M/F=16/17) were recruited and imaged using a Siemens 3T scanner (TIM Trio, Siemens Medical System, Erlangen, Germany) with a 32-channel phased array coil. Each subject was scanned at 5 time points: 2 weeks, and 3, 6, 9, and 12 months of age. Of the 33 subjects, 22 subjects were included in one of our previous studies[12]. Inclusion criteria were birth between gestational age of 35 and 42 weeks, appropriate weight for gestational age, and the absence of major pregnancy and delivery complications as defined in the exclusion criteria. Exclusion criteria included maternal pre-eclampsia, placental abruption, neonatal hypoxia, any neonatal illness requiring greater than a 1-day stay at a neonatal intensive care unit, mother with HIV, mother using illegal drugs/narcotics during pregnancy, and any chromosomal or major congenital abnormality. Informed written consent was obtained from the parents of all participants. Before imaging, subjects were fed, swaddled, and fitted with ear protection. All subjects were in a natural sleep state during the imaging session. A board-certified neuroradiologist reviewed all images to verify that there were no apparent abnormalities.

A 3D MP-RAGE sequence was used to acquire images with 144 sagittal slices at a resolution of 1×1×1 mm$^3$. Imaging parameters were TR/TE/TI=1820/4.38/1100 ms and flip angle=7°. A Turbo spin echo T2-weighted sequence was employed to acquire 64 axial T2-weighted images at a resolution of 1.25×1.25×1.95 mm$^3$ using TR/TE=6750/20 ms, refocusing flip angle=150° and turbo factor=5. To mitigate the challenges of segmenting gray and white matter for images acquired at 6-8 months of age due to a poor gray/white matter contrast, diffusion tensor images consisting of 60 axial slices (2 mm in thickness) were obtained using an echo planar imaging sequence with imaging parameters: TR/TE=7680/82 ms, matrix size=128×96, 42 non-collinear diffusion gradients, and b=1000 s/mm$^2$. Seven non-diffusion-weighted reference scans were also acquired.

Image Registration and Processing

Figure 31:
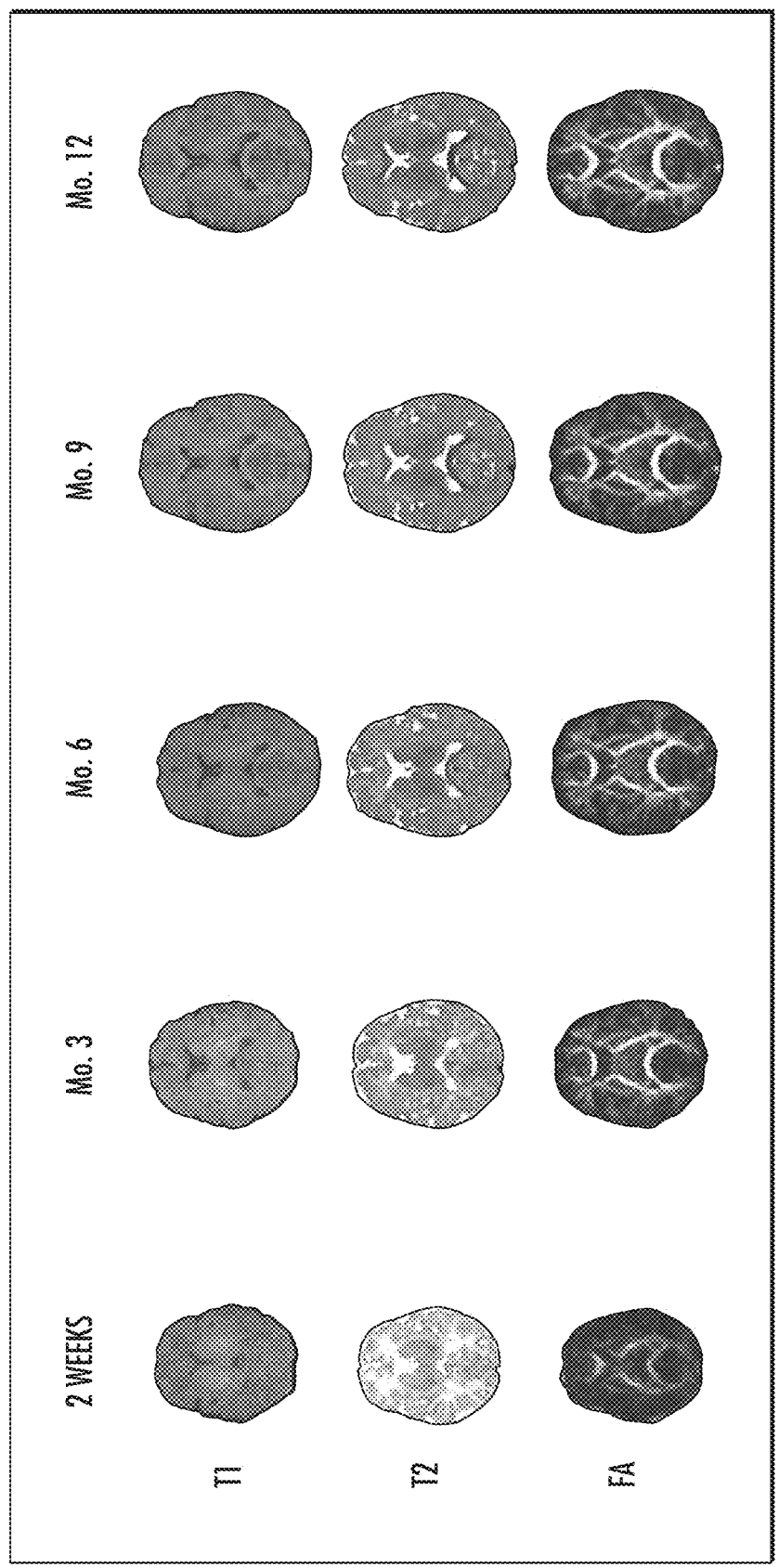
FIG. 31 are representative longitudinal images of T1, T2 and FA for a single subject.

Longitudinally acquired multi-modality images (FIG. 31) from each subject were registered using the framework proposed by Wang et al[12,34]. Preprocessing steps included skull stripping, N3-inhomogeneity correction, geometric distortion correction using field maps and non-linear registration. Subsequently, we conducted the within-subject longitudinal segmentation and registration consisting of the following two steps. (1) Single time-point tissue segmentation of MR images based on LINKS method[34]: the multi-source (T1, T2 and FA) images were used to iteratively estimate and refine tissue probability maps for GM, WM and CSF. As a learning-based approach, the segmentation framework consisted of two stages: training and testing stages. In the training stage, the classification forest was used to train a multi-class tissue classifier based on the training subjects with multiple modalities. The trained classifier provided the initial tissue probability maps for each training subject. The estimated tissue probability maps were further used as additional input images to train the next classifier, which combined the high-level multi-class context features from the estimated tissue probability maps with the appearance features from multi-modality images for refining tissue classification. By iteratively training the subsequent classifiers based on the updated tissue probability maps, a sequence of classifiers could be obtained. Similarly, in the testing stage, given a target subject, the learned classifiers were sequentially applied to iteratively refine the estimation of tissue probability maps by combining multimodality information with the previously-estimated tissue probability maps. Finally, to deal with the possible artifacts due to independent voxel-wise classification, we used patch-based sparse representation to impose an anatomical constraint[35] into the segmentation. (2) Iterative 4D registration and segmentation[36]: after tissue segmentation of each time-point, a temporally consistent constraint term was incorporated to further guide the segmentation based on the fact that global brain structures of the same full-term infant are closely preserved at different developmental stages. The constraint kept the distance between the tissue boundaries of the serial images within a biologically reasonable range. Specially, for a given time-point, all other time-points images can be registered into the given time-point image space via 4D segmentation-based HAMMER. Therefore, the distances between the WM/GM (GM/CSF) boundaries in the given time-point image and other warped WM/GM (GM/CSF) boundaries should be within a biologically reasonable range. This temporally consistent constraint term was effective to guide the segmentation, especially for the time-point with the low tissue contrast. Similarly, with the improved segmentation results for each time-point, the accuracy of 4D segmentation-based HAMMER registration will be also improved. During the HAMMER registration, the later time-point with large volume was first resampled into the same size of each early time-point (or usually named linear registration) and then deformable registration was performed. In this way, each voxel in early time-points had a corresponding voxel in the later time-point. Then, parameter maps of JD and Lagrange strains were registered to the final time point of each individual (month 12) to keep longitudinal consistency of registration using deformation fields from month 3, 6, 9 to month 12, respectively (FIG. 25). At this stage, all within-subject longitudinal growth parameters for every 3 months were mapped onto his/her final images space. Finally, for group analysis, the deformation fields from subjects at month 12 to infant atlas at year 1[37] were estimated using the same registration algorithm, which was applied to register all parameter maps onto the common space. Minimal smoothing (1 time edge-preserving smoothing) was applied at this step.

Figure 32:
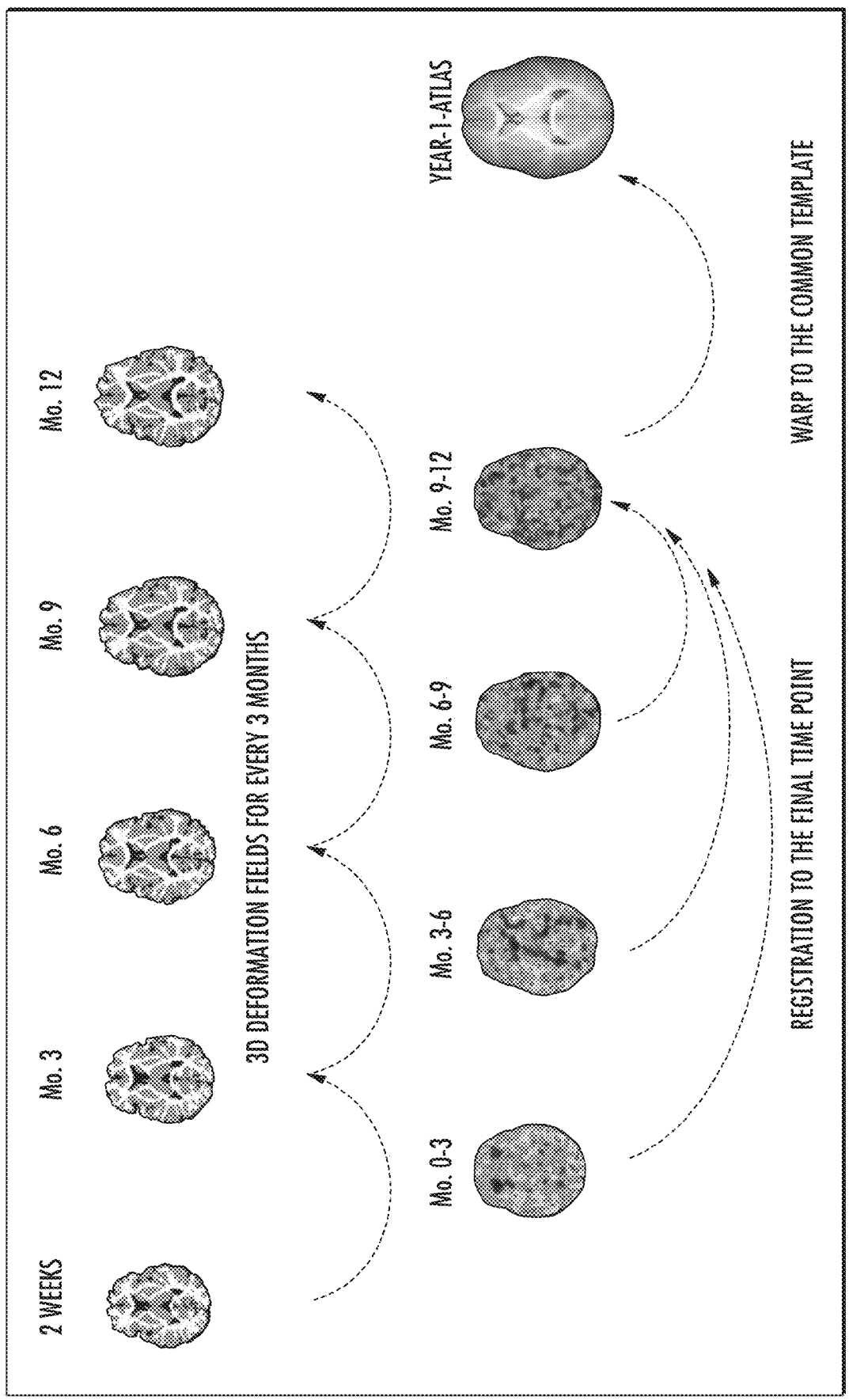
FIG. 32 are schematic illustrations of estimation of growth rates (JD and Lagrange strain) of the brain for the first year of life according to embodiments of the present invention. Using longitudinal segmentation/registration, 3D deformation fields of the 4 time periods (month 0-3, 3-6, 6-9 and 9-12) were derived. Volumetric and directional growth rates for every 3 months were estimated based on 3D deformation fields and finite strain theory. Parameters of growth rates were registered to the final time point of each subject and warped to the Year-1 infant Atlas for statistical analysis.
Figure 33A:
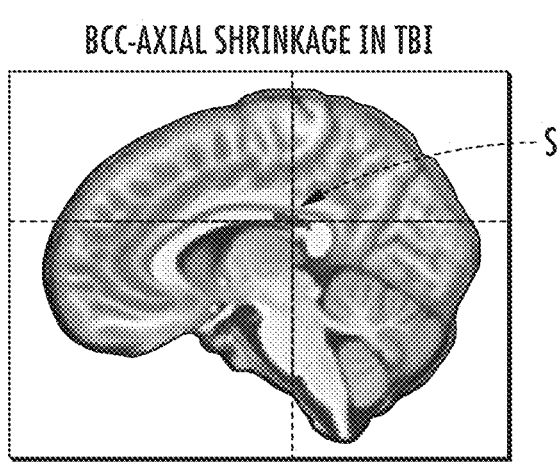
FIG. 33A is a visualization of a brain image showing BCC-axial shrinkage associated with traumatic brain injury (TBI) according to embodiments of the present invention.
Figure 33B:
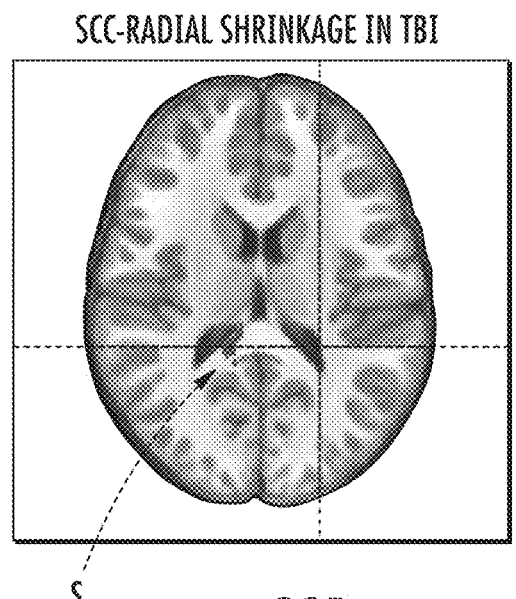
FIG. 33B is a visualization of a brain image of a youth football participant showing SCC-radial shrinkage associated with traumatic brain injury (TBI) according to embodiments of the present invention.
Figure 33C:
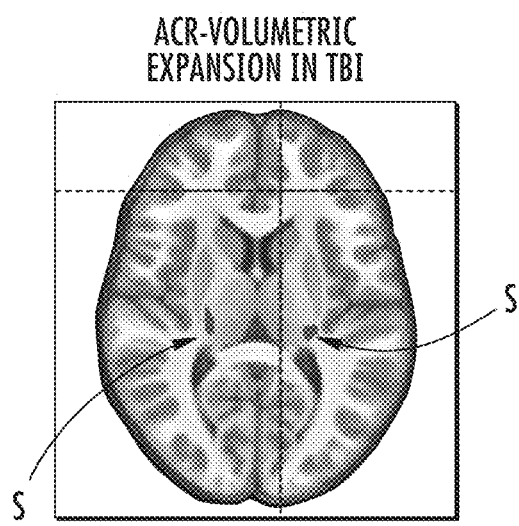
FIGS. 33C-33D are additional visualizations of the TBI-brain images as ACR, PLIC-volumetric expansions according to embodiments of the present invention
Figure 33D:
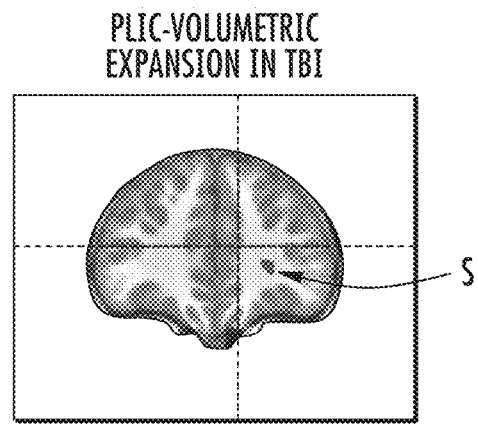

FIG. 32 provides schematic illustrations of estimation of growth rates (JD and Lagrange strain) of the brain for the first year of life according to embodiments of the present invention. Using longitudinal segmentation/registration, 3D deformation fields of the 4 time periods (month 0-3, 3-6, 6-9 and 9-12) were derived. Volumetric and directional growth rates for every 3 months were estimated based on 3D deformation fields and finite strain theory. Parameters of growth rates were registered to the final time point of each subject and warped to the Year-1 infant Atlas for statistical analysis.

Directional Strain Analysis Using Finite Strain Theory

The deformation gradient F is the fundamental measure of deformation in continuum mechanics. It is the second order tensor which maps line elements in the reference configuration to the one in the current configuration. In image registration, 3D deformation fields describe the voxel-wise displacements of each direction in the (typically Cartesian) coordinate system and through which deformation gradient tensor is defined by relating undeformed configuration (X coordinate) to deformed configuration (X coordinate):

$$F = \frac{\partial x_i}{\partial X_j} = \begin{bmatrix} \frac{\partial x_1}{\partial X_1} & \frac{\partial x_1}{\partial X_2} & \frac{\partial x_1}{\partial X_3} \\ \frac{\partial x_2}{\partial X_1} & \frac{\partial x_2}{\partial X_2} & \frac{\partial x_2}{\partial X_3} \\ \frac{\partial x_3}{\partial X_1} & \frac{\partial x_3}{\partial X_2} & \frac{\partial x_3}{\partial X_3} \end{bmatrix}, i, j = 1, 2, 3 \quad \text{Equation (1)}$$

JD describes the volume change ratio between undeformed and deformed configurations:

JD=det(F).

JD>1.0 represents volumetric expansion whereas JD<1.0 indicates volumetric contraction.

In continuum mechanics, one common choice for representing large strains between two different configurations is the Lagrange strain because it contains derivatives of the displacements with respect to the original configuration and can be conjugated with second Piola-Kirchhoff stress when the mechanical properties of material are known. Lagrange strain tensor is symmetric and describes directionally normal (diagonal components) and shear (off-diagonal components) strains:

$$E = \frac{1}{2}(F^T \cdot F - I) = \begin{bmatrix} E_{xx} & E_{xy} & E_{xz} \\ E_{yx} & E_{yy} & E_{yz} \\ E_{zx} & E_{zy} & E_{zz} \end{bmatrix} \quad \text{Equation (2)}$$

where I is a 3>3 identity matrix. When Lagrange strain E operates on a line element dX, it gives the changes in the squares of the undeformed (dX) and deformed length (dx):

$$\frac{|dx|^2 - |dX|^2}{2} \equiv dXEdX \quad \text{Equation (3)}$$

The eigenvalues of E are related to directional stretch ($\lambda$). When unit extension is defined as $(|dx_i|-|dX_i|)/|dX_i|=\lambda_i-1$, denoting the unit extension of $dX_i$ by the normal strain, $e_i$ in the direction $I_i$, diagonal components of Lagrange strain are related to the normal strain; $E_{ii}=e_i+\frac{1}{2}e_i^2$. Positive values of Lagrange strain indicate stretch of line element after deformation and vice versa. From the relationship between $E_{ii}$ and $\lambda_i$, anisotropy of directional growth rates (ADG) can be described using the concept of fractional anisotropy.

$$\lambda_i = \sqrt{2E_{ii}+1}, i = 1, 2, 3 \quad \text{Equation (4)}$$

$$ADG = \sqrt{\frac{1}{2}} \frac{\sqrt{(\lambda_1-\lambda_2)^2 + (\lambda_2-\lambda_3)^2 + (\lambda_3-\lambda_1)^2}}{\sqrt{\lambda_1^2 + \lambda_2^2 + \lambda_3^2}} \quad \text{Equation (5)}$$

Off-diagonal components (shear strains) are symmetric and related to directional stretches and deformation angle, $\phi_{12}$:

$$E_{12} = \frac{1}{2}\sqrt{2E_{11}+1}\sqrt{2E_{22}+1}\sin\phi_{12} = E_{21}, \phi_{12} = \frac{\pi}{2} - \theta \quad \text{Equation (6A)}$$

where, $\theta$ is the angle between two line elements that are organically perpendicular. Here, it is again noted that Lagrange strain describes deformation based on the coordinate system of material particles before deformation.

Equation 6A can be generalized as Equation 6B to represent the use of local coordinate systems.

$$E_{ij} = \frac{1}{2}\sqrt{2E_{ii}+1}\sqrt{2E_{ii}+1}\sin\phi_{ij} = E_{ji} \ \phi_{ij} = \frac{\pi}{2} - \theta \quad \text{Equation (6B)}$$

Statistical Analysis

One-sample t-test was performed to determine if volumetric and directional growth rates are statistically significant during the four time periods (month 0-3, 3-6, 6-9 and 9-12). Here, null hypothesis is that JD=1 or directional strain=0 at each image voxel. To better discern brain regions revealing prominent changes in JD and strains (both normal and shear strains), 90 regions-of-interest (ROIs) using AAL template were defined[37]. Mean values of JD and strains of each ROI were computed and we defined the prominent growth region when the mean value of ROI was greater than $75^{th}$ percentile of all voxels in the brain including white matter and cerebrospinal fluid. Finally, the linear mixed effects model proposed by Laird and Ware[38] was employed to determine age effects on the experimentally obtained longitudinal growth parameters using MATLAB R2013b (MathWorks, Natick, Mass.) software with the 'lme function'. Specifically, voxel-wise analyses of the JD and 6 components of Lagrange strains (3 diagonal and 3 off-diagonal components) were performed considering 'Age' as a fixed effect and a random intercept for each individual. Since these parameters were estimated from different scanning intervals among subjects, all parameters were adjusted by dividing number of days between scans and multiplying 90 to represent changes within every 3 months[39]. Additionally, the age at the midpoint of each time period was considered as covariate[8]. Corrections for multiple comparison were accomplished whenever needed using False Discovery Rate[40] for all of the above outlined statistical analyses and p-values less than 0.05 were considered statistically significant.

TABLES

TABLE 1

Fast growing regions where mean values of JD or direction strains were bigger than 75th percentile of the whole brain.

| Period | JD | Exx | Eyy | Ezz |
|---|---|---|---|---|
| Mo. 0-3 | Cingulum_Post_R, Lingual_L/R, Occipital_Sup_R, Occipital_Inf_R, Fusiform_R, Cuneus_R, Precuneus_R, Frontal_Sup_Medial_R, Calcarine_R, ParaHippocampal_R, Hippocampus_R | Cingulum_Ant_L/R, Cingulum_Mid_R, Cingulum_Post_R, Cuneus_R, Precuneus_R, Frontal_Sup_Medial_R, Calcarine_R, Frontal_Med_Orb_R, Supp_Motor_Area_R, Rectus_R, Olfactory_R, Paracentral_Lobule_R, Lingual_R, SupraMarginal_R, ParaHippocampal_R, Frontal_Inf_Tri_R | Cingulum_Post_R, Olfactory_L/R, Lingual_L/R, Occipital_Sup_L/R, Occipital_Mid_L/R, Occipital_Inf_L/R, Caudate_R, Frontal_Sup_Medial_L/R, Cuneus_L/R, Fusiform_R, Temporal_Pole_Sup_R, Angular_R, Calcarine_L | Occipital_Inf_R, Fusiform_L/R, Lingual_L/R, Heschl_L/R, Parietal_Sup_L, Parietal_Inf_R, Hippocampus_R, ParaHippocampal_R, Caudate_R, Temporal_Inf_R, Calcarine_R, Temporal_Sup_R |
| Mo. 3-6 | Cingulum_Ant_R, Cingulum_Mid_R, Cingulum_Post_R, Olfactory_R, Rectus_R, Fusiform_R, Occipital_Sup_L/R, Occipital_Mid_R, Occipital_Inf_L, Angular_R, Heschl_L, Insula_L, Cuneus_R, Precuneus_R, Frontal_Med_Orb_R | Cingulum_Ant_R, Cingulum_Mid_R, Cingulum_Post_R, Olfactory_R, Rectus_R, Fusiform_R, Insula_L, Precuneus_R, Heschl_L/R, Lingual_R, Frontal_Med_Orb_R, Occipital_Inf_L/R, Temporal_Sup_R, Temporal_Mid_L, Rolandic_Oper_R, SupraMarginal_L, Amygdala_R, ParaHippocampal_R | Cingulum_Ant_R, Occipital_Sup_L/R, Occipital_Mid_L/R, Occipital_Inf_L/R, Olfactory_L/R, Cuneus_L/R, Lingual_L/R, Fusiform_R, Angular_L/R, Parietal_Sup_R, Calcarine_R, Temporal_Pole_Sup_R | Cingulum_Ant_R, Cingulum_Mid_L/R, Fusiform_L/R, Rectus_L/R, Heschl_L, Olfactory_R, Angular_R, Paracentral_Lobule_R, Occipital_Sup_L/R, Occipital_Inf_R, Temporal_Inf_R, Temporal_Pole_Mid_L, Temporal_Pole_Mid_R, Rolandic_Oper_R, Frontal_Sup_Orb_L/R, Parietal_Inf_L/R, Pallidum_R, Putamen_L, Insula_R |
| Mo. 6-9 | Occipital_Sup_L, Occipital_Inf_R, Lingual_L/R, Fusiform_L/R, Temporal_Inf_R, Angular_L/R, Parietal_Sup_R | Occipital_Inf_R, Fusiform_L, Temporal_Inf_R, Insula_L, Parietal_Inf_R, ParaHippocampal_L | Occipital_Mid_L, Occipital_Sup_L, Angular_L/R, Cingulum_Post_L, Olfactory_R, Lingual_L | Occipital_Inf_R, Lingual_L/R, Fusiform_L/R, Temporal_Inf_R, Frontal_Sup_Orb_R, Parietal_Sup_R, Heschl_L, Rolandic_Oper_L |
| Mo. 9-12 | Lingual_L/R, Fusiform_L/R, Temporal_Inf_R, Temporal_Pole_Mid_L, Parietal_Sup_R, Occipital_Inf_R, Cingulum_Post_L, Angular_L, SupraMarginal_L/R, Parietal_Sup_L | Lingual_L/R, Fusiform_L, Temporal_Inf_R, Cingulum_Post_R, SupraMarginal_L, Occipital_Inf_R, Heschl_L, Caudate_L, Frontal_Sup_Orb_L, ParaHippocampal_R | Lingual_L/R, Fusiform_L/R, Temporal_Pole_Mid_L/R, Temporal_Inf_R, Parietal_Sup_R, Rectus_L/R, Frontal_Sup_Orb_L/R, Frontal_Mid_Orb_L/R, Frontal_Med_Orb_R, Rectus_R, Fusiform_L/R | Lingual_L/R, Fusiform_L/R, Temporal_Inf_R, Parietal_Sup_L/R, Occipital_Inf_R, Angular_L, Paracentral_Lobule_L, Cingulum_Post_L, SupraMarginal_R, ParaHippocampal_R |

TABLE 2

Slowly growing where mean values of JD or direction strains were less than 25$^{th}$ percentile of the whole brain.

| Period | JD | Exx | Eyy | Ezz |
|---|---|---|---|---|
| Mo. 0-3 | Cingulum_Mid_L, Cingulum_Post_L, Olfactory_L, Insula_R, Hippocampus_L, Amygdala_L | Insula_R, Frontal_Sup_R, Frontal_Sup_Orb_L/R, Frontal_Mid_Orb_R, Heschl_R, Hippocampus_L, Amygdala_L, Putamen_L, Caudate_L, Pallidum_L | Cingulum_Ant_L, Cingulum_Ant_R, Frontal_Inf_Tri_R, Temporal_Sup_R, Amygdala_L, | Cingulum_Ant_L, Cingulum_Mid_L/R, Frontal_Inf_Tri_R, Frontal_Med_Orb_L/R, Olfactory_L/R, Pallidum_R |
| Mo. 3-6 | Pallidum_L, Thalamus_R, Hippocampus_L, Amygdala_L | Amygdala_L, Putamen_L, Pallidum_L, Thalamus_L/R, Caudate_R | Pallidum_L/R, Amygdala_L/R, Paracentral_Lobule_L, Precentral_R, Postcentral_L/R, Rolandic_Oper_L | Hippocampus_L, Thalamus_L/R |
| Mo. 6-9 | Thalamus_L, Pallidum_R, Calcarine_R, Temporal_Pole_Sup_L/R, Temporal_Pole_Mid_R | Pallidum_R, Thalamus_L, Hippocampus_R, Frontal_Med_Orb_L, Supp_Motor_Area_R, Paracentral_Lobule_R, Cingulum_Ant_L, Cingulum_Mid_L/R, Olfactory_R | Temporal_Pole_Sup_L/R, Rolandic_Oper_L, Precentral_L | Pallidum_R, Caudate_L, Thalamus_R, Calcarine_R |
| Mo. 9-12 | Hippocampus_L, Pallidum_L/R, Amygdala_L, Calcarine_R, Olfactory_L/R, Temporal_Pole_Sup_R, Frontal_Inf_Orb_R | Pallidum_L, Cingulum_Ant_L, Rectus_R, Olfactory_R, Frontal_Med_Orb_L, Frontal_Sup_Medical_L, | Amygdala_R, Olfactory_L/R | Hippocampus_L, Pallidum_R, Amygdala_L, Olfactory_L, Calcarine_R, Frontal_Inf_Orb_L/R |

Example 2

Traumatic Brain Injury

FIGS. 33A-33D illustrate additional shrinkage brain regions S in brain images of youth football players which were detected by embodiments of the present invention using the methods of FIGS. 10 and 11 with the correction factors discussed with FIGS. 15A and 15B but were not detected by convectional volumetric measures.

Example 3

Exercise Intervention

FIGS. 34A-34C illustrate T1+FLAIR+DTI) visualizations with clusters C of axial strain associated with exercise intervention in MCI (mild cognitive impairment). There are three clusters C in FIG. 34A, four in FIG. 34B Adjacent the left angular gyrus) and three in FIG. 34C. There is less axial shrinkage and more stretch in an aerobic exercise group.

Figure 35A:
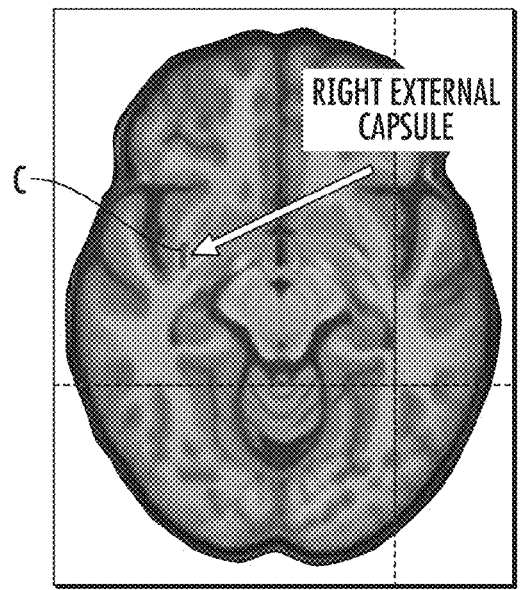
FIGS. 35A-35C are visualizations of the brain associated with exercise intervention for mild cognitive impairment showing clusters of radial strain according to embodiments of the present invention.
Figure 35B:
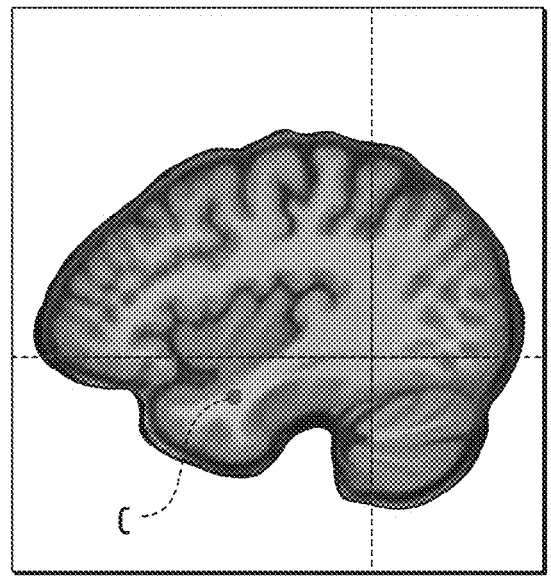
Figure 35C:
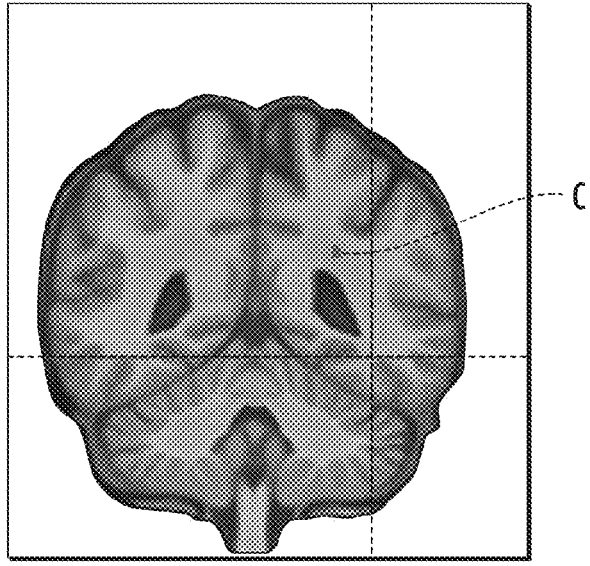

FIGS. 35A-35C illustrate radial strain clusters C in the visualizations, including at the right external capsule in FIG. 35A, one in FIG. 35B and one in FIG. 35C. There is less radial shrinkage/more stretch in control stretching group (higher T-statistics).

Example 4

Corrected PET Uptake Brain Images

Figure 36B:
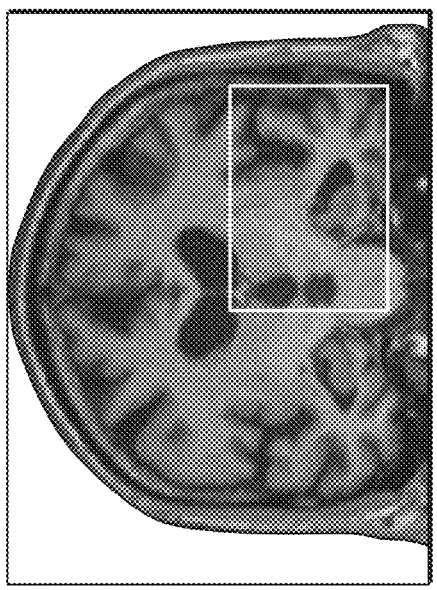
FIGS. 36A-36E are images/visualizations of a patient with Alzheimer's disease.
Figure 36A:
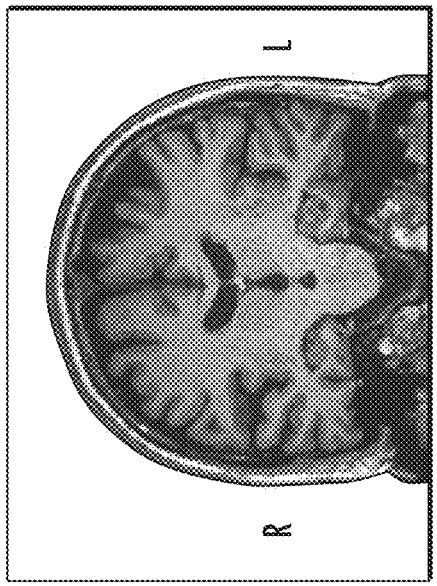
Figure 36E:
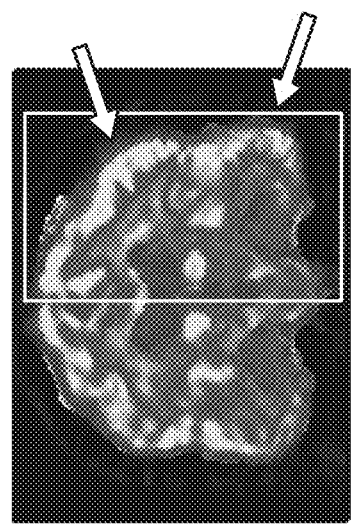
Figure 36D:
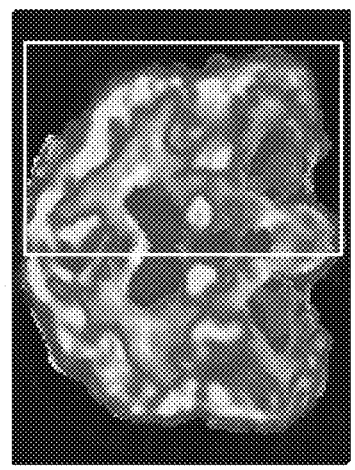
Figure 36C:
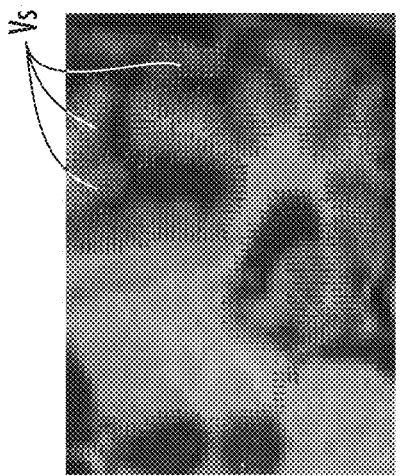

FIGS. 36A-36E are images/visualizations of a patient with Alzheimer's disease. FIG. 36A and FIG. 36B are visit 1 and 2 T1WI images, respectively. FIG. 36C is a visualization using surface normal vectors. Surface normal vectors Vs or Enn in gray matter (directionally encoded) from around the left temporal lobe (box in FIG. 36B) extracted using FREESURFER. FIG. 36D is an uncorrected Amyloid PET image using Pittsburgh compound B (PiB) and FIG. 36E is a directional atrophy corrected Amyloid PET image according to embodiments of the present invention. The arrows in FIG. 36E indicate increases in uptake value of PiB observed at central gyri and temporal lobe of the left hemisphere relative to uncorrected PET image of FIG. 36D.

Thus, the methods discussed above using the surface normal vectors (FIG. 15C) can be used with PET images to improve the longitudinal correction of uptake value of radioisotopes.

The following references were cited herein, including in the Examples Section, and are incorporated by reference as if recited in full herein.

REFERENCES

1. Bompard, L. et al. Multivariate longitudinal shape analysis of human lateral ventricles during the first twenty-four months of life. *PLoS One.* 9, e108306 (2014).
2. Gao, W. et al. Functional Network Development During the First Year: Relative Sequence and Socioeconomic Correlations. *Cereb Cortex.* 25, 2919-2928 (2015).
3. Knickmeyer, R. C. et al. A structural MRI study of human brain development from birth to 2 years. *J Neurosci.* 28, 12176-12182 (2008).
4. Courchesne, E., Carper, R. & Akshoomoff, N. Evidence of brain overgrowth in the first year of life in autism. *JAMA.* 290, 337-344 (2003).
5. Lee, A. D. et al. 3D pattern of brain abnormalities in Fragile X syndrome visualized using tensor-based morphometry. *Neuroimage.* 34, 924-938 (2007).
6. Gogtay, N. et al. Three-dimensional brain growth abnormalities in childhood-onset schizophrenia visualized by using tensor-based morphometry. *Proc Natl Acad Sci USA.* 105, 15979-15984 (2008).
7. Thompson, P. M. et al. Growth patterns in the developing brain detected by using continuum mechanical tensor maps. *Nature.* 404, 190-193 (2000).

8. Holland, D. et al. Structural growth trajectories and rates of change in the first 3 months of infant brain development. *JAMA Neurol.* 71, 1266-1274 (2014).
9. Gilmore, J. H. et al. Longitudinal development of cortical and subcortical gray matter from birth to 2 years. *Cereb Cortex.* 22, 2478-2485 (2012).
10. Choe, M. S. et al. Regional infant brain development: an MRI-based morphometric analysis in 3 to 13 month olds. *Cereb Cortex.* 23, 2100-2117 (2013).
11. Li, G. et al. Mapping longitudinal development of local cortical gyrification in infants from birth to 2 years of age. *J Neurosci.* 34, 4228-4238 (2014).
12. Wang, L. et al. 4D multi-modality tissue segmentation of serial infant images. *PLoS One.* 7, e44596 (2012).
13. Hazlett, H. C. et al. Magnetic resonance imaging and head circumference study of brain size in autism: birth through age 2 years. *Arch Gen Psychiatry.* 62, 1366-1376 (2005).
14. Ashburner, J. & Friston, K. J. in *Human Brain Function* (ed K. J. Friston R. S. J. Frackowiak, C. Frith, R. Dolan, K. J. Friston, C. J. Price, S. Zeki, J. Ashburner, and W. D. Penny) (Academic Press, 2003).
15. Ashburner, J. & Friston, K. J. Voxel-based morphometry—the methods. *Neuroimage.* 11, 805-821 (2000).
16. Aljabar, P. et al. Assessment of brain growth in early childhood using deformation-based morphometry. *Neuroimage.* 39, 348-358 (2008).
17. Studholme, C. & Cardenas, V. Population based analysis of directional information in serial deformation tensor morphometry. *Med mage Comput Comput Assist Interv.* 10, 311-318 (2007).
18. Lepore, N. et al. Generalized tensor-based morphometry of HIV/AIDS using multivariate statistics on deformation tensors. *IEEE Trans Med Imaging.* 27, 129-141 (2008).
19. Rajagopalan, V. et al. Mapping directionality specific volume changes using tensor based morphometry: an application to the study of gyrogenesis and lateralization of the human fetal brain. *Neuroimage.* 63, 947-958 (2012).
20. Kuhl, E. Growing matter: a review of growth in living systems. *J Mech Behav Biomed Mater.* 29, 529-543 (2014).
21. Sabatinelli, D. et al. Emotional perception: meta-analyses of face and natural scene processing. *Neuroimage.* 54, 2524-2533 (2011).
22. Kanwisher, N. & Yovel, G. The fusiform face area: a cortical region specialized for the perception of faces. *Philos Trans R Soc Lond B Biol Sci.* 361, 2109-2128 (2006).
23. Toro, R. On the Possible Shapes of the Brain. *Evolutionary Biology.* 39, 600-612 (2012).
24. Gilmore, J. H. et al. Regional gray matter growth, sexual dimorphism, and cerebral asymmetry in the neonatal brain. *J Neurosci.* 27, 1255-1260 (2007).
25. Matsuzawa, J. et al. Age-related volumetric changes of brain gray and white matter in healthy infants and children. *Cereb Cortex.* 11, 335-342 (2001).
26. Herbert, M. R. et al. Brain asymmetries in autism and developmental language disorder: a nested whole-brain analysis. *Brain.* 128, 213-226 (2005).
27. Toga, A. W. & Thompson, P. M. Mapping brain asymmetry. *Nat Rev Neurosci.* 4, 37-48 (2003).
28. Huttenlocher, P. R. & Dabholkar, A. S. Regional differences in synaptogenesis in human cerebral cortex. *J Comp Neurol.* 387, 167-178 (1997).
29. Gogtay, N. et al. Dynamic mapping of human cortical development during childhood through early adulthood. *Proc Natl Acad Sci USA.* 101, 8174-8179 (2004).
30. Deoni, S. C. et al. Mapping infant brain myelination with magnetic resonance imaging. *J Neurosci.* 31, 784-791 (2011).
31. Janmey, P. A. & Miller, R. T. Mechanisms of mechanical signaling in development and disease. *J Cell Sci.* 124, 9-18 (2011).
32. Zhan, J. et al. Spatial-temporal atlas of human fetal brain development during the early second trimester. *Neuroimage.* 82, 115-126 (2013).
33. Rajagopalan, V. et al. Local tissue growth patterns underlying normal fetal human brain gyrification quantified in utero. *J Neurosci.* 31, 2878-2887 (2011).
34. Wang, L. et al. LINKS: learning-based multi-source IntegratioN frameworK for Segmentation of infant brain images. *Neuroimage.* 108, 160-172 (2015).
35. Wang, L. et al. Integration of sparse multi-modality representation and anatomical constraint for isointense infant brain MR image segmentation. *Neuroimage.* 89, 152-164 (2014).
36. Shen, D. & Davatzikos, C. Measuring temporal morphological changes robustly in brain MR images via 4-dimensional template warping. *Neuroimage.* 21, 1508-1517 (2004).
37. Shi, F. et al. Infant brain atlases from neonates to 1- and 2-year-olds. *PLoS One.* 6, e18746 (2011).
38. Laird, N. M. & Ware, J. H. Random-effects models for longitudinal data. *Biometrics.* 38, 963-974 (1982).
39. Hua, X. et al. Detecting brain growth patterns in normal children using tensor-based morphometry. *Hum Brain Mapp.* 30, 209-219 (2009).
40. Benjamini, Y. & Hochberg, Y. Controlling the False Discovery Rate: A Practical and Powerful Approach to Multiple Testing. *Journal of the Royal Statistical Society. Series B (Methodological).* 57, 289-300 (1995).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A post-image acquisition method of evaluating medical images of a subject, comprising:
registering a region of interest in a first medical image taken at a first point in time to the region of interest (ROI) in a second image taken before or after the first medical image with voxels from the first and second medical images having a voxel-wise correspondence;
electronically defining a plurality of three-dimensional (3-D) finite elements in the ROI of the first image, each 3-D finite element defined by connecting lines to points associated with at least four voxels to establish a shape of each 3-D finite element in the ROI of the first image with associated original lengths and lines;

electronically deforming the 3-D finite elements in the ROI of the second medical image; then electronically calculating directional, shear and volume changes of the voxels in the ROI between the first and second images based on changes in lengths and angles of the lines in the deformed 3-D finite elements relative to the original lengths and angles.

2. The method of claim 1, wherein at least some of the 3-D finite elements have a three dimensional shape.

3. The method of claim 1, further comprising applying one or more deformation gradient tensors to the deformed 3-D finite elements before the electronically calculating, and wherein the one or more deformation gradient tensors provide a non-linear deformation and each voxel is evaluated for shape change in three dimensions using the original and deformed 3-D finite elements.

4. The method of claim 1, wherein the calculated directional changes are based on diagonal components for left-right (x-), anterior-posterior (y-), and inferior-superior (z) stretch associated with stretching and/or shrinking of voxels, and wherein the calculated shear changes are based on off-diagonal components for shear deformations to xy-, yz- and zx-planes.

5. The method of claim 1, further comprising quantitatively relating the determined directional and shear changes to volumetric changes in the region of interest.

6. The method of claim 1, further comprising identifying a disease state, disease progression or regression, or therapeutic influence associated with a morphometric change identified by one or more of the directional and shear changes.

7. The method of claim 1, further comprising generating a plurality of visualizations illustrating in color, the calculated directional and shear changes of the voxels in the region of interest.

8. The method of claim 1, wherein the calculated directional and shear changes can identify anisotropic and isotropic patterns even where there is no volume change of the region of interest between the first and second images.

9. The method of claim 1, wherein the first and second images are brain images, and wherein the directional and shear changes can identify directionally different brain degeneration or regeneration patterns.

10. The method of claim 1, further comprising electronically classifying the directional and shear changes as one of four groups of deformation topology types: Type I: isotropic directional change with a volumetric change; Type II: anisotropic directional change with a volumetric change; Type III: anisotropic directional change without a volumetric change; and Type IV: shear deformation.

11. The method of claim 1, further comprising generating color-scale and/or color-coded visualizations of 3-D topologies of the ROI based on the calculated directional and shear changes.

12. The method of claim 11, wherein the visualizations identify left-right stretch ($E_{xx}$), anterior-posterior stretch ($E_{yy}$), inferior-superior stretch ($E_{zz}$) and shear strains $E_{xy}$, $E_{yz}$ and $E_{zx}$ in corresponding shear planes.

13. The method of claim 1, further comprising:

identifying voxel-wise three dimensional shape changes using the calculated directional, shear and volume changes of the voxels in the ROI between the first and second images; and correcting a medical image of the ROI using calculated morphometric parameters provided at least in part by the calculated directional, shear and volume changes of the voxels.

14. The method of claim 1, further comprising:

converting three-dimensional deformation fields associated with the calculated directional, shear and volume changes of the voxels in the ROI of voxel-wise displacements in a Cartesian coordinate system to a local fiber-specific coordinate system to thereby obtain local deformation fields for each voxel; and calculating fiber-orientation-specific deformation measurements based on the converted three-dimensional deformation fields.

15. The method of claim 14, further comprising generating a visualization of the ROI that calculates $E_{11}$, $E_{22}$ and $E_{33}$ directional strains as morphometric parameters from the local coordinate system.

16. The method of claim 1, wherein the first and second images are T1WI brain images, the method further comprising:

defining Eigen vectors from a diffusion tensor imaging (DTI) image of the ROI to provide a local coordinate system;

co-registering local coordinates of the local coordinate system with the ROI of the first and/or second T1WI brain images;

defining local deformation fields for each voxel in the ROI; and calculating white matter fiber orientation-specific deformation measures using the local deformation fields.

17. The method of claim 16, wherein the local coordinate system $\{e_1, e_2, e_3\}$ is aligned with Eigen vectors co-registered onto T1WI space associated with the first and second images.

18. The method of claim 1, wherein the first and second images are brain images, the method further comprising:

obtaining a DTI or DWI brain image;

modeling fiber bundles in the DTI or DWI brain image as cylindrical shapes;

generating Eigen vectors aligned with $\{e_1, e_2, e_3\}$ directions of a local coordinate system associated with the cylindrical shapes;

co-registering the Eigen vectors to deformation fields generated by the calculated directional, shear and volume changes of the voxels;

identifying local deformation fields for each voxel in the ROI; and calculating fiber tract-specific morphometric parameters $E_{11}$, $E_{22}$, $E_{33}$, $E_{12}$, $E_{23}$ and $E_{31}$.

19. The method of claim 18, wherein the obtaining the DTI or DWI brain image is carried out to obtain a DTI image, wherein a single voxel in the ROI may comprise of single fiber or multiple crossing fibers, wherein the method further comprises for a respective single voxel having or multiple crossing fiber regions, providing Bayesian estimates for diffusion parameters to generate the Eigen vectors aligned with $\{e_1, e_2, e_3\}$ directions of the local coordinate system associated with the cylindrical shapes for each primary and secondary fiber bundle component;

wherein for each primary and secondary fiber bundle component, the method further comprises:

co-registering the Eigen vectors to deformation fields generated by the calculated directional, shear and volume changes of the voxels; then identifying the local deformation fields for each voxel in the ROI; and then
calculating the fiber tract-specific morphometric parameters $E_{11}$, $E_{22}$, $E_{33}$, $E_{12}$, $E_{23}$ and $E_{31}$.

20. The method of claim 18, wherein the obtaining the DTI or DWI brain image is carried out to obtain a DTI image, the method further comprising:
generating one or more voxel-wise diffusion parameter maps (one or more of FA, MD, AD, and RD) from the DTI image;
identifying whether there is brain tissue shrinkage in any of three directions of the local coordinate system;
applying correction factors for fiber tract-specific morphometric parameters $E_{11}$, $E_{22}$, $E_{33}$ $E_{12}$, $E_{23}$ and $E_{31}$ for directional strain parameters having negative values; and
generating one or more corrected voxel-wise diffusion parameter maps based on the applied correction factors thereby correcting over estimation of diffusion parameters.

21. The method of claim 20, wherein the correction factors comprise A, B, C, where $A=1+E_{11}$, $B=1+E_{22}$ and $C=1+E_{33}$, and wherein the corrected voxel-wise diffusion parameter map (DP') can be mathematically calculated by:

$$DP'=DP*A*B*C.$$

22. The method of claim 20, wherein the correction factors comprise $\lambda_1$, $\lambda_2$ and $\lambda_3$, which are directional stretch ratios, and wherein the one or more corrected voxel-wise diffusion parameter maps, DP', is equal to: $DP*\lambda_1*\lambda_2*\lambda_3$.

23. The method of claim 1, wherein the first and second images are T1WI brain images, the method further comprising:
identifying a gray matter-white matter tissue boundary specific shape change between the first and second images using surface normal vectors for directional strains normal to the tissue boundary ($E_{nn}$);
calculating local deformation fields using the surface normal vectors; and
correcting a voxel-wise Positron Emission Tomography (PET) uptake map using the calculated local deformation fields and the electronically calculated directional, shear and volume changes of the voxels in the ROI between the first and second images.

24. The method of claim 23, wherein a local coordinate system {$e_1$, $e_2$, $e_3$} associated with the gray matter-white matter tissue boundary specific shape change is aligned with the surface normal vectors on T1WI space associated with the first and second images for the local deformation fields.

25. The method of claim 23, further comprising:
generating one or more voxel-wise uncorrected uptake maps in PET before the correcting step; then
identifying whether there is brain tissue shrinkage in any of three directions of a local coordinate system associated with the directional strains Enn; then
applying correction factors for one or more surface-specific morphometric parameters $E_{11}$, $E_{22}$, $E_{33}$, $E_{12}$, $E_{23}$ and $E_{31}$ based at least in part on the local deformation fields; and
generating the corrected voxel-wise PET uptake map based on the applied correction factors thereby correcting directional atrophy in Amyloid/Tau/FDG (fluorodeoxyglucose) PET image of the brain.

26. A method of evaluating longitudinal medical images of a subject, comprising:
electronically defining three dimensional (3-D) finite elements in a region of interest in a first medical image of a subject, wherein the 3-D finite elements are each associated with at least four neighboring voxels, and wherein a shape of the 3-D finite elements is based on lines connecting points of positions of the at least four voxels;
electronically identifying or tracking the 3-D finite elements in a second medical image of the region of interest of the subject;
electronically calculating a change in dimensions of the lines connecting the at least four voxels and/or a change in the shape of the 3-D finite elements in the region of interest in the second medical image; and then
electronically calculating a plurality of morphometric parameters that identify directional and/or shear change in positions of voxels in the region of interest.

27. The method of claim 26, wherein the plurality of morphometric parameters comprise six morphometric parameters, including left-right (x-), anterior-posterior (y-), and inferior-superior (z-) as stretch/shrink directional change parameters, and xy-, yz- and zx-planes of shear deformation as shear strain parameters.

28. An image analysis system comprising:
a circuit in communication with at least one server and/or at least one processor that:
registers a region of interest in a first medical image taken at a first point in time to the region of interest (ROI) in a second image taken before or after the first medical image with voxels from the first and second medical images having a voxel-wise correspondence;
defines a plurality of three-dimensional (3-D) finite elements in the ROI of the first image, each 3-D finite element defined by connecting lines to points associated with at least four voxels to establish a shape of the 3-D finite element in the ROI of the first image with associated original lengths and lines;
deforms the 3-D finite elements in the ROI of the second medical image; then
calculates directional, shear and volume changes of the voxels in the ROI between the first and second images based on changes in lengths and angles of the lines in the deformed 3-D finite elements relative to the original lengths and angles.

29. The system of claim 28, wherein the at least one server and/or processor applies at least one deformation gradient tensor to the deformed 3-D finite elements for the calculations, and wherein the at least one deformation gradient tensor provides a non-linear deformation and each voxel is evaluated for change in three dimensions.

30. The system of claim 28, wherein the directional changes comprise diagonal components for left-right (x-), anterior-posterior (y-), and inferior-superior (z) stretch associated with stretching and/or shrinking, and wherein the shear changes comprise off-diagonal components for shear deformations to xy-, yz- and zx-planes in the deformation gradient tensors.

31. The system of claim 28, wherein the first and second images are brain images, and wherein the directional and shear changes can identify directionally different (anisotropic) brain degeneration or regeneration patterns even when a total volume of the ROI is unchanged.

32. The system of claim 28, at least partially onboard or in communication with a clinician workstation.

33. The system of claim 28, at least partially onboard or in communication with an imaging system.

34. The system of claim 28, wherein the circuit is configured to perform the operations of claim 2.

35. The method of claim 2, wherein the three dimensional shape is a tetrahedron shape or a cube shape.

* * * * *

UNITED STATES PATENT AND TRADEMARK OFFICE
CERTIFICATE OF CORRECTION

PATENT NO. : 10,949,973 B2
APPLICATION NO. : 16/349374
DATED : March 16, 2021
INVENTOR(S) : Kim et al.

Page 1 of 1

It is certified that error appears in the above-identified patent and that said Letters Patent is hereby corrected as shown below:

In the Specification

Column 14, Line 63: delete "(A)" and insert -- ($\lambda$) --

Column 20, Lines 16-17: delete "reference images (X coordinate)" and insert -- reference images ($x$ coordinate) --

Column 22, Line 45: delete "and a is" and insert -- and $\lambda$ is --

Column 35, Line 42: delete "(X coordinate)" and insert -- ($x$ coordinate) --

Signed and Sealed this
Eighth Day of June, 2021

Drew Hirshfeld
*Performing the Functions and Duties of the
Under Secretary of Commerce for Intellectual Property and
Director of the United States Patent and Trademark Office*